(12) United States Patent
Park et al.

(10) Patent No.: US 12,252,541 B2
(45) Date of Patent: Mar. 18, 2025

(54) ANTI-BCMA ANTIBODY AND USE THEREOF

(71) Applicant: ABL BIO INC., Gyeonggi-do (KR)

(72) Inventors: Kyungjin Park, Gyeonggi-Do (KR); Hyejin Chung, Gyeonggi-do (KR); Kyeongsu Park, Gyeonggi-do (KR); Yangsoon Lee, Gyeonggi-do (KR); Mikyung Chang, Gyeonggi-do (KR); Jaehyoung Jeon, Gyeonggi-do (KR); Youngkwang Kim, Gyeonggi-do (KR); Junhyun Jeong, Gyeonggi-do (KR); Jiseon Yoo, Gyeonggi-do (KR); Yeunju Kim, Gyeonggi-do (KR); Donghoon Yeom, Gyeonggi-do (KR); Eunjung Kim, Gyeonggi-do (KR); Bora Lee, Gyeonggi-do (KR); Jinwon Jung, Gyeonggi-do (KR)

(73) Assignee: ABL BIO INC., Gyeonggi-do (KR)

( * ) Notice: Subject to any disclaimer, the term of this patent is extended or adjusted under 35 U.S.C. 154(b) by 1124 days.

(21) Appl. No.: 17/053,256

(22) PCT Filed: Jun. 26, 2019

(86) PCT No.: PCT/KR2019/007727
§ 371 (c)(1),
(2) Date: Nov. 5, 2020

(87) PCT Pub. No.: WO2020/004934
PCT Pub. Date: Jan. 2, 2020

(65) Prior Publication Data
US 2021/0284749 A1 Sep. 16, 2021

(30) Foreign Application Priority Data
Jun. 26, 2018 (KR) .................. 10-2018-0073320

(51) Int. Cl.
*A61K 39/395* (2006.01)
*A61K 47/68* (2017.01)
*A61P 35/00* (2006.01)
*C07K 16/28* (2006.01)
*C07K 16/30* (2006.01)
*A61K 39/00* (2006.01)
*C07K 14/705* (2006.01)

(52) U.S. Cl.
CPC ...... *C07K 16/2878* (2013.01); *A61K 47/6849* (2017.08); *A61P 35/00* (2018.01); *C07K 16/30* (2013.01); *A61K 2039/505* (2013.01); *C07K 2317/33* (2013.01); *C07K 2317/565* (2013.01); *C07K 2317/732* (2013.01); *C07K 2317/76* (2013.01); *C07K 2317/92* (2013.01)

(58) Field of Classification Search
CPC ............ C07K 16/2866; C07K 16/2878; C07K 16/2896; C07K 2319/00; C07K 2317/73; C07K 2317/732; C07K 2317/76; C07K 2317/33; C07K 2317/56; C07K 2317/565; A61K 39/3955; A61K 39/39558; A61K 2039/505
See application file for complete search history.

(56) References Cited

U.S. PATENT DOCUMENTS

| | | | |
|---|---|---|---|
| 9,243,058 B2 | 1/2016 | Armitage et al. | |
| 2013/0273055 A1 | 10/2013 | Borges et al. | |
| 2016/0297885 A1 | 10/2016 | Kuo et al. | |
| 2017/0051068 A1 | 2/2017 | Pillarisetti et al. | |
| 2017/0233484 A1* | 8/2017 | Sussman ............ | A61K 47/6849 424/133.1 |
| 2017/0306036 A1 | 10/2017 | Vu et al. | |
| 2018/0118842 A1 | 5/2018 | Brentjens et al. | |
| 2019/0161552 A1 | 5/2019 | Kalled et al. | |

FOREIGN PATENT DOCUMENTS

| | | |
|---|---|---|
| CN | 107206076 A | 9/2017 |
| JP | 2017-532290 A | 11/2017 |
| KR | 10-2011-0126740 A | 11/2011 |
| WO | WO-2012/066058 A1 | 5/2012 |
| WO | WO-2016/090327 A2 | 6/2016 |
| WO | WO-2018/083204 A1 | 5/2018 |

OTHER PUBLICATIONS

Casset et al. A peptide mimetic of an anti-CD4 monoclonal antibody by rational design. Biochem Biophys Res Comm 307: 198-205, 2003.*
Chen et al. Selection and analysis of an optimized anti-VEGF antibody: crystal structure of an affinity-matured Fab in complex with antigen. J Mol Biol 293: 865-881, 1999.*
De Pascalis et al. Grafting of "abbreviated" complementarity-determining regions containing specificity-determining residues essential for ligand contact to engineer a less immunogenic humanized monoclonal antibody. J Immunol 169: 3076-3084, 2002.*
Holm et al. Functional mapping and single chain construction of the anti-cytokeratin 8 monoclonal antibody TS1. Mol Immunol 44: 1075-1084, 2007.*
Maccallum et al. Antibody-antigen interactions: contact analysis and binding site topography. J Mol Biol 262: 732-745, 1996.*
Paul, William E., Fundamental Immunology, 3rd Edition, Raven Press, New York, Chapt. 8, pp. 292-295 (1993).*
Rudikoff et al. Single amino acid substitution altering antigen-binding specificity. Proc Natl Acad Sci USA 79: 1979-1983, 1982.*
White et al. Cancer prevention for hte next generation. J Adolesc Health 52: S1-S7, 2013.*
Zhang et al. Comprehensive optimization of a single-chain variable domain antibody fragment as a targeting ligand for a cytotoxic nanoparticle. mAbs 7(1): 42-52, 2015 (published online Nov. 21, 2014).*

(Continued)

*Primary Examiner* — Bridget E Bunner
(74) *Attorney, Agent, or Firm* — Harness, Dickey & Pierce, P.L.C.

(57) ABSTRACT

Provided are an antibody or antigen-binding fragment thereof that specifically binds to a B-cell maturation antigen (BCMA), a method of preparing the same, and use thereof. Accordingly, these can be utilized in effectively preventing or treating cancers.

9 Claims, 26 Drawing Sheets

Specification includes a Sequence Listing.

(56) References Cited

OTHER PUBLICATIONS

Oden Felix et al: "Potent anti-tumor response by targeting B cell maturation antigen (BCMA) in a mouse model of multiple myeloma", Molecular Oncology, vol. 9, No. 7, pp. 1348-1358, XP029252531, 2015.
Dissertation: "Generation of an antibody targeting B cell maturation antigen for the treatment of multiple myeloma and autoimmune diseases", Apr. 1, 2014 (Apr. 1, 2014), XP055195743.
Kevin M. Friedman et al: "Effective Targeting of Multiple B-Cell Maturation Antigen-Expressing Hematological Malignances by Anti-B-Cell Maturation Antigen Chimeric Antigen Receptor T Cells", Human Gene Therapy, vol. 29, No. 5, May 1, 2018, pp. 585-601, XP055626881.
Extended European Search Report from corresponding EP Patent Application No. 19826406.1, dated Nov. 23, 2021.
Office Action from corresponding Japanese Patent Application No. 2020-559502, dated May 1, 2023.
Sanchez, et al. (2016) "Soluble B-Cell Maturation Antigen Mediates Tumor-Induced Immune Deficiency in Multiple Myeloma.", Myeloma Clinical Cancer Research, 22(13):3383-3397.
International Search Report (ISR) issued for corresponding International Patent Application No. PCTKR2019007727, dated Sep. 24, 2019, with English Translation.

* cited by examiner

SEQUENCE LISTING

<160> NUMBER OF SEQ ID NOS: 128

<210> SEQ ID NO 1
<211> LENGTH: 184
<212> TYPE: PRT
<213> ORGANISM: Artificial Sequence
<220> FEATURE:
<223> OTHER INFORMATION: Human BCMA(NP_001183.2)

<400> SEQUENCE: 1

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
        50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 2
<211> LENGTH: 53
<212> TYPE: PRT
<213> ORGANISM: Artificial Sequence
<220> FEATURE:
<223> OTHER INFORMATION: Rhesus BCMA (1-53)

<400> SEQUENCE: 2

Met Leu Gln Met Ala Arg Gln Cys Ser Gln Asn Glu Tyr Phe Asp Ser
1               5                   10                  15

Leu Leu His Asp Cys Lys Pro Cys Gln Leu Arg Cys Ser Ser Thr Pro
                20                  25                  30

Pro Leu Thr Cys Gln Arg Tyr Cys Asn Ala Ser Met Thr Asn Ser Val
            35                  40                  45

Lys Gly Met Asn Ala
        50

<210> SEQ ID NO 3
<211> LENGTH: 49
<212> TYPE: PRT
<213> ORGANISM: Artificial Sequence
<220> FEATURE:
<223> OTHER INFORMATION: Mouse BCMA (1-49)

-continued

<400> SEQUENCE: 3

Met Ala Gln Gln Cys Phe His Ser Glu Tyr Phe Asp Ser Leu Leu His
1               5                   10                  15

Ala Cys Lys Pro Cys His Leu Arg Cys Ser Asn Pro Ala Thr Cys
            20                  25                  30

Gln Pro Tyr Cys Asp Pro Ser Val Thr Ser Ser Val Lys Gly Thr Tyr
        35                  40                  45

Thr

<210> SEQ ID NO 4
<211> LENGTH: 49
<212> TYPE: PRT
<213> ORGANISM: Artificial Sequence
<220> FEATURE:
<223> OTHER INFORMATION: Rat BCMA (1-49)

<400> SEQUENCE: 4

Met Ala Gln Arg Cys Phe His Ser Glu Tyr Phe Asp Ser Leu Leu His
1               5                   10                  15

Ala Cys Lys Pro Cys Arg Leu Arg Cys Ser Asn Pro Pro Ala Pro Cys
            20                  25                  30

Gln Pro Tyr Cys Asp Pro Ser Met Thr Ser Ser Val Arg Gly Thr Tyr
        35                  40                  45

Thr

<210> SEQ ID NO 5
<211> LENGTH: 121
<212> TYPE: PRT
<213> ORGANISM: Artificial Sequence
<220> FEATURE:
<223> OTHER INFORMATION: Heavy chain variable region of anti-BCMA
      antibody B58

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Trp Ile Tyr Pro Ser Asp Ser Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ala Asn Lys Tyr Arg Gln Phe Asp Tyr Trp Gly
            100                 105                 110

Gln Gly Thr Leu Val Thr Val Ser Ser
        115                 120

<210> SEQ ID NO 6
<211> LENGTH: 117
<212> TYPE: PRT
<213> ORGANISM: Artificial Sequence
<220> FEATURE:
<223> OTHER INFORMATION: Heavy chain variable region of anti-BCMA
      antibody 5A6

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Val His Trp Val Arg Gln Ala Pro Gly Lys Gly Leu Glu Trp Val
        35                  40                  45

Ser Tyr Ile Ser Tyr Ser Gly Thr Tyr Tyr Asn Pro Ser Leu Lys
    50                  55                  60

Ser Arg Phe Thr Ile Ser Arg Asp Asn Ser Lys Asn Thr Leu Tyr Leu
65              70                  75                  80

Gln Met Asn Ser Leu Arg Ala Glu Asp Thr Ala Val Tyr Tyr Cys Ala
                85                  90                  95

Arg Asp Ser Asp Asp Phe Gly Phe Asp Tyr Trp Gly Gln Gly Thr Leu
            100                 105                 110

Val Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: Heavy chain variable region of anti-BCMA
      antibody 5D5

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Leu Ser Trp Val Arg Gln Ala Pro Gly Lys Gly Leu Glu Trp Val
        35                  40                  45

Ser Leu Ile Asp Ser Ser Gly Ser Ser Thr Phe Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Lys Glu His Gly Leu Phe Asp Ser Trp Gly Gln Gly Thr Leu Val
            100                 105                 110

Thr Val Ser Ser
        115

<210> SEQ ID NO 8
<211> LENGTH: 116
<212> TYPE: PRT
<213> ORGANISM: Artificial Sequence
<220> FEATURE:
<223> OTHER INFORMATION: Heavy chain variable region of anti-BCMA
      antibody 5B5

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly His
            20                  25                  30

Tyr Trp Ser Trp Val Arg Gln Ala Pro Gly Lys Gly Leu Glu Trp Val
        35                  40                  45

Ser Thr Val Ser Gly Ser Gly Gly Asp Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly His Ser Val Met Asp Val Trp Gly Gln Gly Thr Leu Val
            100                 105                 110

Thr Val Ser Ser
        115

<210> SEQ ID NO 9
<211> LENGTH: 115
<212> TYPE: PRT
<213> ORGANISM: Artificial Sequence
<220> FEATURE:
<223> OTHER INFORMATION: Heavy chain variable region of anti-BCMA
      antibody 2C6

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ser Ser Ile Asp Tyr Asn Gly Ser Thr Tyr Tyr Asn Pro Ser Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Glu His Gly Leu Phe Asp Ser Trp Gly Gln Gly Thr Leu Val Thr
            100                 105                 110

Val Ser Ser
        115

<210> SEQ ID NO 10
<211> LENGTH: 117
<212> TYPE: PRT
<213> ORGANISM: Artificial Sequence
<220> FEATURE:
<223> OTHER INFORMATION: Heavy chain variable region of anti-BCMA
      antibody 2F8

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ser Glu Ile Ile Pro Ile Phe Asp Thr Ser Asn Tyr Ala Gln Lys Phe
    50                  55                  60

Gln Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Lys Ile Pro Gly Asn Arg His Asp Tyr Trp Gly Gln Gly Thr Leu
            100                 105                 110

Val Thr Val Ser Ser
        115

<210> SEQ ID NO 11
<211> LENGTH: 116
<212> TYPE: PRT
<213> ORGANISM: Artificial Sequence
<220> FEATURE:
<223> OTHER INFORMATION: Heavy chain variable region of anti-BCMA
      antibody 4H9

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ser Met Ser Trp Val Arg Gln Ala Pro Gly Lys Gly Leu Glu Trp Val
        35                  40                  45

Ser Ser Ile Tyr His Thr Gly Tyr Thr Tyr Tyr Asn Pro Ser Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Lys Ser Gly Ala Phe Asp Ile Trp Gly Gln Gly Thr Leu Val
            100                 105                 110

Thr Val Ser Ser
        115

<210> SEQ ID NO 12
<211> LENGTH: 121
<212> TYPE: PRT
<213> ORGANISM: Artificial Sequence
<220> FEATURE:
<223> OTHER INFORMATION: Heavy chain variable region of anti-BCMA
      antibody 1H

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Ser His Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Val Tyr Ile Ile Glu Phe Glu Ser Leu Asp Ile Trp Gly
            100                 105                 110

Gln Gly Thr Leu Val Thr Val Ser Ser
        115                 120
```

```
<210> SEQ ID NO 13
<211> LENGTH: 121
<212> TYPE: PRT
<213> ORGANISM: Artificial Sequence
<220> FEATURE:
<223> OTHER INFORMATION: Heavy chain variable region of anti-BCMA
      antibody 2G

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Gly Tyr Tyr Gly Ser Ile Tyr Ala Phe Asp Tyr Trp Gly
            100                 105                 110

Gln Gly Thr Leu Val Thr Val Ser Ser
        115                 120

<210> SEQ ID NO 14
<211> LENGTH: 121
<212> TYPE: PRT
<213> ORGANISM: Artificial Sequence
<220> FEATURE:
<223> OTHER INFORMATION: Heavy chain variable region of anti-BCMA
      antibody 5G

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Ser Gln Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Ala Tyr Ile Ile Glu Phe Glu Ser Met Asp Ile Trp Gly
            100                 105                 110

Gln Gly Thr Leu Val Thr Val Ser Ser
        115                 120

<210> SEQ ID NO 15
<211> LENGTH: 118
<212> TYPE: PRT
<213> ORGANISM: Artificial Sequence
<220> FEATURE:
<223> OTHER INFORMATION: Heavy chain variable region of anti-BCMA
      antibody 5C3
```

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Ile His Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asp Leu Gly Asp Thr Thr Phe Asp Ser Trp Gly Gln Gly Thr
            100                 105                 110

Leu Val Thr Val Ser Ser
            115

<210> SEQ ID NO 16
<211> LENGTH: 110
<212> TYPE: PRT
<213> ORGANISM: Artificial Sequence
<220> FEATURE:
<223> OTHER INFORMATION: Light chain variable region of anti-BCMA
      antibody B58

<400> SEQUENCE: 16

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Ala Asp Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu
            100                 105                 110

<210> SEQ ID NO 17
<211> LENGTH: 107
<212> TYPE: PRT
<213> ORGANISM: Artificial Sequence
<220> FEATURE:
<223> OTHER INFORMATION: Light chain variable region of anti-BCMA
      antibody 5A6

<400> SEQUENCE: 17

Gln Ser Val Leu Thr Gln Pro Pro Ser Ala Ser Gly Thr Pro Gly Gln
1               5                   10                  15

Arg Val Thr Ile Ser Cys Gln Gly Asp Ser Leu Arg Ser Tyr Tyr Val
            20                  25                  30

Asn Trp Tyr Gln Gln Leu Pro Gly Thr Ala Pro Lys Leu Leu Ile Tyr
        35                  40                  45

```
Asp His Ser Lys Arg Pro Thr Gly Val Pro Asp Arg Phe Ser Gly Ser
            50                  55                  60

Lys Ser Gly Thr Ser Ala Ser Leu Ala Ile Ser Gly Leu Arg Ser Glu
 65                  70                  75                  80

Asp Glu Ala Asp Tyr Tyr Cys Gln Ser Tyr Asp Ser Ser Thr Val Val
                 85                  90                  95

Phe Gly Gly Gly Thr Lys Leu Thr Val Leu Gly
                100                 105

<210> SEQ ID NO 18
<211> LENGTH: 108
<212> TYPE: PRT
<213> ORGANISM: Artificial Sequence
<220> FEATURE:
<223> OTHER INFORMATION: Light chain variable region of anti-BCMA
      antibody 5D5

<400> SEQUENCE: 18

Glu Ile Val Leu Thr Gln Ser Pro Gly Thr Leu Ser Leu Ser Pro Gly
 1               5                  10                  15

Glu Arg Ala Thr Leu Ser Cys Lys Ala Ser Gln Asp Ile Asp Asp Asp
             20                  25                  30

Ile Asn Trp Tyr Gln Gln Lys Pro Gly Gln Ala Pro Arg Leu Leu Ile
             35                  40                  45

Tyr Asp Ala Ser Leu Arg Ala Thr Gly Ile Pro Asp Arg Phe Ser Gly
     50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Ser Leu Arg Thr Pro Ile
                 85                  90                  95

Thr Phe Gly Gln Gly Thr Lys Leu Glu Ile Lys Arg
                100                 105

<210> SEQ ID NO 19
<211> LENGTH: 108
<212> TYPE: PRT
<213> ORGANISM: Artificial Sequence
<220> FEATURE:
<223> OTHER INFORMATION: Light chain variable region of anti-BCMA
      antibody 5B5

<400> SEQUENCE: 19

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Gly Ile Asp Ser Tyr
             20                  25                  30

Val Ala Trp Tyr Gln Gln Lys Pro Gly Gln Ala Pro Arg Leu Leu Ile
             35                  40                  45

Tyr Asp Ala Ser Leu Arg Ala Thr Gly Ile Pro Asp Arg Phe Ser Gly
     50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Asn Ser Trp Pro Ile
                 85                  90                  95

Thr Phe Gly Gln Gly Thr Lys Leu Glu Ile Lys Arg
                100                 105

<210> SEQ ID NO 20
<211> LENGTH: 108
```

<212> TYPE: PRT
<213> ORGANISM: Artificial Sequence
<220> FEATURE:
<223> OTHER INFORMATION: Light chain variable region of anti-BCMA
      antibody 2C6

<400> SEQUENCE: 20

Glu Ile Val Leu Thr Gln Ser Pro Gly Thr Leu Ser Leu Ser Pro Gly
1               5                   10                  15

Glu Arg Ala Thr Leu Ser Cys Arg Val Ser Gln Ser Ile Ser Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Thr Arg Ala Ile Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Val Asn Ser Tyr Pro Ile
                85                  90                  95

Thr Phe Gly Gln Gly Thr Lys Val Glu Ile Lys Arg
            100                 105

<210> SEQ ID NO 21
<211> LENGTH: 105
<212> TYPE: PRT
<213> ORGANISM: Artificial Sequence
<220> FEATURE:
<223> OTHER INFORMATION: Light chain variable region of anti-BCMA
      antibody 2F8

<400> SEQUENCE: 21

Gln Ser Val Leu Thr Gln Pro Pro Ser Ala Ser Gly Thr Pro Gly Gln
1               5                   10                  15

Arg Val Thr Ile Ser Cys Thr Arg Met Gln Arg Gln Ser Asp Trp Tyr
            20                  25                  30

Gln Gln Leu Pro Gly Thr Ala Pro Lys Leu Leu Ile Tyr Asp Asn Asn
        35                  40                  45

Lys Arg Pro Leu Gly Val Pro Asp Arg Phe Ser Gly Ser Lys Ser Gly
    50                  55                  60

Thr Ser Ala Ser Leu Ala Ile Ser Gly Leu Arg Ser Glu Asp Glu Ala
65                  70                  75                  80

Asp Tyr Tyr Cys Gln Ser Tyr Asp Ser Asn Ala Tyr Val Val Phe Gly
                85                  90                  95

Gly Gly Thr Lys Leu Thr Val Leu Gly
            100                 105

<210> SEQ ID NO 22
<211> LENGTH: 108
<212> TYPE: PRT
<213> ORGANISM: Artificial Sequence
<220> FEATURE:
<223> OTHER INFORMATION: Light chain variable region of anti-BCMA
      antibody 4H9

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Asn
            20                  25                  30

Leu Ala Trp Tyr Gln Gln Lys Pro Gly Gln Ala Pro Arg Leu Leu Ile
            35                  40                  45

Tyr Gly Val Ser Ser Arg Ala Thr Gly Ile Pro Asp Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Thr Phe Gly Gln Gly Thr Lys Val Glu Ile Lys Arg
            100                 105

<210> SEQ ID NO 23
<211> LENGTH: 108
<212> TYPE: PRT
<213> ORGANISM: Artificial Sequence
<220> FEATURE:
<223> OTHER INFORMATION: Light chain variable region of anti-BCMA
      antibody 1H

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Trp
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys Arg
            100                 105

<210> SEQ ID NO 24
<211> LENGTH: 108
<212> TYPE: PRT
<213> ORGANISM: Artificial Sequence
<220> FEATURE:
<223> OTHER INFORMATION: Light chain variable region of anti-BCMA
      antibody 2G

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Thr Ser Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ser Phe Pro Trp
                85                  90                  95

Thr Phe Gly Gln Gly Thr Lys Val Glu Ile Lys Arg
            100                 105

```
<210> SEQ ID NO 25
<211> LENGTH: 108
<212> TYPE: PRT
<213> ORGANISM: Artificial Sequence
<220> FEATURE:
<223> OTHER INFORMATION: Light chain variable region of anti-BCMA
      antibody 5G

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys Arg
            100                 105

<210> SEQ ID NO 26
<211> LENGTH: 109
<212> TYPE: PRT
<213> ORGANISM: Artificial Sequence
<220> FEATURE:
<223> OTHER INFORMATION: Light chain variable region of anti-BCMA
      antibody 5C3

<400> SEQUENCE: 26

Glu Ile Val Leu Thr Gln Ser Pro Gly Thr Leu Ser Leu Ser Pro Gly
1               5                   10                  15

Glu Arg Ala Thr Leu Ser Cys Gln Ala Ser Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Gly Val Ser Asn Arg Ala Ser Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Tyr Ser Thr Pro Pro
                85                  90                  95

Ile Thr Phe Gly Gln Gly Thr Lys Leu Glu Ile Lys Arg
            100                 105

<210> SEQ ID NO 27
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 27

Asn Tyr Asp Met Ser
1               5
```

```
<210> SEQ ID NO 28
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 28

Asn Tyr Gly Val His
1               5

<210> SEQ ID NO 29
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 29

Asp Tyr Gly Leu Ser
1               5

<210> SEQ ID NO 30
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 30

Gly His Tyr Trp Ser
1               5

<210> SEQ ID NO 31
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 31

Asn Tyr Gly Met Ser
1               5

<210> SEQ ID NO 32
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 32

Gly Tyr Ser Met Ser
1               5

<210> SEQ ID NO 33
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 33

Asn Tyr Ala Met Ser
1               5

<210> SEQ ID NO 34
```

```
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 34

Asp Tyr Tyr Ile His
1               5

<210> SEQ ID NO 35
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 35

Trp Ile Tyr Pro Ser Asp Ser Ser Ile Tyr Tyr Ala Asp Ser Val Lys
1               5                   10                  15
Gly

<210> SEQ ID NO 36
<211> LENGTH: 16
<212> TYPE: PRT
<213> ORGANISM: Artificial Sequence
<220> FEATURE:
<223> OTHER INFORMATION: Heavy chain CDR2

<400> SEQUENCE: 36

Tyr Ile Ser Tyr Ser Gly Gly Thr Tyr Tyr Asn Pro Ser Leu Lys Ser
1               5                   10                  15

<210> SEQ ID NO 37
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 37

Leu Ile Asp Ser Ser Gly Ser Ser Thr Phe Tyr Ala Asp Ser Val Lys
1               5                   10                  15
Gly

<210> SEQ ID NO 38
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 38

Thr Val Ser Gly Ser Gly Gly Asp Thr Phe Tyr Ala Asp Ser Val Lys
1               5                   10                  15
Gly

<210> SEQ ID NO 39
<211> LENGTH: 16
<212> TYPE: PRT
<213> ORGANISM: Artificial Sequence
<220> FEATURE:
<223> OTHER INFORMATION: Heavy chain CDR2

<400> SEQUENCE: 39
```

```
Ser Ile Asp Tyr Asn Gly Ser Thr Tyr Tyr Asn Pro Ser Leu Lys Ser
1               5                   10                  15

<210> SEQ ID NO 40
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 40

Glu Ile Ile Pro Ile Phe Asp Thr Ser Asn Tyr Ala Gln Lys Phe Gln
1               5                   10                  15

Gly

<210> SEQ ID NO 41
<211> LENGTH: 16
<212> TYPE: PRT
<213> ORGANISM: Artificial Sequence
<220> FEATURE:
<223> OTHER INFORMATION: Heavy chain CDR2

<400> SEQUENCE: 41

Ser Ile Tyr His Thr Gly Tyr Thr Tyr Tyr Asn Pro Ser Leu Lys Ser
1               5                   10                  15

<210> SEQ ID NO 42
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 42

Gly Ile Ser His Ser Gly Ser Ser Thr Tyr Tyr Ala Asp Ser Val Lys
1               5                   10                  15

Gly

<210> SEQ ID NO 43
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 43

Ala Ile Ser Ser Ser Gly Ser Thr Ile Tyr Tyr Ala Asp Ser Val Lys
1               5                   10                  15

Gly

<210> SEQ ID NO 44
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 44

Gly Ile Ser Gln Ser Gly Ser Ser Thr Tyr Tyr Ala Asp Ser Val Lys
1               5                   10                  15

Gly

<210> SEQ ID NO 45
<211> LENGTH: 17
```

```
<212> TYPE: PRT
<213> ORGANISM: Artificial Sequence
<220> FEATURE:
<223> OTHER INFORMATION: Heavy chain CDR2

<400> SEQUENCE: 45

Ala Ile Ser Gly Ser Gly Gly Ser Thr Tyr Tyr Ala Asp Ser Val Lys
1               5                   10                  15
Gly

<210> SEQ ID NO 46
<211> LENGTH: 13
<212> TYPE: PRT
<213> ORGANISM: Artificial Sequence
<220> FEATURE:
<223> OTHER INFORMATION: Heavy chain CDR3

<400> SEQUENCE: 46

Arg Gly Pro Phe Ala Asn Lys Tyr Arg Gln Phe Asp Tyr
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Heavy chain CDR3

<400> SEQUENCE: 47

Arg Asp Ser Asp Asp Phe Gly Phe Asp Tyr
1               5                   10

<210> SEQ ID NO 48
<211> LENGTH: 8
<212> TYPE: PRT
<213> ORGANISM: Artificial Sequence
<220> FEATURE:
<223> OTHER INFORMATION: Heavy chain CDR3

<400> SEQUENCE: 48

Lys Glu His Gly Leu Phe Asp Ser
1               5

<210> SEQ ID NO 49
<211> LENGTH: 8
<212> TYPE: PRT
<213> ORGANISM: Artificial Sequence
<220> FEATURE:
<223> OTHER INFORMATION: Heavy chain CDR3

<400> SEQUENCE: 49

Arg Gly His Ser Val Met Asp Val
1               5

<210> SEQ ID NO 50
<211> LENGTH: 9
<212> TYPE: PRT
<213> ORGANISM: Artificial Sequence
<220> FEATURE:
<223> OTHER INFORMATION: Heavy chain CDR3

<400> SEQUENCE: 50

Lys Ile Pro Gly Asn Arg His Asp Tyr
1               5

<210> SEQ ID NO 51
```

```
<211> LENGTH: 9
<212> TYPE: PRT
<213> ORGANISM: Artificial Sequence
<220> FEATURE:
<223> OTHER INFORMATION: Heavy chain CDR3

<400> SEQUENCE: 51

Arg Tyr Lys Ser Gly Ala Phe Asp Ile
1               5

<210> SEQ ID NO 52
<211> LENGTH: 12
<212> TYPE: PRT
<213> ORGANISM: Artificial Sequence
<220> FEATURE:
<223> OTHER INFORMATION: Heavy chain CDR3

<400> SEQUENCE: 52

His Val Tyr Ile Ile Glu Phe Glu Ser Leu Asp Ile
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Heavy chain CDR3

<400> SEQUENCE: 53

Ala Gly Tyr Tyr Gly Ser Ile Tyr Ala Phe Asp Tyr
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Heavy chain CDR3

<400> SEQUENCE: 54

His Ala Tyr Ile Ile Glu Phe Glu Ser Met Asp Ile
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Heavy chain CDR3

<400> SEQUENCE: 55

Ser Asp Leu Gly Asp Thr Thr Phe Asp Ser
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Light chain CDR1

<400> SEQUENCE: 56

Ser Gly Ser Ser Ser Asn Ile Gly Ser Asn Ser Val Ser
1               5                   10

<210> SEQ ID NO 57
<211> LENGTH: 11
```

```
<212> TYPE: PRT
<213> ORGANISM: Artificial Sequence
<220> FEATURE:
<223> OTHER INFORMATION: Light chain CDR1

<400> SEQUENCE: 57

Gln Gly Asp Ser Leu Arg Ser Tyr Tyr Val Asn
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Light chain CDR1

<400> SEQUENCE: 58

Lys Ala Ser Gln Asp Ile Asp Asp Asp Ile Asn
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Light chain CDR1

<400> SEQUENCE: 59

Arg Ala Ser Gln Gly Ile Asp Ser Tyr Val Ala
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Light chain CDR1

<400> SEQUENCE: 60

Arg Val Ser Gln Ser Ile Ser Ser Tyr Leu Asn
1               5                   10

<210> SEQ ID NO 61
<211> LENGTH: 8
<212> TYPE: PRT
<213> ORGANISM: Artificial Sequence
<220> FEATURE:
<223> OTHER INFORMATION: Light chain CDR1

<400> SEQUENCE: 61

Thr Arg Met Gln Arg Gln Ser Asp
1               5

<210> SEQ ID NO 62
<211> LENGTH: 11
<212> TYPE: PRT
<213> ORGANISM: Artificial Sequence
<220> FEATURE:
<223> OTHER INFORMATION: Light chain CDR1

<400> SEQUENCE: 62

Arg Ala Ser Gln Ser Val Ser Arg Asn Leu Ala
1               5                   10

<210> SEQ ID NO 63
<211> LENGTH: 11
<212> TYPE: PRT
```

<213> ORGANISM: Artificial Sequence
<220> FEATURE:
<223> OTHER INFORMATION: Light chain CDR1

<400> SEQUENCE: 63

Arg Ala Ser Gln Ser Ile Ser Asn Trp Leu Asn
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Light chain CDR1

<400> SEQUENCE: 64

Arg Ala Ser Gln Ser Ile Ser Ser Tyr Leu Asn
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Light chain CDR1

<400> SEQUENCE: 65

Gln Ala Ser Asp Asp Ile Ser Asn Tyr Leu Asn
1               5                   10

<210> SEQ ID NO 66
<211> LENGTH: 7
<212> TYPE: PRT
<213> ORGANISM: Artificial Sequence
<220> FEATURE:
<223> OTHER INFORMATION: Light chain CDR2

<400> SEQUENCE: 66

Ala Asp Ser Lys Arg Pro Ser
1               5

<210> SEQ ID NO 67
<211> LENGTH: 7
<212> TYPE: PRT
<213> ORGANISM: Artificial Sequence
<220> FEATURE:
<223> OTHER INFORMATION: Light chain CDR2

<400> SEQUENCE: 67

Asp His Ser Lys Arg Pro Thr
1               5

<210> SEQ ID NO 68
<211> LENGTH: 7
<212> TYPE: PRT
<213> ORGANISM: Artificial Sequence
<220> FEATURE:
<223> OTHER INFORMATION: Light chain CDR2

<400> SEQUENCE: 68

Asp Ala Ser Leu Arg Ala Thr
1               5

<210> SEQ ID NO 69
<211> LENGTH: 7
<212> TYPE: PRT
<213> ORGANISM: Artificial Sequence

```
<220> FEATURE:
<223> OTHER INFORMATION: Light chain CDR2

<400> SEQUENCE: 69

Asp Ala Ser Thr Arg Ala Ile
1               5

<210> SEQ ID NO 70
<211> LENGTH: 7
<212> TYPE: PRT
<213> ORGANISM: Artificial Sequence
<220> FEATURE:
<223> OTHER INFORMATION: Light chain CDR2

<400> SEQUENCE: 70

Asp Asn Asn Lys Arg Pro Leu
1               5

<210> SEQ ID NO 71
<211> LENGTH: 4
<212> TYPE: PRT
<213> ORGANISM: Artificial Sequence
<220> FEATURE:
<223> OTHER INFORMATION: Light chain CDR2

<400> SEQUENCE: 71

Gly Val Ser Ser
1

<210> SEQ ID NO 72
<211> LENGTH: 7
<212> TYPE: PRT
<213> ORGANISM: Artificial Sequence
<220> FEATURE:
<223> OTHER INFORMATION: Light chain CDR2

<400> SEQUENCE: 72

Ala Ala Ser Ser Leu Gln Ser
1               5

<210> SEQ ID NO 73
<211> LENGTH: 7
<212> TYPE: PRT
<213> ORGANISM: Artificial Sequence
<220> FEATURE:
<223> OTHER INFORMATION: Light chain CDR2

<400> SEQUENCE: 73

Ala Thr Ser Arg Leu Gln Ser
1               5

<210> SEQ ID NO 74
<211> LENGTH: 7
<212> TYPE: PRT
<213> ORGANISM: Artificial Sequence
<220> FEATURE:
<223> OTHER INFORMATION: Light chain CDR2

<400> SEQUENCE: 74

Gly Val Ser Asn Arg Ala Ser
1               5

<210> SEQ ID NO 75
<211> LENGTH: 11
<212> TYPE: PRT
<213> ORGANISM: Artificial Sequence
<220> FEATURE:
```

```
<223> OTHER INFORMATION: Light chain CDR3

<400> SEQUENCE: 75

Gly Ser Trp Asp Tyr Ser Leu Ser Gly Tyr Val
1               5                   10

<210> SEQ ID NO 76
<211> LENGTH: 8
<212> TYPE: PRT
<213> ORGANISM: Artificial Sequence
<220> FEATURE:
<223> OTHER INFORMATION: Light chain CDR3

<400> SEQUENCE: 76

Gln Ser Tyr Asp Ser Ser Thr Val
1               5

<210> SEQ ID NO 77
<211> LENGTH: 8
<212> TYPE: PRT
<213> ORGANISM: Artificial Sequence
<220> FEATURE:
<223> OTHER INFORMATION: Light chain CDR3

<400> SEQUENCE: 77

Gln Gln Ser Leu Arg Thr Pro Ile
1               5

<210> SEQ ID NO 78
<211> LENGTH: 8
<212> TYPE: PRT
<213> ORGANISM: Artificial Sequence
<220> FEATURE:
<223> OTHER INFORMATION: Light chain CDR3

<400> SEQUENCE: 78

Gln Gln Tyr Asn Ser Trp Pro Ile
1               5

<210> SEQ ID NO 79
<211> LENGTH: 9
<212> TYPE: PRT
<213> ORGANISM: Artificial Sequence
<220> FEATURE:
<223> OTHER INFORMATION: Light chain CDR3

<400> SEQUENCE: 79

Gln Gln Val Asn Ser Tyr Pro Ile Thr
1               5

<210> SEQ ID NO 80
<211> LENGTH: 10
<212> TYPE: PRT
<213> ORGANISM: Artificial Sequence
<220> FEATURE:
<223> OTHER INFORMATION: Light chain CDR3

<400> SEQUENCE: 80

Gln Ser Tyr Asp Ser Asn Ala Tyr Val Val
1               5                   10

<210> SEQ ID NO 81
<211> LENGTH: 9
<212> TYPE: PRT
<213> ORGANISM: Artificial Sequence
<220> FEATURE:
<223> OTHER INFORMATION: Light chain CDR3
```

<400> SEQUENCE: 81

Gln Gln Tyr Gly Ser Ser Pro Pro Thr
1               5

<210> SEQ ID NO 82
<211> LENGTH: 9
<212> TYPE: PRT
<213> ORGANISM: Artificial Sequence
<220> FEATURE:
<223> OTHER INFORMATION: Light chain CDR3

<400> SEQUENCE: 82

Gln Gln Ser Tyr Ser Thr Pro Trp Thr
1               5

<210> SEQ ID NO 83
<211> LENGTH: 9
<212> TYPE: PRT
<213> ORGANISM: Artificial Sequence
<220> FEATURE:
<223> OTHER INFORMATION: Light chain CDR3

<400> SEQUENCE: 83

Gln Gln Ser Ser Ser Phe Pro Trp Thr
1               5

<210> SEQ ID NO 84
<211> LENGTH: 9
<212> TYPE: PRT
<213> ORGANISM: Artificial Sequence
<220> FEATURE:
<223> OTHER INFORMATION: Light chain CDR3

<400> SEQUENCE: 84

Gln Gln Ser Tyr Ser Thr Pro Pro Ile
1               5

<210> SEQ ID NO 85
<211> LENGTH: 363
<212> TYPE: DNA
<213> ORGANISM: Artificial Sequence
<220> FEATURE:
<223> OTHER INFORMATION: Polynucleotide encoding heavy chain variable
      region of anti-BCMA antibody B58

<400> SEQUENCE: 85
gaggtgcagc tgctggagtc cggcggcggc ctggtgcagc ccggcggctc cctgcggctg      60
tcctgcgccg cctccggctt caccttctcc aactacgaca tgtcctgggt gcggcaggcc     120
cccggcaagg gcctggagtg ggtgtcctgg atctacccct ccgactcctc catctactac     180
gccgactccg tgaagggccg gttcaccatc tcccgggaca ctccaagaa caccctgtac      240 ctgcagatga actccctgcg ggccgaggac accgccgtgt actactgcgc ccggggcccc     300
ttcgccaaca gtaccggca gttcgactac tggggccagg gcaccctggt gaccgtgtcc      360
tcc                                                                    363

<210> SEQ ID NO 86
<211> LENGTH: 351
<212> TYPE: DNA
<213> ORGANISM: Artificial Sequence
<220> FEATURE:
<223> OTHER INFORMATION: Polynucleotide encoding heavy chain variable
      region of anti-BCMA antibody 5A6

<400> SEQUENCE: 86

```
gaggtccagt tgttggaaag cggtggtggt ttggttcaac caggcggtag cctcagactc    60
tcctgcgctg cctccgggtt tactttcagt aactatggag tacattgggt cagacaagcc   120
cccggcaaag gtcttgagtg gtcagctac atttcctata gcggaggaac ttactataac   180
ccctcactta aaagccgctt cactatatca cgcgataata gcaagaacac cctctatctt   240
caaatgaact ctctgcgagc agaagacacc gccgtgtact attgcgctag agatagcgac   300
gacttcgggt tcgattattg ggacagggc acactggtga ccgtatcttc c             351
```

<210> SEQ ID NO 87
<211> LENGTH: 348
<212> TYPE: DNA
<213> ORGANISM: Artificial Sequence
<220> FEATURE:
<223> OTHER INFORMATION: Polynucleotide encoding heavy chain variable
      region of anti-BCMA antibody 5D5

<400> SEQUENCE: 87

```
gaggtccagt tgttggaaag cggtggtggt ttggttcaac caggcggtag cctcagactc    60
tcctgcgctg cctccgggtt tactttcagc gattatggac tgtcatgggt gcgtcaagct   120
cctggaaaag ggttggagtg ggtgagcctt atagacagca gtgggagtag cactttctac   180
gctgatagcg tgaaaggtag atttactatc tctcgtgata actccaagaa tacattgtat   240
cttcaaatga acagtctgag agctgaggac actgccgttt attattgtgc aaaggaacat   300
ggtcttttcg actcatgggg acagggaaca ctggtgaccg tatcttcc                348
```

<210> SEQ ID NO 88
<211> LENGTH: 348
<212> TYPE: DNA
<213> ORGANISM: Artificial Sequence
<220> FEATURE:
<223> OTHER INFORMATION: Polynucleotide encoding heavy chain variable
      region of anti-BCMA antibody 5B5

<400> SEQUENCE: 88

```
gaggtccagt tgttggaaag cggtggtggt ttggttcaac caggcggtag cctcagactc    60
tcctgcgctg cctccgggtt tactttctca gggcactatt ggtcctgggt ccgtcaggca   120
cctggtaagg gacttgaatg gtatctcaca gtttccggct ccggtggaga cactttttat   180
gcagacagcg ttaaggggcg ctttactata agtcgtgata attccaaaaa tactctctat   240
ctccaaatga actccctccg tgctgaagat accgctgtgt actactgcgc tcgaggtcac   300
tcagtcatgg acgtatgggg gcagggcaca ctggtgaccg tatcttcc                348
```

<210> SEQ ID NO 89
<211> LENGTH: 345
<212> TYPE: DNA
<213> ORGANISM: Artificial Sequence
<220> FEATURE:
<223> OTHER INFORMATION: Polynucleotide encoding heavy chain variable
      region of anti-BCMA antibody 2C6

<400> SEQUENCE: 89

```
gaggtccagt tgttggaaag cggtggtggt ttggttcaac caggcggtag cctcagactc    60
tcctgcgctg cctccgggtt tactttctct aactatggta tgtcatgggt ccgacaggca   120
ccagggaagg gactggaatg gtctcctct atagactata atggctctac atattacaac   180
ccaagtttga aaagccgttt tactatatct agggataaca gcaagaatac cctctacctc   240
```
caaatgaatt ctctgagagc agaggacact gctgtctact attgtgctaa agagcatggc    300
ctcttcgatt cttggggaca aggaacactc gtaacagtat cttcc                    345

<210> SEQ ID NO 90
<211> LENGTH: 351
<212> TYPE: DNA
<213> ORGANISM: Artificial Sequence
<220> FEATURE:
<223> OTHER INFORMATION: Polynucleotide encoding heavy chain variable
      region of anti-BCMA antibody 2F8

<400> SEQUENCE: 90
gaggtccagc tgctggagtc cggcggcggt cttgtgcaac aggcggaag tttgcgcttg      60 tcatgtgcag cttccgggtt cacctttagc aattacggaa tgagttgggt acggcaggct    120
cctggtaaag gtctgaatg ggtttccgaa atcatcccta tctttgacac ctcaaactat    180
gcccagaaat tccaaggtag gttcaccatt agcagggata actctaaaaa tacactttac    240
ctccagatga atagccttcg tgctgaggat actgccgtat attactgcgc taaaattcca    300
ggcaataggc atgactattg gggacaaggg acattggtga cggtcagctc a              351

<210> SEQ ID NO 91
<211> LENGTH: 348
<212> TYPE: DNA
<213> ORGANISM: Artificial Sequence
<220> FEATURE:
<223> OTHER INFORMATION: Polynucleotide encoding heavy chain variable
      region of anti-BCMA antibody 4H9

<400> SEQUENCE: 91
gaggtgcaac ttcttgaaag cggtggcggc ctggttcagc caggcggttc tctgcggttg      60
tcctgcgccg cctctggttt cacattctcc ggctattcca tgtcttgggt tcggcaagcc    120
cctggaaaag gacttgaatg ggtaagcagc atatatcata ctggttatac ctactataat    180
ccttctctta aatcaaggtt caccataagc agagataact caaagaatac actttacctg    240
caaatgaata gcctcagggc agaggacacc gctgtgtact attgtgctag gtataagagc    300
ggggccttcg atatctgggg ccagggaact ctcgtgaccg tttccagt                 348

<210> SEQ ID NO 92
<211> LENGTH: 363
<212> TYPE: DNA
<213> ORGANISM: Artificial Sequence
<220> FEATURE:
<223> OTHER INFORMATION: Polynucleotide encoding heavy chain variable
      region of anti-BCMA antibody 1H

<400> SEQUENCE: 92
gaggtacagc tcgttgaaag tggtggtggc ctcgtccagc caggcgggtc cctgaggctc      60
agctgtgctg cttccggttt tactttagt aattatgcta tgagttgggt tagacaggct     120
cccggaaaag gacttgagtg ggtcagcggc atctctcact ctggcagctc cacttattat    180
gccgattctg tgaaagggcg attcaccatc tcacgggaca actctaagaa caccttgtac    240
cttcagatga atagccttccg cgctgaagac acagcagtgt actactgcgc caaacatgtc    300
tacattatcg agttcgagtc tctggatata tggggccagg gtactcttgt tacagtctct    360
tca                                                                  363

<210> SEQ ID NO 93
<211> LENGTH: 363
<212> TYPE: DNA

<213> ORGANISM: Artificial Sequence
<220> FEATURE:
<223> OTHER INFORMATION: Polynucleotide encoding heavy chain variable
      region of anti-BCMA antibody 2G

<400> SEQUENCE: 93

```
gaggtgcagc ttgtcgaaag tgggggaggt ctggtgcaac ccggtggcag tctgaggctc    60
tcctgtgccg catctggctt tacctttagt aattacgcca tgagctgggt taggcaggca   120
cctggaaaag gtctggagtg gtttctgcc atcagcagtt cagggtcaac tatttattac   180
gccgattcag ttaagggtcg ttttactata gtagggata actcaaaaaa tacccttat    240 ctgcaaatga atagtctgag agctgaggat actgccgtct attattgtgc taaagcaggc   300
tattacgggt ctatttatgc tttcgactat tggggtcaag aactctggt cacagtgtcc   360 agt                                                                 363
```

<210> SEQ ID NO 94
<211> LENGTH: 363
<212> TYPE: DNA
<213> ORGANISM: Artificial Sequence
<220> FEATURE:
<223> OTHER INFORMATION: Polynucleotide encoding heavy chain variable
      region of anti-BCMA antibody 5G

<400> SEQUENCE: 94

```
gaggtacagc tcgttgaatc tggaggggga ctggtccagc ctggagggtc tcttcgtctg    60
tcatgcgcag catcagggtt cacattcagt aattacgcca tgtcctgggt acgtcaggca   120
cctgggaagg gtttggagtg ggtcagtggg atctcccaaa gcgggtcctc tacatattat   180
gcagactccg taaagggtcg gttcaccata agtagagaca acagtaagaa tactctctat   240
ctgcaaatga atagtttgag ggcagaggac actgctgtct actactgtgc taaacacgca   300
tatatcatag aatttgaatc aatggatatt tggggccagg gtactcttgt cactgtgagt   360
agc                                                                 363
```

<210> SEQ ID NO 95
<211> LENGTH: 354
<212> TYPE: DNA
<213> ORGANISM: Artificial Sequence
<220> FEATURE:
<223> OTHER INFORMATION: Polynucleotide encoding heavy chain variable
      region of anti-BCMA antibody 5C3

<400> SEQUENCE: 95

```
gaggtccagt tgttggaaag cggtggtggt ttggttcaac caggcggtag cctcagactc    60
tcctgcgctg cctccggtt tactttctca gactattata tacactgggt gcggcaggca   120
cctggcaagg gcctcgaatg ggtttctgct atatctggta gtggtggttc tacttactac   180
gccgatagtg tcaagggtcg atttactatt tcacgggata cagcaaaaa taccctctat   240 ctccaaatga actctctccg tgcagaggac actgctgttt actattgtgc tagtgatttg   300
ggtgacacaa catttgatag ctggggccag ggtacactcg taacagtatc ttcc         354
```

<210> SEQ ID NO 96
<211> LENGTH: 333
<212> TYPE: DNA
<213> ORGANISM: Artificial Sequence
<220> FEATURE:
<223> OTHER INFORMATION: Polynucleotide encoding light chain variable
      region of anti-BCMA antibody B58

<400> SEQUENCE: 96

```
cagtccgtgc tgacccagcc ccctccgcc tccggcaccc cggccagcg ggtgaccatc      60
tcctgctccg gctcctcctc caacatcggc tccaactccg tgtcctggta ccagcagctg    120
cccggcaccg cccccaagct gctgatctac gccgactcca gcggccctc cggcgtgccc     180
gaccggttct ccggctccaa gtccggcacc tccgcctccc tggccatctc cggcctgcgg    240
tccgaggacg aggccgacta ctactgcggc tcctgggact actccctgtc cggctacgtg    300
ttcggcggcg gcaccaagct gaccgtgctg ggc                                 333
```

<210> SEQ ID NO 97
<211> LENGTH: 321
<212> TYPE: DNA
<213> ORGANISM: Artificial Sequence
<220> FEATURE:
<223> OTHER INFORMATION: Polynucleotide encoding light chain variable
      region of anti-BCMA antibody 5A6

<400> SEQUENCE: 97

```
caatctgtcc ttacacagcc tccaagcgca agcggcaccc ccggacaaag ggtaacaata    60
tcatgccagg gggattctct tcgcagctat acgtgaattg gtatcagca gttgcccggc     120
actgccccca aactttgat atacgatcac tccaagcgcc ccacaggagt gcctgatagg     180
ttcagcggat ctaagtctgg aacatccgct tctttggcaa tctctgggct gcgaagtgag    240
gacgaggcag actactactg ccagtcttat gacagctcta ctgtagtctt cggaggcggt    300
acaaaactga cagtgctcgg t                                              321
```

<210> SEQ ID NO 98
<211> LENGTH: 324
<212> TYPE: DNA
<213> ORGANISM: Artificial Sequence
<220> FEATURE:
<223> OTHER INFORMATION: Polynucleotide encoding light chain variable
      region of anti-BCMA antibody 5D5

<400> SEQUENCE: 98

```
gaaatagtac ttacacagtc ccctggaact ctgtcacttt ccctggggga gcgagctaca    60
ctgagctgta aagcctcaca ggacatagac gatgacatca actggtatca gcaaaaacct    120
ggacaagctc cacgtctcct gatttacgat gcatcactta gggccacagg aattcctgat    180
aggttctctg gtagcggcag tggaaccgat tttaccctca caatatctcg acttgaacca    240
gaagatttcg ccgtttatta ctgtcagcag tcccttagga cccccattac attcggccag    300
gggacaaaac tggagataaa gcgt                                           324
```

<210> SEQ ID NO 99
<211> LENGTH: 324
<212> TYPE: DNA
<213> ORGANISM: Artificial Sequence
<220> FEATURE:
<223> OTHER INFORMATION: Polynucleotide encoding light chain variable
      region of anti-BCMA antibody 5B5

<400> SEQUENCE: 99

```
gaaatagtac ttacacagtc ccctggaact ctgtcacttt ccctggggga gcgagctaca    60
ctgagctgtc gtgccagcca gggcattgat agttacgtgg catggtatca gcagaagccc    120
ggccaggctc caaggctgtt gatttacgat gcatcattgc gagccaccgg atacctgac    180
cgtttctccg gcagtggctc cgggacagac tttacccttac ctatctcacg tctcgagcca    240
```
gaagactttg cagtgtatta ttgccaacaa tacaacagtt ggcctataac cttcggccag    300
gggacaaaac tggagataaa gcgt                                           324

<210> SEQ ID NO 100
<211> LENGTH: 324
<212> TYPE: DNA
<213> ORGANISM: Artificial Sequence
<220> FEATURE:
<223> OTHER INFORMATION: Polynucleotide encoding light chain variable
      region of anti-BCMA antibody 2C6

<400> SEQUENCE: 100
gaaatcgttc tcactcaatc ccctggcacc ctctccttga gccctggtga gcgcgcaact    60
ctgtcatgtc gggtcagtca aagcattagc agctacttga attggtacca gcagaaacct   120
gggcaggcac cccgactgct tatatatgat gcaagcactc gagccatagg cattcccgac   180
agattttctg ggagtggcag tggtacagat tttactttga caatctcaag attggagccc   240
gaagattttg ctgtctatta ctgtcaacaa gtaaattcct atcccataac tttcggacaa   300
gggaccaagg tcgagatcaa aaga                                           324

<210> SEQ ID NO 101
<211> LENGTH: 315
<212> TYPE: DNA
<213> ORGANISM: Artificial Sequence
<220> FEATURE:
<223> OTHER INFORMATION: Polynucleotide encoding light chain variable
      region of anti-BCMA antibody 2F8

<400> SEQUENCE: 101
cagagcgtac ttacccaacc tcccagtgca agcggaaccc ccggacagag agtcaccatt    60
tcctgtacca ggatgcagag gcagtctgac tggtatcaac agctgccagg aaccgcccct   120
aaactcctca tatacgacaa caataagcgc ccactcggag tccccgatag gttcagtggc   180
tccaagtctg ggactagtgc ttcactcgct atatctggcc ttcgatctga ggacgaagca   240
gattattatt gccagagtta cgactctaat gcttatgtcg tgttcggagg cgggaccaaa   300
ttgacagtcc ttggt                                                    315

<210> SEQ ID NO 102
<211> LENGTH: 324
<212> TYPE: DNA
<213> ORGANISM: Artificial Sequence
<220> FEATURE:
<223> OTHER INFORMATION: Polynucleotide encoding light chain variable
      region of anti-BCMA antibody 4H9

<400> SEQUENCE: 102
gagattgtac tgactcaatc tcctggcacc ctgtctctta gcccaggtga aagggctacc    60
ctctcttgca gggcatccca atctgtctcc cggaacctgg catggtacca acaaaaaccc   120
ggtcaagcac ctcgactcct gatctacggc gtctcctctc gcgcaaccgg cattcccgac   180
cgtttctctg gtcagggtc aggtactgat tcactttga caattagtcg gcttgaacct    240
gaggattttg ccgtatatta ctgtcagcaa tacggcagtt ccccccaac attcgggcag   300 gggacaaagg ttgaaattaa acgc                                          324

<210> SEQ ID NO 103
<211> LENGTH: 324
<212> TYPE: DNA
<213> ORGANISM: Artificial Sequence
<220> FEATURE:
<223> OTHER INFORMATION: Polynucleotide encoding light chain variable
      region of anti-BCMA antibody 1H

<400> SEQUENCE: 103
gacattcaga tgactcagag tccctcatcc ctgtcagcat cagtgggcga ccgagtcacc      60
atcacctgtc gcgcctcaca aagcatctca aattggctca actggtacca acaaaagcca     120
ggaaaagcac ccaagctgtt gatctatgcc gcatcaagtc tgcaatcagg tgttccttca     180
aggttctcag gtagtgggag tggaaccgat tttaccttga caataagctc cttgcagccc     240
gaggattttg ccacttatta ttgccaacaa agttatagca ccccttggac cttcgggcaa     300
ggaaccaagg tggaaattaa gcgg                                             324

<210> SEQ ID NO 104
<211> LENGTH: 324
<212> TYPE: DNA
<213> ORGANISM: Artificial Sequence
<220> FEATURE:
<223> OTHER INFORMATION: Polynucleotide encoding light chain variable
      region of anti-BCMA antibody 2G

<400> SEQUENCE: 104
gatatacaaa tgactcaaag cccctcaagc cttagtgcca gcgttggcga tcgggttact      60
ataacatgtc gggcctctca gtctatatcc tcctacctca actggtatca acaaaaacca     120
ggcaaagccc ccaaactttt gatttacgcc acctctcgac tccaatcagg cgtccctagt     180
agattcagcg gtccggttc cggtactgat ttcacccctca ctatatcttc cctccaacct     240
gaagattttg ctacctacta ctgccagcaa tcatcctcct cccttggac ttttggtcaa      300 gggacaaaag ttgaaatcaa acgt                                             324

<210> SEQ ID NO 105
<211> LENGTH: 324
<212> TYPE: DNA
<213> ORGANISM: Artificial Sequence
<220> FEATURE:
<223> OTHER INFORMATION: Polynucleotide encoding light chain variable
      region of anti-BCMA antibody 5G

<400> SEQUENCE: 105
gacattcaaa tgactcaatc acccagctcc ctgagtgcct ctgtaggtga tcgagttact      60
attacctgtc gcgccagtca agtatctct aactggctta attggtatca acagaagcca      120
ggaaaagctc ctaagctcct tatatatgca gcttcctccc tgcagagcgg tgtgccttct     180
cgcttctcag gtctggttc aggaaccgac ttcacattga ctattagcag cctgcagccc      240
gaagattttg ctacatatta ttgtcaacag tcatatagca ccccctggac tttcggacag     300
ggaacaaaag ttgaaatcaa acgc                                             324

<210> SEQ ID NO 106
<211> LENGTH: 327
<212> TYPE: DNA
<213> ORGANISM: Artificial Sequence
<220> FEATURE:
<223> OTHER INFORMATION: Polynucleotide encoding light chain variable
      region of anti-BCMA antibody 5C3

<400> SEQUENCE: 106
gaaatagtac ttacacagtc ccctggaact ctgtcacttt cccctgggga gcagagctaca     60 ctgagctgtc aagccagcga cgatatttca aactacttga attggtatca acaaaaacct    120
gggcaagcac cccggctcct tatatatggt gtttctaacc gtgccagtgg aatcccagac        180
cgcttttccg gatcaggtag tgggactgat tcacactca  caattagtag gttggaacca       240
gaagacttcg ctgtctacta ctgtcaacag tcctactcta ctccaccaat tacattcggc       300
caggggacaa aactggagat aaagcgt                                            327

```
<210> SEQ ID NO 107
<211> LENGTH: 107
<212> TYPE: PRT
<213> ORGANISM: Artificial Sequence
<220> FEATURE:
<223> OTHER INFORMATION: Mutant for Light chain variable region of SEQ
      ID NO: 17

<400> SEQUENCE: 107
```

Gln Ser Val Leu Thr Gln Pro Pro Ser Ala Ser Gly Thr Pro Gly Gln
1               5                   10                  15

Arg Val Thr Ile Ser Cys Gln Gly Glu Ser Leu Arg Ser Tyr Tyr Val
            20                  25                  30

Asn Trp Tyr Gln Gln Leu Pro Gly Thr Ala Pro Lys Leu Leu Ile Tyr
        35                  40                  45

Asp His Ser Lys Arg Pro Thr Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Gln Ser Tyr Asp Ser Ser Thr Val Val
                85                  90                  95

Phe Gly Gly Gly Thr Lys Leu Thr Val Leu Gly
            100                 105

```
<210> SEQ ID NO 108
<211> LENGTH: 107
<212> TYPE: PRT
<213> ORGANISM: Artificial Sequence
<220> FEATURE:
<223> OTHER INFORMATION: Mutant for Light chain variable region of SEQ
      ID NO: 17

<400> SEQUENCE: 108
```

Gln Ser Val Leu Thr Gln Pro Pro Ser Ala Ser Gly Thr Pro Gly Gln
1               5                   10                  15

Arg Val Thr Ile Ser Cys Gln Gly Asp Ala Leu Arg Ser Tyr Tyr Val
            20                  25                  30

Asn Trp Tyr Gln Gln Leu Pro Gly Thr Ala Pro Lys Leu Leu Ile Tyr
        35                  40                  45

Asp His Ser Lys Arg Pro Thr Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Gln Ser Tyr Asp Ser Ser Thr Val Val
                85                  90                  95

Phe Gly Gly Gly Thr Lys Leu Thr Val Leu Gly
            100                 105

```
<210> SEQ ID NO 109
<211> LENGTH: 107
<212> TYPE: PRT
<213> ORGANISM: Artificial Sequence
```

```
<220> FEATURE:
<223> OTHER INFORMATION: Mutant for Light chain variable region of SEQ
      ID NO: 17

<400> SEQUENCE: 109

Gln Ser Val Leu Thr Gln Pro Pro Ser Ala Ser Gly Thr Pro Gly Gln
1               5                   10                  15

Arg Val Thr Ile Ser Cys Gln Gly Asp Ser Leu Arg Ser Tyr Tyr Val
            20                  25                  30

Asn Trp Tyr Gln Gln Leu Pro Gly Thr Ala Pro Lys Leu Leu Ile Tyr
        35                  40                  45

Asp His Ser Lys Arg Pro Thr Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Gln Ser Tyr Glu Ser Ser Thr Val Val
                85                  90                  95

Phe Gly Gly Gly Thr Lys Leu Thr Val Leu Gly
            100                 105

<210> SEQ ID NO 110
<211> LENGTH: 107
<212> TYPE: PRT
<213> ORGANISM: Artificial Sequence
<220> FEATURE:
<223> OTHER INFORMATION: Mutant for Light chain variable region of SEQ
      ID NO: 17

<400> SEQUENCE: 110

Gln Ser Val Leu Thr Gln Pro Pro Ser Ala Ser Gly Thr Pro Gly Gln
1               5                   10                  15

Arg Val Thr Ile Ser Cys Gln Gly Asp Ser Leu Arg Ser Tyr Tyr Val
            20                  25                  30

Asn Trp Tyr Gln Gln Leu Pro Gly Thr Ala Pro Lys Leu Leu Ile Tyr
        35                  40                  45

Asp His Ser Lys Arg Pro Thr Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Gln Ser Tyr Asp Ala Ser Thr Val Val
                85                  90                  95

Phe Gly Gly Gly Thr Lys Leu Thr Val Leu Gly
            100                 105

<210> SEQ ID NO 111
<211> LENGTH: 107
<212> TYPE: PRT
<213> ORGANISM: Artificial Sequence
<220> FEATURE:
<223> OTHER INFORMATION: Mutant for Light chain variable region of SEQ
      ID NO: 17

<400> SEQUENCE: 111

Gln Ser Val Leu Thr Gln Pro Pro Ser Ala Ser Gly Thr Pro Gly Gln
1               5                   10                  15

Arg Val Thr Ile Ser Cys Gln Gly Glu Ser Leu Arg Ser Tyr Tyr Val
            20                  25                  30

Asn Trp Tyr Gln Gln Leu Pro Gly Thr Ala Pro Lys Leu Leu Ile Tyr
        35                  40                  45
```

```
Asp His Ser Lys Arg Pro Thr Gly Val Pro Asp Arg Phe Ser Gly Ser
        50                  55                  60

Lys Ser Gly Thr Ser Ala Ser Leu Ala Ile Ser Gly Leu Arg Ser Glu
 65                  70                  75                  80

Asp Glu Ala Asp Tyr Tyr Cys Gln Ser Tyr Glu Ser Ser Thr Val Val
                 85                  90                  95

Phe Gly Gly Gly Thr Lys Leu Thr Val Leu Gly
                100                 105
```

<210> SEQ ID NO 112
<211> LENGTH: 107
<212> TYPE: PRT
<213> ORGANISM: Artificial Sequence
<220> FEATURE:
<223> OTHER INFORMATION: Mutant for Light chain variable region of SEQ
      ID NO: 17

<400> SEQUENCE: 112

```
Gln Ser Val Leu Thr Gln Pro Pro Ser Ala Ser Gly Thr Pro Gly Gln
 1               5                  10                  15

Arg Val Thr Ile Ser Cys Gln Gly Glu Ser Leu Arg Ser Tyr Tyr Val
             20                  25                  30

Asn Trp Tyr Gln Gln Leu Pro Gly Thr Ala Pro Lys Leu Leu Ile Tyr
             35                  40                  45

Asp His Ser Lys Arg Pro Thr Gly Val Pro Asp Arg Phe Ser Gly Ser
        50                  55                  60

Lys Ser Gly Thr Ser Ala Ser Leu Ala Ile Ser Gly Leu Arg Ser Glu
 65                  70                  75                  80

Asp Glu Ala Asp Tyr Tyr Cys Gln Ser Tyr Asp Ala Ser Thr Val Val
                 85                  90                  95

Phe Gly Gly Gly Thr Lys Leu Thr Val Leu Gly
                100                 105
```

<210> SEQ ID NO 113
<211> LENGTH: 107
<212> TYPE: PRT
<213> ORGANISM: Artificial Sequence
<220> FEATURE:
<223> OTHER INFORMATION: Mutant for Light chain variable region of SEQ
      ID NO: 17

<400> SEQUENCE: 113

```
Gln Ser Val Leu Thr Gln Pro Pro Ser Ala Ser Gly Thr Pro Gly Gln
 1               5                  10                  15

Arg Val Thr Ile Ser Cys Gln Gly Asp Ala Leu Arg Ser Tyr Tyr Val
             20                  25                  30

Asn Trp Tyr Gln Gln Leu Pro Gly Thr Ala Pro Lys Leu Leu Ile Tyr
             35                  40                  45

Asp His Ser Lys Arg Pro Thr Gly Val Pro Asp Arg Phe Ser Gly Ser
        50                  55                  60

Lys Ser Gly Thr Ser Ala Ser Leu Ala Ile Ser Gly Leu Arg Ser Glu
 65                  70                  75                  80

Asp Glu Ala Asp Tyr Tyr Cys Gln Ser Tyr Glu Ser Ser Thr Val Val
                 85                  90                  95

Phe Gly Gly Gly Thr Lys Leu Thr Val Leu Gly
                100                 105
```

<210> SEQ ID NO 114
<211> LENGTH: 107

```
<212> TYPE: PRT
<213> ORGANISM: Artificial Sequence
<220> FEATURE:
<223> OTHER INFORMATION: Mutant for Light chain variable region of SEQ
      ID NO: 17

<400> SEQUENCE: 114

Gln Ser Val Leu Thr Gln Pro Pro Ser Ala Ser Gly Thr Pro Gly Gln
1               5                   10                  15

Arg Val Thr Ile Ser Cys Gln Gly Asp Ala Leu Arg Ser Tyr Tyr Val
            20                  25                  30

Asn Trp Tyr Gln Gln Leu Pro Gly Thr Ala Pro Lys Leu Leu Ile Tyr
        35                  40                  45

Asp His Ser Lys Arg Pro Thr Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Gln Ser Tyr Asp Ala Ser Thr Val Val
                85                  90                  95

Phe Gly Gly Gly Thr Lys Leu Thr Val Leu Gly
            100                 105

<210> SEQ ID NO 115
<211> LENGTH: 108
<212> TYPE: PRT
<213> ORGANISM: Artificial Sequence
<220> FEATURE:
<223> OTHER INFORMATION: Mutant for Light chain variable region of SEQ
      ID NO: 18

<400> SEQUENCE: 115

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Asn Asp
            20                  25                  30

Ile Asn Trp Tyr Gln Gln Lys Pro Gly Gln Ala Pro Arg Leu Leu Ile
        35                  40                  45

Tyr Asp Ala Ser Leu Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Leu Arg Thr Pro Ile
                85                  90                  95

Thr Phe Gly Gln Gly Thr Lys Leu Glu Ile Lys Arg
            100                 105

<210> SEQ ID NO 116
<211> LENGTH: 108
<212> TYPE: PRT
<213> ORGANISM: Artificial Sequence
<220> FEATURE:
<223> OTHER INFORMATION: Mutant for Light chain variable region of SEQ
      ID NO: 18

<400> SEQUENCE: 116

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Glu Asp
            20                  25                  30
```

```
Ile Asn Trp Tyr Gln Gln Lys Pro Gly Gln Ala Pro Arg Leu Leu Ile
        35                  40                  45

Tyr Asp Ala Ser Leu Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Ser Leu Arg Thr Pro Ile
                 85                  90                  95

Thr Phe Gly Gln Gly Thr Lys Leu Glu Ile Lys Arg
                100                 105
```

<210> SEQ ID NO 117
<211> LENGTH: 108
<212> TYPE: PRT
<213> ORGANISM: Artificial Sequence
<220> FEATURE:
<223> OTHER INFORMATION: Mutant for Light chain variable region of SEQ
      ID NO: 18

<400> SEQUENCE: 117

```
Glu Ile Val Leu Thr Gln Ser Pro Gly Thr Leu Ser Leu Ser Pro Gly
 1               5                  10                  15

Glu Arg Ala Thr Leu Ser Cys Lys Ala Ser Gln Asp Ile Asp Ala Asp
                 20                  25                  30

Ile Asn Trp Tyr Gln Gln Lys Pro Gly Gln Ala Pro Arg Leu Leu Ile
        35                  40                  45

Tyr Asp Ala Ser Leu Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Ser Leu Arg Thr Pro Ile
                 85                  90                  95

Thr Phe Gly Gln Gly Thr Lys Leu Glu Ile Lys Arg
                100                 105
```

<210> SEQ ID NO 118
<211> LENGTH: 108
<212> TYPE: PRT
<213> ORGANISM: Artificial Sequence
<220> FEATURE:
<223> OTHER INFORMATION: Mutant for Light chain variable region of SEQ
      ID NO: 18

<400> SEQUENCE: 118

```
Glu Ile Val Leu Thr Gln Ser Pro Gly Thr Leu Ser Leu Ser Pro Gly
 1               5                  10                  15

Glu Arg Ala Thr Leu Ser Cys Lys Ala Ser Gln Asp Ile Asp Asp Ala
                 20                  25                  30

Ile Asn Trp Tyr Gln Gln Lys Pro Gly Gln Ala Pro Arg Leu Leu Ile
        35                  40                  45

Tyr Asp Ala Ser Leu Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Ser Leu Arg Thr Pro Ile
                 85                  90                  95

Thr Phe Gly Gln Gly Thr Lys Leu Glu Ile Lys Arg
                100                 105
```

```
<210> SEQ ID NO 119
<211> LENGTH: 108
<212> TYPE: PRT
<213> ORGANISM: Artificial Sequence
<220> FEATURE:
<223> OTHER INFORMATION: Mutant for Light chain variable region of SEQ
      ID NO: 18

<400> SEQUENCE: 119

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Asp Glu
            20                  25                  30

Ile Asn Trp Tyr Gln Gln Lys Pro Gly Gln Ala Pro Arg Leu Leu Ile
        35                  40                  45

Tyr Asp Ala Ser Leu Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Leu Arg Thr Pro Ile
                85                  90                  95

Thr Phe Gly Gln Gly Thr Lys Leu Glu Ile Lys Arg
            100                 105

<210> SEQ ID NO 120
<211> LENGTH: 11
<212> TYPE: PRT
<213> ORGANISM: Artificial Sequence
<220> FEATURE:
<223> OTHER INFORMATION: Mutant for Light chain CDR1 of SEQ ID NO: 57

<400> SEQUENCE: 120

Gln Gly Glu Ser Leu Arg Ser Tyr Tyr Val Asn
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Mutant for Light chain CDR1 of SEQ ID NO: 57

<400> SEQUENCE: 121

Gln Gly Asp Ala Leu Arg Ser Tyr Tyr Val Asn
1               5                   10

<210> SEQ ID NO 122
<211> LENGTH: 8
<212> TYPE: PRT
<213> ORGANISM: Artificial Sequence
<220> FEATURE:
<223> OTHER INFORMATION: Mutant for Light chain CDR3 of SEQ ID NO: 76

<400> SEQUENCE: 122

Gln Ser Tyr Glu Ser Ser Thr Val
1               5

<210> SEQ ID NO 123
<211> LENGTH: 8
<212> TYPE: PRT
<213> ORGANISM: Artificial Sequence
<220> FEATURE:
<223> OTHER INFORMATION: Mutant for Light chain CDR3 of SEQ ID NO: 76
```

```
<400> SEQUENCE: 123

Gln Ser Tyr Asp Ala Ser Thr Val
1               5

<210> SEQ ID NO 124
<211> LENGTH: 11
<212> TYPE: PRT
<213> ORGANISM: Artificial Sequence
<220> FEATURE:
<223> OTHER INFORMATION: Mutant for Light chain CDR1 of SEQ ID NO: 58

<400> SEQUENCE: 124

Lys Ala Ser Gln Asp Ile Asp Asn Asp Ile Asn
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Mutant for Light chain CDR1 of SEQ ID NO: 58

<400> SEQUENCE: 125

Lys Ala Ser Gln Asp Ile Asp Glu Asp Ile Asn
1               5                   10

<210> SEQ ID NO 126
<211> LENGTH: 11
<212> TYPE: PRT
<213> ORGANISM: Artificial Sequence
<220> FEATURE:
<223> OTHER INFORMATION: Mutant for Light chain CDR1 of SEQ ID NO: 58

<400> SEQUENCE: 126

Lys Ala Ser Gln Asp Ile Asp Ala Asp Ile Asn
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Mutant for Light chain CDR1 of SEQ ID NO: 58

<400> SEQUENCE: 127

Lys Ala Ser Gln Asp Ile Asp Asp Ala Ile Asn
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Mutant for Light chain CDR1 of SEQ ID NO: 58

<400> SEQUENCE: 128

Lys Ala Ser Gln Asp Ile Asp Asp Glu Ile Asn
1               5                   10
```

ANTI-BCMA ANTIBODY AND USE THEREOF

CROSS-REFERENCE TO RELATED APPLICATIONS

This application is a national phase application of PCT Application No. PCT/KR2019/007727, filed on Jun. 26, 2019, which claims the benefit and priority to Korean Patent Application No. 10-2018-0073320, filed Jun. 26, 2018. The entire disclosures of the applications identified in this paragraph are incorporated herein by references.

FIELD

The present disclosure relates to antibodies or antigen-binding fragments thereof that specifically bind to B-cell mutation antigen (BCMA) proteins, a method of preparing the same, and use thereof.

BACKGROUND

B-cell maturation antigen (BCMA) is a protein of about 20 KDa and belongs to the tumor necrosis factor receptor (TNFR). BCMA is known to be a ligand of B-cell activating factor belonging to the tumor necrosis factor family (BAFF) and a proliferation inducing ligand (APRIL). In pathological situations, BCMA is expressed in neoplastic plasma cells of patients with multiple myeloma (MM), and survival rates of patients with multiple myeloma are lower with higher BCMA expression (Moreaux et al., Eur J Haematol 2009; 83:119-129).

Multiple myeloma is a neoplastic disease caused by monoclonal proliferation of plasma cells. The initial treatment response rate has increased due to the development of drugs such as thalidomide, bortezomib, and lenalidomide, and the development of treatment methods. However, the survival period of patients with multiple myeloma has not been significantly improved. Recently, monoclonal antibodies targeting CD38 and CS-1/SLAMF7 have been approved by the FDA as treatments for multiple myeloma. However, the effect is insignificant in some groups including relapsed/refractory patients. In particular, it has been reported that CD38 is partially expressed on the surface of red blood cells as well as immune cells, including lymphocytes, and thus shows false positives in various pre-transfusion tests when an anti-CD38 antibody is treated. Therefore, there is a need to develop multiple therapeutic agents that have fewer side effects compared to existing drugs and have increased efficacy.

BCMA, which exhibits limited expression in normal cells and specific expression patterns in pathological conditions, is considered to be one of the major target candidates for treatments of multiple myeloma. Therefore, it is necessary to develop an antibody capable of specifically recognizing BCMA and inhibiting or regulating the function thereof.

DETAILED DESCRIPTION

Technical Problem

Provided is an antibody or an antigen-binding fragment thereof that specifically binds to B-cell mutation antigen (BCMA).

Provided is a pharmaceutical composition for the prevention or treatment of cancer associated with the activation or overproduction of BCMA.

Provided is a method of preparing an antibody or an antigen-binding fragment thereof that specifically binds to BCMA.

Provided is a method of preventing or treating cancer associated with the activation or overproduction of BCMA protein.

Solution to Problem

Provided is an antibody or an antigen-binding fragment thereof that includes: a heavy chain variable region including at least one amino acid sequence selected from the group consisting of SEQ ID NOs: 27 to 55;
a light chain variable region including at least one amino acid sequence selected from the group consisting of SEQ ID NOs: 56 to 84 and 120 to 128;
or the heavy chain variable region and the light chain variable region, wherein the antibody or the antigen-binding fragment thereof specifically binds to a B-cell maturation antigen (BCMA).

There are five types of heavy chains ($\gamma$, $\delta$, $\alpha$, $\mu$, and $\epsilon$). The type of heavy chain defines the class of antibody. Heavy chains $\alpha$ and $\gamma$ consist of approximately 450 amino acids, whereas heavy chains $\mu$ and $\epsilon$ consist of approximately 550 amino acids. Heavy chains have two regions, i.e., a variable region and a constant region.

The two types of light chain, $\lambda$ and $\kappa$, consist of approximately 211 to 217 amino acids. Each human antibody contains only one type of light chain. Light chains have a constant region and a variable region that are successive.

The variable region refers to a region of the antibody which binds to an antigen.

The heavy chain variable region may include: a complementarity-determining region-H1 (CDR-H1) including an amino acid sequence selected from the group consisting of SEQ ID. NOs: 27 to 34; a CDR-H2 including an amino acid sequence selected from SEQ ID NOs: 35 to 45; and a CDR-H3 including an amino acid sequence selected from SEQ ID NOs: 46 to 55. The term "complementarity-determining region (CDR)" refers to a site of the variable region of an antibody that imparts antigen-binding specificity. For example, the heavy chain variable region may include an amino acid sequence selected from the group consisting of SEQ ID NOs: 5 to 15.

The light chain variable region may include: a CDR-L1 including an amino acid sequence selected from the group consisting of SED ID NOs: 56 to 65, 120, 121, and 124 to 128; a CDR-L2 including an amino acid sequence selected from the group consisting of SEQ ID Nos: 66 to 74; and a CDR-L3 including an amino acid sequence selected from the group consisting of SEQ ID NO: 75 to 84, 122, and 123. For example, the light chain variable region may include an amino acid sequence selected from the group consisting of SEQ ID NOs: 16 to 26 and 107 to 119.

The antibody may be an antibody including: a CDR-H1 including an amino acid sequence consisting of SED ID NO: 27, a CDR-H2 including an amino acid sequence consisting of SEQ ID NO: 35, a CDR-H3 including an amino acid sequence consisting of SED ID NO: 46, a CDR-L1 including an amino acid sequence consisting of SED ID NO: 56, a CDR-L2 including an amino acid sequence consisting of SEQ ID NO: 66, and a CDR-L3 including an amino acid sequence consisting of SEQ ID NO: 75.

The antibody may be an antibody including: a CDR-H1 including an amino acid sequence consisting of SED ID NO: 28, a CDR-H2 including an amino acid sequence consisting of SEQ ID NO: 36; a CDR-H3 including an amino acid sequence consisting of SED ID NO: 47, a CDR-L1 including an amino acid sequence consisting of SED ID NO: 57, a CDR-L2 including an amino acid sequence consisting of SEQ ID NO: 67, and a CDR-L3 including an amino acid sequence consisting of SEQ ID NO: 76.

The antibody may be an antibody including: a CDR-H1 including an amino acid sequence consisting of SED ID NO: 29, a CDR-H2 including an amino acid sequence consisting of SEQ ID NO: 37, a CDR-H3 including an amino acid sequence consisting of SED ID NO: 48, a CDR-L1 including an amino acid sequence consisting of SED ID NO: 58, a CDR-L2 including an amino acid sequence consisting of SEQ ID NO: 68, and a CDR-L3 including an amino acid sequence consisting of SEQ ID NO: 77.

The antibody may be an antibody including: a CDR-H1 including an amino acid sequence consisting of SED ID NO: 30, a CDR-H2 including an amino acid sequence consisting of SEQ ID NO: 38, a CDR-H3 including an amino acid sequence consisting of SED ID NO: 49, a CDR-L1 including an amino acid sequence consisting of SED ID NO: 59, a CDR-L2 including an amino acid sequence consisting of SEQ ID NO: 68, and a CDR-L3 including an amino acid sequence consisting of SEQ ID NO: 78.

The antibody may be an antibody including: a CDR-H1 including an amino acid sequence consisting of SED ID NO: 31, a CDR-H2 including an amino acid sequence consisting of SEQ ID NO: 39, a CDR-H3 including an amino acid sequence consisting of SED ID NO: 48, a CDR-L1 including an amino acid sequence consisting of SED ID NO: 60, a CDR-L2 including an amino acid sequence consisting of SEQ ID NO: 69, and a CDR-L3 including an amino acid sequence consisting of SEQ ID NO: 79.

The antibody may be an antibody including: a CDR-H1 including an amino acid sequence consisting of SED ID NO: 31, a CDR-H2 including an amino acid sequence consisting of SEQ ID NO: 40, a CDR-H3 including an amino acid sequence consisting of SED ID NO: 50, a CDR-L1 including an amino acid sequence consisting of SED ID NO: 61, a CDR-L2 including an amino acid sequence consisting of SEQ ID NO: 70, and a CDR-L3 including an amino acid sequence consisting of SEQ ID NO: 80.

The antibody may be an antibody including: a CDR-H1 including an amino acid sequence consisting of SED ID NO: 32, a CDR-H2 including an amino acid sequence consisting of SEQ ID NO: 41, a CDR-H3 including an amino acid sequence consisting of SED ID NO: 51, a CDR-L1 including an amino acid sequence consisting of SED ID NO: 62, a CDR-L2 including an amino acid sequence consisting of SEQ ID NO: 71, and a CDR-L3 including an amino acid sequence consisting of SEQ ID NO: 81.

The antibody may be an antibody including: a CDR-H1 including an amino acid sequence consisting of SED ID NO: 33, a CDR-H2 including an amino acid sequence consisting of SEQ ID NO: 42, a CDR-H3 including an amino acid sequence consisting of SED ID NO: 52, a CDR-L1 including an amino acid sequence consisting of SED ID NO: 63, a CDR-L2 including an amino acid sequence consisting of SEQ ID NO: 72, and a CDR-L3 including an amino acid sequence consisting of SEQ ID NO: 82.

The antibody may be an antibody including: a CDR-H1 including an amino acid sequence consisting of SED ID NO: 33, a CDR-H2 including an amino acid sequence consisting of SEQ ID NO: 43, a CDR-H3 including an amino acid sequence consisting of SED ID NO: 53, a CDR-L1 including an amino acid sequence consisting of SED ID NO: 64, a CDR-L2 including an amino acid sequence consisting of SEQ ID NO: 73, and a CDR-L3 including an amino acid sequence consisting of SEQ ID NO: 83.

The antibody may be an antibody including: a CDR-H1 including an amino acid sequence consisting of SED ID NO: 33, a CDR-H2 including an amino acid sequence consisting of SEQ ID NO: 44, a CDR-H3 including an amino acid sequence consisting of SED ID NO: 54, a CDR-L1 including an amino acid sequence consisting of SED ID NO: 63, a CDR-L2 including an amino acid sequence consisting of SEQ ID NO: 72, and a CDR-L3 including an amino acid sequence consisting of SEQ ID NO: 82.

The antibody may be an antibody including: a CDR-H1 including an amino acid sequence consisting of SED ID NO: 34, a CDR-H2 including an amino acid sequence consisting of SEQ ID NO: 45, a CDR-H3 including an amino acid sequence consisting of SED ID NO: 55, a CDR-L1 including an amino acid sequence consisting of SED ID NO: 65, a CDR-L2 including an amino acid sequence consisting of SEQ ID NO: 74, and a CDR-L3 including an amino acid sequence consisting of SEQ ID NO: 84.

The antibody may be an antibody including: a CDR-H1 including an amino acid sequence consisting of SED ID NO: 28, a CDR-H2 including an amino acid sequence consisting of SEQ ID NO: 36, a CDR-H3 including an amino acid sequence consisting of SED ID NO: 47, a CDR-L1 including an amino acid sequence consisting of SED ID NO: 120, a CDR-L2 including an amino acid sequence consisting of SEQ ID NO: 67, and a CDR-L3 including an amino acid sequence consisting of SEQ ID NO: 76.

The antibody may be an antibody including: a CDR-H1 including an amino acid sequence consisting of SED ID NO: 28, a CDR-H2 including an amino acid sequence consisting of SEQ ID NO: 36, a CDR-H3 including an amino acid sequence consisting of SED ID NO: 47, a CDR-L1 including an amino acid sequence consisting of SED ID NO: 121, a CDR-L2 including an amino acid sequence consisting of SEQ ID NO: 67, and a CDR-L3 including an amino acid sequence consisting of SEQ ID NO: 76.

The antibody may be an antibody including: a CDR-H1 including an amino acid sequence consisting of SED ID NO: 28, a CDR-H2 including an amino acid sequence consisting of SEQ ID NO: 36, a CDR-H3 including an amino acid sequence consisting of SED ID NO: 47, a CDR-L1 including an amino acid sequence consisting of SED ID NO: 57, a CDR-L2 including an amino acid sequence consisting of SEQ ID NO: 67, and a CDR-L3 including an amino acid sequence consisting of SEQ ID NO: 122.

The antibody may be an antibody including: a CDR-H1 including an amino acid sequence consisting of SED ID NO: 28, a CDR-H2 including an amino acid sequence consisting of SEQ ID NO: 36, a CDR-H3 including an amino acid sequence consisting of SED ID NO: 47, a CDR-L1 including an amino acid sequence consisting of SED ID NO: 57, a CDR-L2 including an amino acid sequence consisting of SEQ ID NO: 67, and a CDR-L3 including an amino acid sequence consisting of SEQ ID NO: 123.

The antibody may be an antibody including: a CDR-H1 including an amino acid sequence consisting of SED ID NO: 28, a CDR-H2 including an amino acid sequence consisting of SEQ ID NO: 36, a CDR-H3 including an amino acid sequence consisting of SED ID NO: 47, a CDR-L1 including an amino acid sequence consisting of SED ID NO: 120, a CDR-L2 including an amino acid sequence consisting of SEQ ID NO: 67, and a CDR-L3 including an amino acid sequence consisting of SEQ ID NO: 122.

The antibody may be an antibody including: a CDR-H1 including an amino acid sequence consisting of SED ID NO:

28, a CDR-H2 including an amino acid sequence consisting of SEQ ID NO: 36, a CDR-H3 including an amino acid sequence consisting of SED ID NO: 47, a CDR-L1 including an amino acid sequence consisting of SED ID NO: 120, a CDR-L2 including an amino acid sequence consisting of SEQ ID NO: 67, and a CDR-L3 including an amino acid sequence consisting of SEQ ID NO: 123.

The antibody may be an antibody including: a CDR-H1 including an amino acid sequence consisting of SED ID NO: 28, a CDR-H2 including an amino acid sequence consisting of SEQ ID NO: 36, a CDR-H3 including an amino acid sequence consisting of SED ID NO: 47, a CDR-L1 including an amino acid sequence consisting of SED ID NO: 121, a CDR-L2 including an amino acid sequence consisting of SEQ ID NO: 67, and a CDR-L3 including an amino acid sequence consisting of SEQ ID NO: 122.

The antibody may be an antibody including: a CDR-H1 including an amino acid sequence consisting of SED ID NO: 28, a CDR-H2 including an amino acid sequence consisting of SEQ ID NO: 36, a CDR-H3 including an amino acid sequence consisting of SED ID NO: 47, a CDR-L1 including an amino acid sequence consisting of SED ID NO: 121, a CDR-L2 including an amino acid sequence consisting of SEQ ID NO: 67, and a CDR-L3 including an amino acid sequence consisting of SEQ ID NO: 123.

The antibody may be an antibody including: a CDR-H1 including an amino acid sequence consisting of SED ID NO: 29, a CDR-H2 including an amino acid sequence consisting of SEQ ID NO: 37, a CDR-H3 including an amino acid sequence consisting of SED ID NO: 48, a CDR-L1 including an amino acid sequence consisting of SED ID NO: 124, a CDR-L2 including an amino acid sequence consisting of SEQ ID NO: 68, and a CDR-L3 including an amino acid sequence consisting of SEQ ID NO: 77.

The antibody may be an antibody including: a CDR-H1 including an amino acid sequence consisting of SED ID NO: 29, a CDR-H2 including an amino acid sequence consisting of SEQ ID NO: 37, a CDR-H3 including an amino acid sequence consisting of SED ID NO: 48, a CDR-L1 including an amino acid sequence consisting of SED ID NO: 125, a CDR-L2 including an amino acid sequence consisting of SEQ ID NO: 68, and a CDR-L3 including an amino acid sequence consisting of SEQ ID NO: 77.

The antibody may be an antibody including: a CDR-H1 including an amino acid sequence consisting of SED ID NO: 29, a CDR-H2 including an amino acid sequence consisting of SEQ ID NO: 37, a CDR-H3 including an amino acid sequence consisting of SED ID NO: 48, a CDR-L1 including an amino acid sequence consisting of SED ID NO: 126, a CDR-L2 including an amino acid sequence consisting of SEQ ID NO: 68, and a CDR-L3 including an amino acid sequence consisting of SEQ ID NO: 77.

The antibody may be an antibody including: a CDR-H1 including an amino acid sequence consisting of SED ID NO: 29, a CDR-H2 including an amino acid sequence consisting of SEQ ID NO: 37, a CDR-H3 including an amino acid sequence consisting of SED ID NO: 48, a CDR-L1 including an amino acid sequence consisting of SED ID NO: 127, a CDR-L2 including an amino acid sequence consisting of SEQ ID NO: 68, and a CDR-L3 including an amino acid sequence consisting of SEQ ID NO: 77.

The antibody may be an antibody including: a CDR-H1 including an amino acid sequence consisting of SED ID NO: 29, a CDR-H2 including an amino acid sequence consisting of SEQ ID NO: 37, a CDR-H3 including an amino acid sequence consisting of SED ID NO: 48, a CDR-L1 including an amino acid sequence consisting of SED ID NO: 128, a CDR-L2 including an amino acid sequence consisting of SEQ ID NO: 68, and a CDR-L3 including an amino acid sequence consisting of SEQ ID NO: 77.

The antibody including a light chain CDR including at least one amino acid sequence selected from SEQ ID NOs: 120 to 128 may have improved target antigen binding ability compared to the respective wild-type antibodies.

The B-cell maturation antigen (BCMA) may be a BCMA polypeptide or a fragment thereof. BCMA may be called tumor necrosis factor receptor superfamily member 17 (TNFRSF17), BCM, CD269, TNFRSF13A, or a TNF-receptor superfamily member 17. The BCMA polypeptide may include a human amino acid sequence of GenBank Accession No. NP_001183, or a mouse amino acid sequence of GenBank Accession No. NP_035738. The BCMA polypeptide may include a peptide of amino acid sequence encoded by a polynucleotide (human) of GenBank Accession No. NM_001192, or a polymucleotide (mouse) of GenBank Accession No. NM_011608. The fragment may be a polypeptide including partial amino acid sequence of BCMA polypeptide.

The antibody or the antigen-binding fragment thereof that specifically binds to BCMA may have affinity to a BCMA polypeptide or a fragment thereof. The antibody or the antigen-binding fragment thereof may have affinity to the extracellular domain of BCMA. The antibody or the antigen-binding fragment thereof may specifically bind to an amino acid from $1^{st}$ to $54^{th}$ amino acid sequences from the N terminal in SEQ ID NO: 1.

The antibody or the antigen-binding fragment thereof may inhibit binding of BCMA protein with a substance that specifically binds to BCMA protein. The substance that specifically binds to BCMA protein may also be referred to as a ligand, and for example, may be a B-cell activating factor belonging to the tumor necrosis factor family (BAFF), a proliferation Inducing ligand (APRIL), or a combination thereof.

The term "antibody" is interchangeably used with "immunoglobulin (Ig)." The whole antibody has a structure including two full-length light chains and two full-length heavy chains, which are connected by disulfide (SS) bonds. The antibody may be, for example, IgA, IgD, IgE, IgG, or IgM. The antibody may be a monoclonal antibody or a polyclonal antibody. The antibody may be an animal-derived antibody, a mouse-human chimeric antibody, a humanized antibody, or a human antibody.

The term "antigen-binding fragment" refers to a fragment of the whole immunoglobulin structure, which may be a part of a polypeptide including an antigen-binding site. For example, the antigen-binding fragment may be scFv, (scFv)$_2$, Fv, Fab, Fab', Fv F(ab')$_2$, or a combination thereof.

The antibody or the antigen-binding fragment thereof may be modified. For example, the antibody or the antigen-binding fragment thereof may be modified by conjugation or binding, glycosylation, deamination, tag attachment, or a combination thereof.

The antibody or the antigen-binding fragment may be conjugated with other drugs such as anti-cancer drug. For example, the antibody or the antigen-binding fragment thereof may be conjugated with horseradish peroxidase (HRP), alkaline phosphatase, hapten, biotin, streptavidin, a fluorescent material, a radioactive material, quantum dots, polyethylene glycol (PEG), a histidine tag, or a combination thereof. The fluorescent material may be ALEXA FLUOR®532, ALEXA FLUOR®546, ALEXA FLUOR®568, ALEXA FLUOR®680, ALEXA FLUOR®750, ALEXA FLUOR®790, or ALEXA FLUOR™350.

Provided is the pharmaceutical composition for prevention or treatment of cancer, including the antibody or the antigen-binding fragment thereof that specifically binds to BCMA.

The antibody, antigen-binding fragment, and BCMA are the same as described above.

The cancer may be a disease related to the activation or overexpression of BCMA. The cancer may be a solid cancer or a non-solid cancer. Solid cancers refer to the incidence of cancerous tumors in organs such as the liver, lung, breast, or skin. Non-solid cancers refer to cancers affecting the blood, and so are called blood cancer. The cancer may be multiple myeloma.

The term "prevention" refers to any act that suppresses or delays the onset of cancer by administration of the pharmaceutical composition. The term "treatment" refers to any act that alleviates or beneficially changes symptoms of cancer by administration of the pharmaceutical composition.

The pharmaceutical composition may include a pharmaceutically acceptable carrier. The carrier may be construed as meaning an excipient, a diluent, or an adjuvant. For example, the carrier may be selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, physiological saline, a buffer such as phosphate-buffered saline (PBS), methyl hydroxybenzoate, propyl hydroxybenzoate, talc, magnesium stearate, and mineral oil. The pharmaceutical composition may include a filler, an anti-coagulant, a lubricant, a wetting agent, a flavoring agent, an emulsifier, a preservative, or a combination thereof.

The pharmaceutical composition may be formulated in any form using any common method in the art. For example, the pharmaceutical composition may be formulated in oral dosage form (for example, powders, tablets, capsules, syrups, pills, or granules), or parenteral dosage form (for example, injection). The pharmaceutical composition may be prepared in formulation for systemic delivery, or in a formulation for local delivery.

The pharmaceutical composition may include the antibody or the antigen-binding fragment thereof, an anti-cancer drug, or a combination thereof in an effective amount. The term "effective amount" used herein refers to an amount sufficient to prevent or treat a disease related to activation or overexpression of ErbB3 protein when administered to an individual who needs such prevention or treatment. The effective amount may be appropriately selected depending on a selected cell or individual by one of ordinary skill in the art. For example, the effective amount may be determined depending on disease severity, a patient's age, body weight, health conditions, gender, a patient's drug sensitivity, administration duration, administration route, excretion rate, treatment duration, and other factors, including use of a drug in combination with or at the same time as the pharmaceutical composition, and other factors known in the medical field. The effective amount may be about 0.5 µg to about 2 g.

A dosage of the pharmaceutical composition may be, for example, about 0.001 mg/kg to about 100 mg/kg, for adults. The number of administrations may be, for example, once or multiple times a day, or once a week or in four weeks, or once or twelve times a week.

Provided is a method of prevention or treatment of a cancer, the method including administering, to an individual, an antibody or an antigen-binding fragment thereof that specifically bind to BCMA.

The antibody, antigen-binding fragment, BCMA, cancer, prevention, or treatment may be the same as described above.

The individual may be a mammal, for example, a human, cow, horse, pig, dog, sheep, goat, or cat. The individual may be an individual who suffers from a disease related to the activation or overexpression of BCMA or who is susceptible to the disease, which may be cancer.

For example, the antibody or the antigen-binding fragment thereof, an anti-cancer drug, or a combination thereof may be directly administered to the individual by any method, for example, by oral, intravenous, intramuscular, transdermal, mucosal, intranasal, intratracheal, or subcutaneous administration. The antibody or the antigen-binding fragment thereof, an anti-cancer drug, or a combination thereof may be administered systemically or locally. The antibody or the antigen-binding fragment thereof, an anti-cancer drug, or a combination thereof may be administered alone or together with a pharmaceutically active compound.

A dosage of the antibody or the antigen-binding fragment thereof, an anti-cancer drug, or a combination thereof may vary depending on a patient's condition, body weight, disease severity, drug formulation, administration route, and administration duration, and may be appropriately selected by one of ordinary skill in the art. For example, a dosage of the antibody or the antigen-binding fragment thereof, an anti-cancer drug, or a combination thereof may be about 0.001 mg/kg to about 100 mg/kg for adults. The number of administrations may be, for example, once or multiple times a day, or once a week or in four weeks, or once or twelve times a week.

Advantageous Effects of Disclosure

As described above, according to the one or more example embodiments, an antibody that specifically binds to BCMA or an antigen-binding fragment thereof, and use thereof, are provided. The antibody that specifically binds to BCMA or an antigen-binding fragment thereof may be effectively used to prevent or treat cancer.

DETAILED DESCRIPTION

Figure 1A:
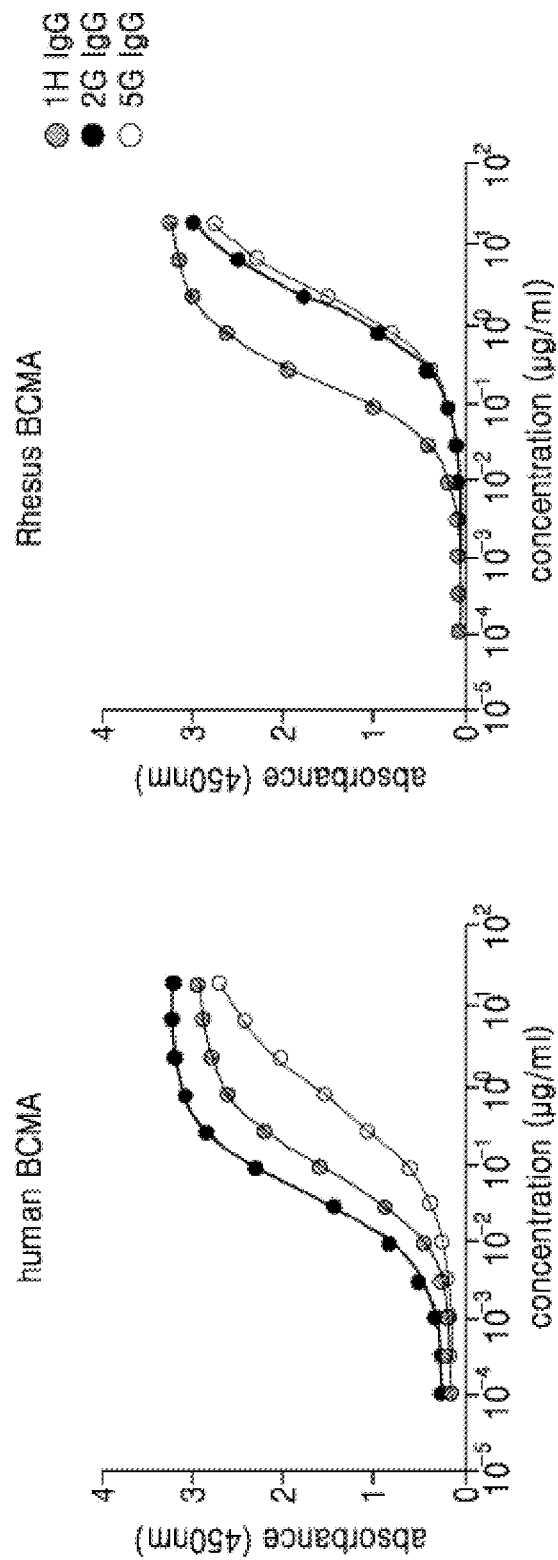
FIG. 1A is a graph showing results of measuring, by enzyme-linked immunosorbent assay (ELISA), the binding ability of antibodies 1H, 2G, and 5G to human B-cell maturation antigen (BCMA) or monkey BCMA.

One or more embodiments of the present disclosure will now be described in detail with reference to the following examples. However, these examples are only for illustrative purposes and are not intended to limit the scope of the one or more embodiments of the present disclosure.

Example 1. Preparation of Anti-BCMA Antibody

1. Preparation of Antigen

Antigens were prepared as follows for the preparation of anti-BCMA antibodies. Antigens containing amino acid residues 5-54, 1-51, 1-54, and 4-48, respectively, from the N-terminus of the amino acid sequence of human BCMA (GenBank Accession No. NP_001183.2, SEQ ID NO: 1) were used.

Specifically, an antigen containing amino acid residues 5-54 of human BCMA (GENSCRIPT®, Z02731) ("human BCMA (5-54)"); an antigen containing amino acid residues 1-51 of human BCMA (made in house, expressed in CHO cells) fused to the Fc region of the human IgG1 ("human BCMA-Fc (1-51)"); an antigen containing amino acid residues 1-51 of human BCMA fused to the Fc region and His tag to the C-terminus thereof (10620-H03H, Sino Biological Inc.) ("human BCMA-Fc/His (1-51)"); and an antigen containing amino acid residues 4-48 of human BCMA (made in house, expressed in HEK293 cells) fused to the Fc region ("human BCMA-Fc (4-48)") were prepared.

Human BCMA-Fc (4-48) was prepared as follows. Polynucleotides encoding amino acid residues 4-48 of human BCMA were cloned into pAB1-Fc which is an animal cell expression vector including a CMV promoter. The cloned vector was transformed into HEK293E cells, and human BCMA-Fc (4-48) was purified using Protein A affinity chromatography. Human BCMA-Fc (1-51) was prepared in the same manner as described above.

In addition, in order to confirm cross-reactivity between species, monkey (Rhesus) BCMA (1-53) (90103-C02H, Sino Biological Inc.), mouse BCMA (1-49) (50076-M01H, Sino Biological Inc.), and rat BCMA (1-49) (80156-R01H, Sino Biological Inc.), in which the Fc region of human IgG1 is fused, were used. The amino acid sequences of monkey BCMA (1-53), mouse BCMA, and rat BCMA are shown in Table 1 below.

TABLE 1

| Antigen | Amino acid sequence (N->C) | SEQ ID NO: |
| --- | --- | --- |
| Monkey BCMA (1-53) | MLQMARQCSQNEYFDSLLHDCKPCQLRCSS TPPLTCQRYCNASMTNSVKGMNA | 2 |
| Mouse BCMA (1-49) | MAQQCFHSEYFDSLLHACKPCHLRCSNPPA TCQPYCDPSVTSSVKGTYT | 3 |
| Rat BCMA (1-49) | MAQRCFHSEYFDSLLHACKPCRLRCSNPPA PCQPYCDPSMTSSVRGTYT | 4 |

2. Library Phage Preparation and Phage-Display Panning

Human-derived single-chain fragment variable (ScFv) phage library cells (Mol. Cells OT, 225-235, Feb. 28, 2009), which are able to bind to various antigens, were prepared. The prepared phage library was infected with the helper phage, and then, phage packing was induced. Thereafter, the culture product was centrifuged at 4,500 rpm for 15 minutes at 4° C., and then, 4% (w/v) PEG 6000 (Fluka, 81253) and 3% (w/v) NaCl (Sigma, S7653) were added to the supernatant and dissolved well, followed by incubating on ice for 1 hour. The resultant product was centrifuged at 4° C. at 8,000 rpm for 20 minutes, pellets were suspended in PBS, and then centrifused again at 4° C. at 12,000 rpm for 10 minutes to obtain a supernatant containing a library phage. The obtained library phage was stored at 4° C. until use.

Panning was performed a total of three times in the following manner to screen for antibodies that are reactive to human BCMA or cross-reactive to human BCMA and monkey BCMA. 5 µg of the antigen prepared according to Example 1-1 was added to an immunotube (maxisorp 444202) and incubated at 4° C. for 16 hours to coat the surface of the test tube with a protein. The supernatant was removed therefrom, and bovine serum albumin (BSA) was added thereto to block nonspecific binding. $10^{12}$ CFU of the phage library of prepared according to Example 1.2 was mixed with 1.5% (w/v) BSA, and the mixture was added to the target protein-coated immunoassay tube and reacted at 37° C. for 1 hour to allow a BCMA-specific phage to bind to the target protein. Subsequently, after multiple washing with a PBS-T (phosphate buffered saline including 0.05% (v/v) Tween 20) solution, phages bound to BCMA were recovered by using a 100 mM triethylamine solution. The recovered phages were neutralized with 1M Tris buffer (pH 7.4), and then, K12 ER2738 *Escherichia coli* was infected therewith, and the phages were recovered again. This cycle was repeatedly performed 4 times for phage panning. As the panning round progressed, the number of washes using PBS-T was increased to amplify and concentrate the antigen-specific phage.

3. Single Clone Phage Antibody Screening

A single clone phase antibody screening procedure was performed to select, from a phage pool, a monoclonal antibody that specifically binds to BCMA.

Specifically, the phage pool obtained according to Example 1.2 was sequentially diluted, and cultured on a solid medium containing LB-tetracycline/cabenicillin to obtain single colonies. Each colony was cultured on a 96-deep well plate so that OD600 was from 0.5 to 0.7. 20 MOI of helper phage was added to the culture, and reacted at 37° C. for 1 hour. Thereafter, kanamycin was added to the culture and incubated overnight at 30° C. On the next day, the culture was centrifuged and the supernatant thereof was collected, and then, ELISA was performed to select BCMA-specific phages. Each well of the ELISA plate was coated with 100 ng of recombinant BCMA, and then coated with 3% BSA to prevent nonspecific binding. Thereafter, the plate was washed with PBS. The prepared single clone phages was added to each well and incubated at 37° C. for 1 hour, and the plate was washed three times with PBS-T. ELISA was performed using horseradish peroxidase (HRP) conjugated anti-hemagglutinin (HA) antibody and tetramethylbenzidine (TMB, Sigma, T0440). Clones, which have an absorbance of 0.5 or more at a wavelength of 450 nm and also an absorbance of at least 5 times greater than that of the control which is anti-HA HRP alone, were selected. Eleven antibody clones (B58, 5A6, 5D5, 5B5, 2C6, 2F8, 4H9, 1H, 2G, 5G, and 5C3), which specifically bind to human BCMA, were selected.

From the nucleotide sequences encoding the selected antibodies, the amino acid sequences of the heavy chain variable region (SEQ ID NOs: 5 to 15) and the amino acid sequences of the light chain variable region (SEQ ID NOs: 16 to 26) were analyzed, and complementarity-determining regions (CDR) were determined according to Kabat definition. The determined CDR amino acid sequences (N→C) of the heavy chains and light chains are shown in Tables 2 and 3, respectively.

TABLE 2

| Antibody | CDR-H1 | CDR-H2 | CDR-H3 |
|---|---|---|---|
| B58 | NYDMS (SEQ ID NO: 27) | WIYPSDSSIYYADSVKG (SEQ ID NO: 35) | RGPFANKYRQFDY (SEQ ID NO: 46) |
| 5A6 | NYGVH (SEQ ID NO: 28) | YISYSGGTYYNPSLKS (SEQ ID NO: 36) | RDSDDFGFDY (SEQ ID NO: 47) |
| 5D5 | DYGLS (SEQ ID NO: 29) | LIDSSGSSTFYADSVKG (SEQ ID NO: 37) | KEHGLFDS (SEQ ID NO: 48) |
| 5B5 | GHYWS (SEQ ID NO: 30) | TVSGSGGDTFYADSVKG (SEQ ID NO: 38) | RGHSVMDV (SEQ ID NO: 49) |
| 2C6 | NYGMS (SEQ ID NO: 31) | SIDYNGSTYYNPSLKS (SEQ ID NO: 39) | KEHGLFDS (SEQ ID NO: 48) |
| 2F8 | NYGMS (SEQ ID NO: 31) | EIIPIFDTSNYAQKFQG (SEQ ID NO: 40) | KIPGNRHDY (SEQ ID NO: 50) |
| 4H9 | GYSMS (SEQ ID NO: 32) | SIYHTGYTYYNPSLKS (SEQ ID NO: 41) | RYKSGAFDI (SEQ ID NO: 51) |
| 1H | NYAMS (SEQ ID NO: 33) | GISHSGSSTYYADSVKG (SEQ ID NO: 42) | HVYIIEFESLDI (SEQ ID NO: 52) |
| 2G | NYAMS (SEQ ID NO: 33) | AISSSGSTIYYADSVKG (SEQ ID NO: 43) | AGYYGSIYAFDY (SEQ ID NO: 53) |
| 5G | NYAMS (SEQ ID NO: 33) | GISQSGSSTYYADSVKG (SEQ ID NO: 44) | HAYIIEFESMDI (SEQ ID NO: 54) |
| 5C3 | DYYIH (SEQ ID NO: 34) | AISGSGGSTYYADSVKG (SEQ ID NO: 45) | SDLGDTTFDS (SEQ ID NO: 55) |

TABLE 3

| Antibody | CDR-L1 | CDR-L2 | CDR-L3 |
|---|---|---|---|
| B58 | SGSSSNIGSNSVS (SEQ ID NO: 56) | ADSKRPS (SEQ ID NO: 66) | GSWDYSLSGYV (SEQ ID NO: 75) |
| 5A6 | QGDSLRSYYVN (SEQ ID NO: 57) | DHSKRPT (SEQ ID NO: 67) | QSYDSSTV (SEQ ID NO: 76) |
| 5D5 | KASQDIDDDIN (SEQ ID NO: 58) | DASLRAT (SEQ ID NO: 68) | QQSLRTPI (SEQ ID NO: 77) |

TABLE 3-continued

| Antibody | CDR-L1 | CDR-L2 | CDR-L3 |
|---|---|---|---|
| 5B5 | RASQGIDSYVA (SEQ ID NO: 59) | DASLRAT (SEQ ID NO: 68) | QQYNSWPI (SEQ ID NO: 78) |
| 2C6 | RVSQSISSYLN (SEQ ID NO: 60) | DASTRAI (SEQ ID NO: 69) | QQVNSYPIT (SEQ ID NO: 79) |
| 2F8 | TRMQRQSD (SEQ ID NO: 61) | DNNKRPL (SEQ ID NO: 70) | QSYDSNAYVV (SEQ ID NO: 80) |
| 4H9 | RASQSVSRNLA (SEQ ID NO: 62) | GVSS (SEQ ID NO: 71) | QQYGSSPPT (SEQ ID NO: 81) |
| 1H | RASQSISNWLN (SEQ ID NO: 63) | AASSLQS (SEQ ID NO: 72) | QQSYSTPWT (SEQ ID NO: 82) |
| 2G | RASQSISSYLN (SEQ ID NO: 64) | ATSRLQS (SEQ ID NO: 73) | QQSSSFPWT (SEQ ID NO: 83) |
| 5G | RASQSISNWLN (SEQ ID NO: 63) | AASSLQS (SEQ ID NO: 72) | QQSYSTPWT (SEQ ID NO: 82) |
| 5C3 | QASDDISNYLN (SEQ ID NO: 65) | GVSNRAS (SEQ ID NO: 74) | QQSYSTPPI (SEQ ID NO: 84) |

Nucleotide sequences encoding heavy chain variable regions and nucleotide sequences encoding light chain variable regions are shown in Table 4 below.

TABLE 4

| Antibody | Nucleotide sequences encoding heavy chain variable regions | nucleotide sequences encoding light chain variable regions |
|---|---|---|
| B58 | SEQ ID NO: 85 | SEQ ID NO: 96 |
| 5A6 | SEQ ID NO: 86 | SEQ ID NO: 97 |
| 5D5 | SEQ ID NO: 87 | SEQ ID NO: 98 |
| 5B5 | SEQ ID NO: 88 | SEQ ID NO: 99 |
| 2C6 | SEQ ID NO: 89 | SEQ ID NO: 100 |
| 2F8 | SEQ ID NO: 90 | SEQ ID NO: 101 |
| 4H9 | SEQ ID NO: 91 | SEQ ID NO: 102 |
| 1H | SEQ ID NO: 92 | SEQ ID NO: 103 |
| 2G | SEQ ID NO: 93 | SEQ ID NO: 104 |
| 5G | SEQ ID NO: 94 | SEQ ID NO: 105 |
| 5C3 | SEQ ID NO: 95 | SEQ ID NO: 106 |

4. Production of Anti-BCMA IgG Antibodies from Selected Anti-BCMA Phages

Polynucleotides having nucleotide sequences encoding the antibodies selected according to Example 1.3 were synthesized. The prepared polynucleotides were cloned into animal cell expression vectors (heavy chain expression vector: pAB1-HC, and light chain expression vector: pAB1-LC). Prepared were a total of 22 vectors containing polynucleotides encoding heavy and light chains for each of the eleven antibody clones (B58, 5A6, 5D5, 5B5, 2C6, 2F8, 4H9, 1H, 2G, 5G, and 5C3). Each of the prepared vectors contained an IgG1-type sequence.

CHO—S cells were cultured in a CD-CHO (Gibco, 10743) medium, and the prepared vectors were introduced into the CHO—S cells using polyethylenimine (PEI). Transduced CHO—S cells were cultured in CD-CHO medium for about 7 days at 8% $CO_2$, at 37° C. at 110 rpm.

The prepared CHO—S cell culture was passed through a MabSelect SuRe column (GE healthcare, 5 mL) equilibrated with equilibration buffer (50 mM Tris-HCl, pH7.5, and 100 mM NaCl) to allow the expressed antibody to bind to the column. The antibody was eluted with a solution of 50 mM Na-citrate (pH 3.4) and 100 mM NaCl, and then, neutralized using 1M Tris-HCl (pH 9.0) to obtain a final pH of 7.2. The buffer was then exchanged with PBS (pH 7.4) and the anti-BCMA IgG antibodies B58, 5A6, 5D5, 5B5, 2C6, 2F8, 4H9, 1H, 2G, 5G, and 5C3 were stored at 4° C. until use.

5. Preparation of Mutants of 5A6 and 5D5

In order to improve the productivity of the selected 5A6 and 5D5 antibodies, mutated antibodies were prepared in accordance with the nucleotide sequences of Table 4 by mutating one or two amino acid residues in the light chain CDR of the antibody.

The amino acid sequences of CDR-L1, CDR-L2, and CDR-L3 of the light chain variable region (SEQ ID NOS: 107 to 114) of the 5A6 mutant antibodies and the light chain variable region (SEQ ID NOS: 115 to 119) of the 5D5 mutant antibodies are shown in Table 5 and Table 6, respectively. In Tables 5 and 6, the underlined and bold amino acid residues are mutated moieties (WT: wild type, LM: light chain mutants).

TABLE 5

| Antibody | CDR-L1 | CDR-L2 | CDR-L3 |
|---|---|---|---|
| 5A6 WT | QGDSLRSYYVN (SEQ ID NO: 57) | DHSKRPT (SEQ ID NO: 67) | QSYDSSTV (SEQ ID NO: 76) |
| 5A6 LM1 | QGESLRSYYVN (SEQ ID NO: 120) | DHSKRPT (SEQ ID NO: 67) | QSYDSSTV (SEQ ID NO: 76) |

TABLE 5-continued

| Antibody | CDR-L1 | CDR-L2 | CDR-L3 |
|---|---|---|---|
| 5A6 LM2 | QGDALRSYYVN (SEQ ID NO: 121) | DHSKRPT (SEQ ID NO: 67) | QSYDSSTV (SEQ ID NO: 76) |
| 5A6 LM3 | QGDSLRSYYVN (SEQ ID NO: 57) | DHSKRPT (SEQ ID NO: 67) | QSYESSTV (SEQ ID NO: 122) |
| 5A6 LM4 | QGDSLRSYYVN (SEQ ID NO: 57) | DHSKRPT (SEQ ID NO: 67) | QSYDASTV (SEQ ID NO: 123) |
| 5A6 LM5 | QGESLRSYYVN (SEQ ID NO: 120) | DHSKRPT (SEQ ID NO: 67) | QSYESSTV (SEQ ID NO: 122) |
| 5A6 LM6 | QGESLRSYYVN (SEQ ID NO: 120) | DHSKRPT (SEQ ID NO: 67) | QSYDASTV (SEQ ID NO: 123) |
| 5A6 LM7 | QGDALRSYYVN (SEQ ID NO: 121) | DHSKRPT (SEQ ID NO: 67) | QSYESSTV (SEQ ID NO: 122) |
| 5A6 LM8 | QGDALRSYYVN (SEQ ID NO: 121) | DHSKRPT (SEQ ID NO: 67) | QSYDASTV (SEQ ID NO: 123) |

TABLE 6

| Antibody | CDR-L1 | CDR-L2 | CDR-L3 |
|---|---|---|---|
| 5D5 WT | KASQDIDDDIN (SEQ ID NO: 58) | DASLRAT (SEQ ID NO: 68) | QQSLRTPI (SEQ ID NO: 77) |
| 5D5 LM1 | KASQDIDNDIN (SEQ ID NO: 124) | DASLRAT (SEQ ID NO: 68) | QQSLRTPI (SEQ ID NO: 77) |
| 5D5 LM2 | KASQDIDEDIN (SEQ ID NO: 125) | DASLRAT (SEQ ID NO: 68) | QQSLRTPI (SEQ ID NO: 77) |
| 5D5 LM3 | KASQDIDADIN (SEQ ID NO: 126) | DASLRAT (SEQ ID NO: 68) | QQSLRTPI (SEQ ID NO: 77) |
| 5D5 LM4 | KASQDIDDAIN (SEQ ID NO: 127) | DASLRAT (SEQ ID NO: 68) | QQSLRTPI (SEQ ID NO: 77) |
| 5D5 LM5 | KASQDIDDEIN (SEQ ID NO: 128) | DASLRAT (SEQ ID NO: 68) | QQSLRTPI (SEQ ID NO: 77) |

Example 2. Kinetic Analysis of Anti-BCMA IgG Antibody

1. Determination of Binding Ability of Anti-BCMA IgG Antibody to BCMA
(1) Determination of Binding Ability to Recombinant BCMA Specific binding abilities of the anti-BCMA IgG antibodies isolated in Example 1.4 to recombinant BCMA protein were analyzed by ELISA.

Figure 1B:
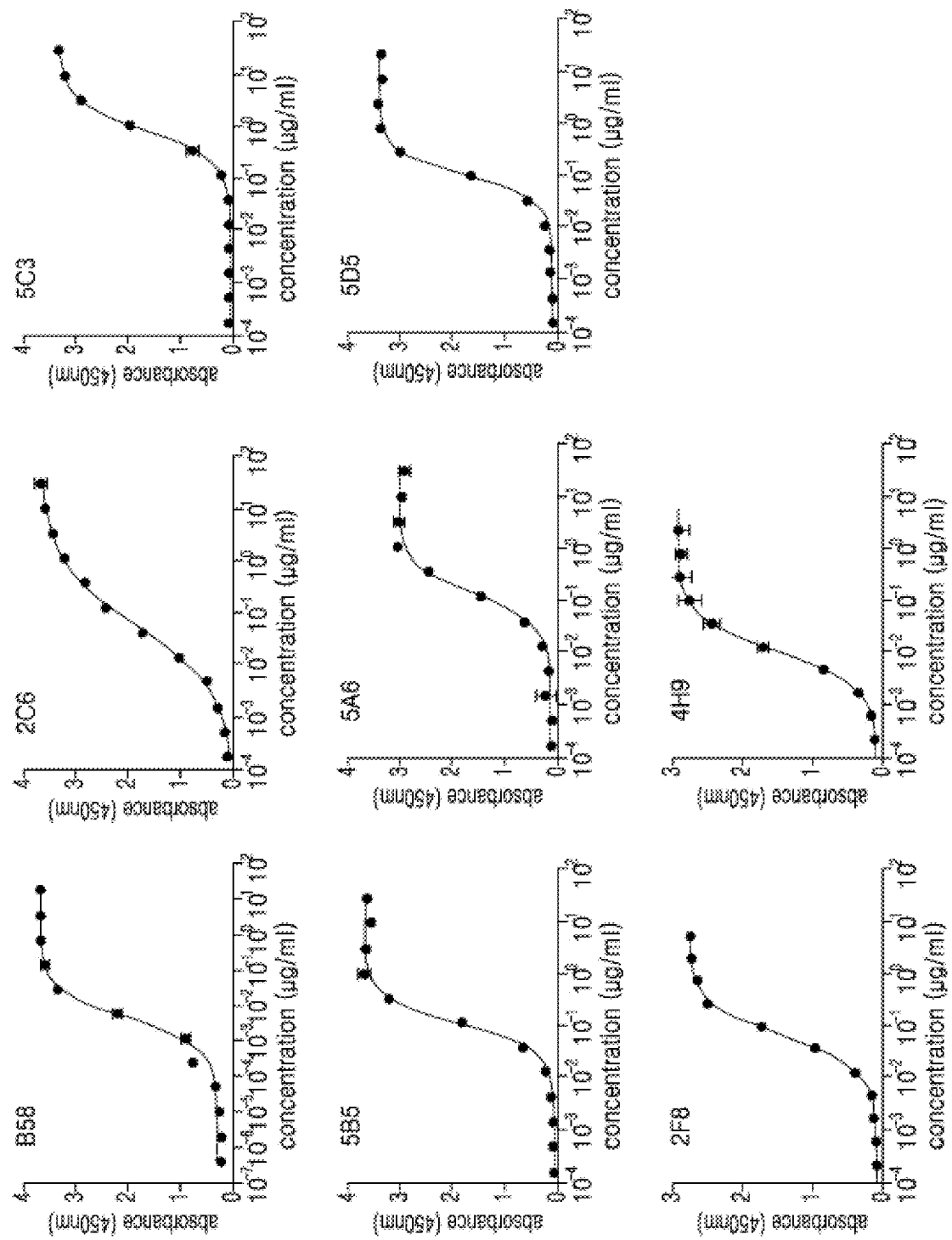
FIG. 1B is a graph showing results of measuring, by ELISA, the binding ability of antibodies B58, 2C6, 5C3, 5B5, 5A6, 5D5, 2F8, and 4H9 to human BCMA.

Using recombinant human BCMA or monkey BCMA as an antigen, and HRP-conjugated Fab polychronal antibody reagent (Pierce, 31414) as a secondary antibody, ELISA was performed as described in Example 1.3. Absorbancies at 450 nm according to the concentrations of the antibodies are shown in FIGS. 1A and 1B. FIG. 1A illustrates graphs of the binding affinities of antibodies 1H, 2G, and 5G to human or monkey BCMA, and FIG. 1B illustrates graphs of the binding abilities of antibodies B58, 2C6, 5C3, 5B5, 5A6, 5D5, 4H9, and 2F8 to human BCMA.

As shown in FIG. 1A, antibodies 1H, 2G, and 5G bound to human BCMA and monkey BCMA in a concentration-dependent manner. The binding ability to human BCMA was higher in the order of antibodies 2G, 1H, and 5G, and the binding ability to monkey BCMA was highest for antibody 1H, and was similar for antibodies 2G and 5G. As shown in FIG. 1B, it was found that all the eight anti-BCMA antibodies (B58, 2C6, 5C3, 5B5, 5A6, 5D5, 4H9, and 2F8) bound to human BCMA in a concentration-dependent manner.

(2) Determination of Binding Ability to BCMA on Cell Surface

The degrees of binding of the screened anti-BCMA IgG antibodies expressed on cell surfaces were analyzed using a fluorescence-activated cell sorting (FACS) system.

Multiple myeloma cancer cells H929 (ATCC, CRL9068™) and OPM-2 cell line (DSMZ, ACC 50), which are known to express BCMA, were prepared, and human BCMA-overexpressed CHOK1-hBCMA cell line (constructed by ABIBio) were prepared. As control groups, CHOK1 (ATCC, CRL-9618) and Raji (B-lymphocyte cancer cell line) (ATCC, CCL-86™) cell lines that do not express BCMA were used.

Figure 2A:
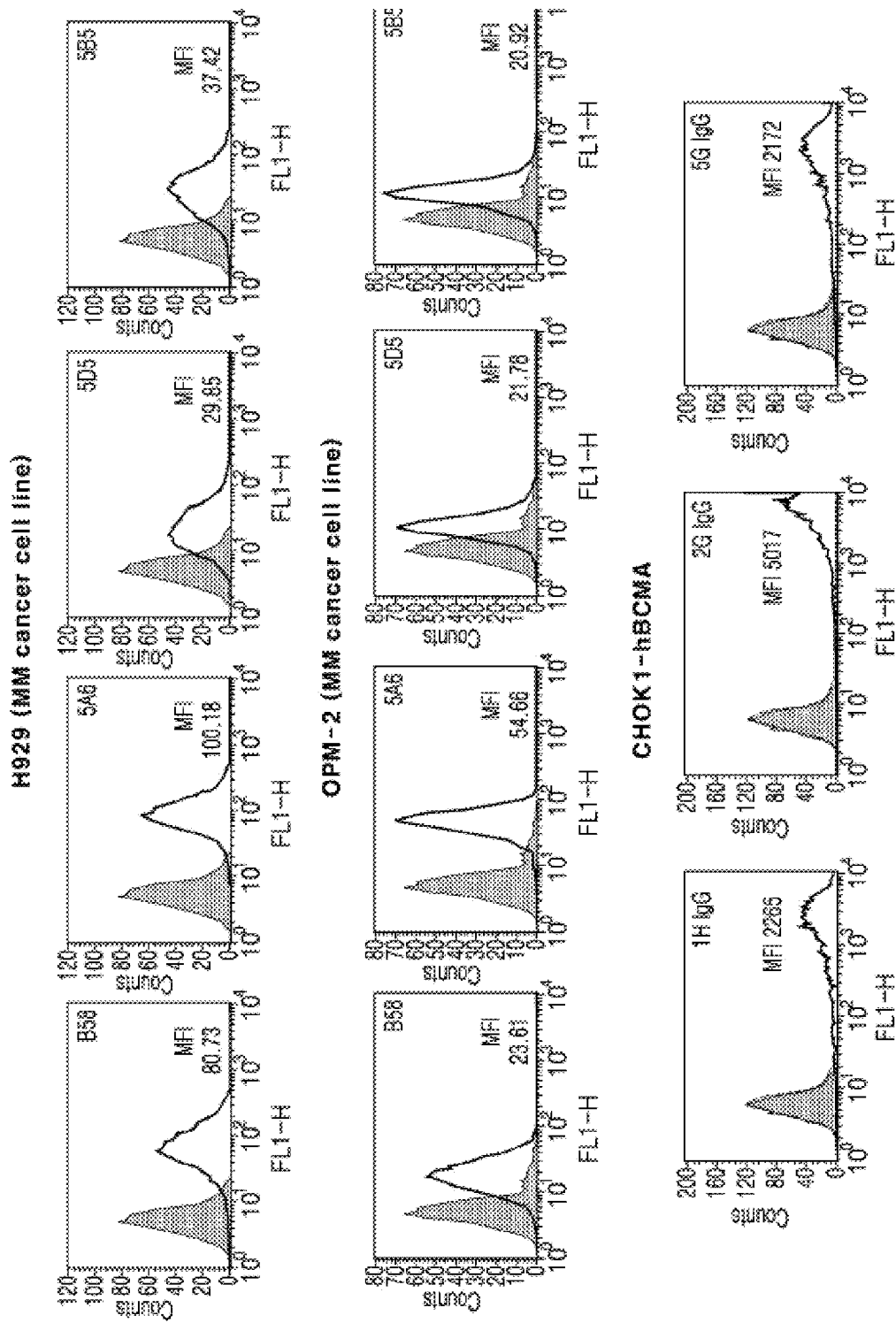
FIG. 2A is a graph showing results of measuring, by fluorescence activated cell sorting (FACS), the binding ability of selected antibodies to cell-surface BCMA in H929 (multiple myeloma cells), OPM-2 (multiple myeloma cells), and human BCMA-overexpressed CHOK1-hBCMA cell lines.
Figure 2B:
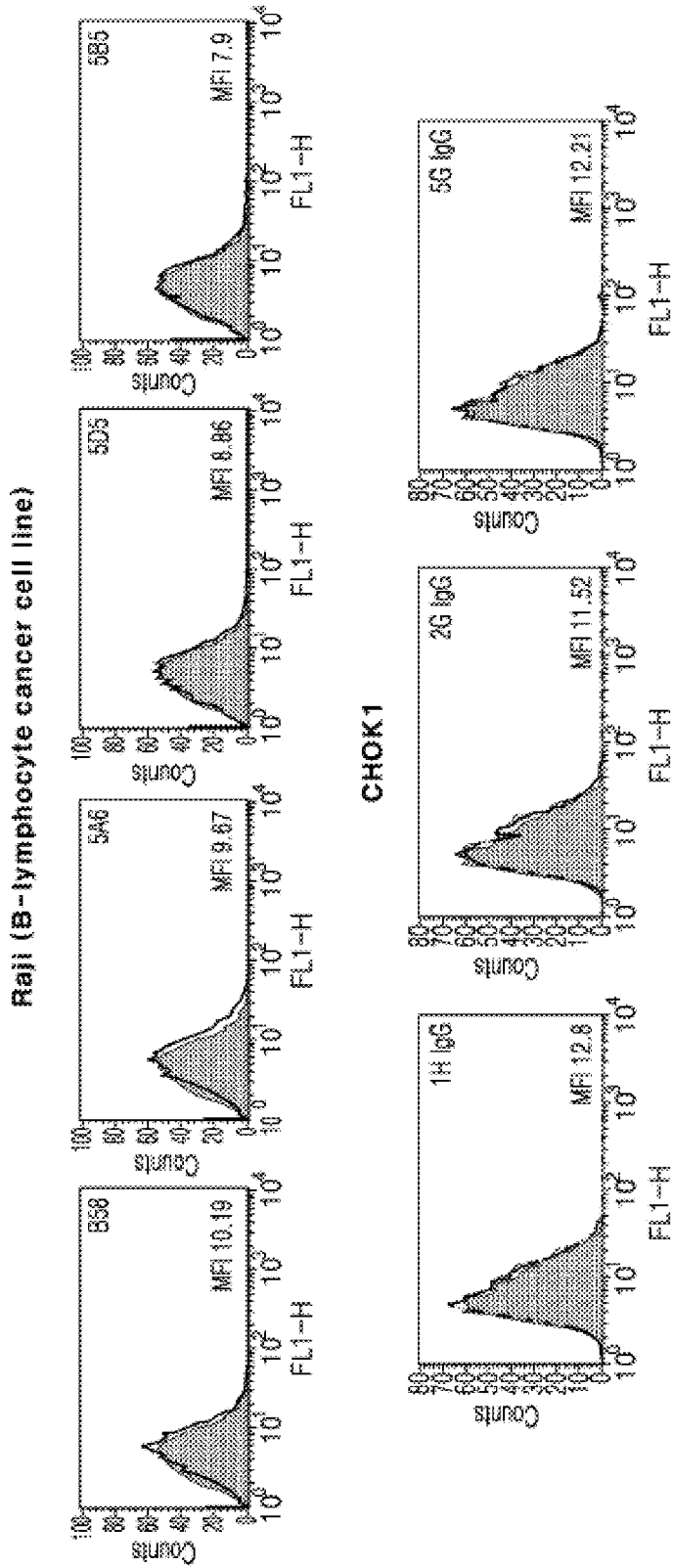
FIG. 2B is a graph showing results of measuring, by FACS, the binding ability of selected antibodies to cell-surface BCMA in Raji (B-lymphocyte cancer cell lines), which do not express BCMA, and CHOK1 cell lines.

10 μg/ml of the seven IgG antibodies (B58, 5A6, 5D5, 5B5, 1H, 2G, and 5G) purified in Example 1.4 was added to the prepared cells, incubated at 4° C. for 1 hour, and then washed two times with a PBS buffer solution. The anti-human Fc-FITC was diluted in 1:400, incubated at 4° C. for 1 hour, and then washed with a PBS buffer solution. These processes were repeated. The fluorescence intensities of the cells were measured using a FACSCalibur, and are shown in FIGS. 2A and 2B. In FIGS. 2A and 2B, MFI indicates mean fluorescence intensity.

As shown in FIGS. 2A and 2B, it was found that all the selected antibodies specifically bound to BCMA expressed on cell surfaces, but not to the cells in which BCMA is not expressed. Accordingly, it was confirmed that the selected antibody has a binding ability specific to the extracellular domain of BCMA expressed on the cell surface as well as to the recombinant BCMA protein, and it is possible to specifically target the BCMA-expressing cancer cell line using this anti-BCMA antibody.

2. Affinity Analysis of Anti-BCMA IgG Antibody to Human BCMA and Monkey BCMA

The affinities of the selected 11 anti-BCMA antibodies to human BCMA and monkey BCMA were analyzed.

A 96-well black microplate was mounted on a Biosensor tray case, 200 µl of 1XKB was added to each of the 8 wells, and then 8 Ni-NTA biosensors (Fortebio) were inserted thereto for hydration for 10 minutes. For antigen fixation, 5 µg/ml of recombinant human BCMA-His (Sino Biological Inc.) was diluted using 1XKB. Experiments were performed with a threshold of 0.5 to 1.0 nm, and Octet Data Acquisition 9.0 software was activated to create an Octet program template. The first step was for Baseline 1, the second step was for loading, and the threshold was fixed to 0.5 to 1.0 nm. In the third step, which was for Baseline 2, association for 5 minutes and dissociation for 20 minutes were performed. A plate temperature was fixed to 30° C., and the prepared buffer solution was placed in order into a new 96-well black microplate according to the Octet program template. 200 µl of 1XKB used as Baseline 1 and recombinant human BCMA-Fc/His which is an antigen to be loaded were diluted to 5 µg/ml, and 200 µl of the dilution was added thereto. After adding 200 µl of 1XKB used as Baseline 2, 200 µl of the antibody to be reacted with the antigen was dispensed, and the instrument was operated. After completion of the experiment, an association constant (kon), a dissociation constant (kdis), and an equilibrium dissociation constant (KD) for each antibody were analyzed and calculated with Octet Analysis 9.0 software. The results thereof are shown in Table 7.

TABLE 7

| Antibody | KD(M) | kon(1/Ms) | kdis(1/s) | Chi | $R^2$ |
|---|---|---|---|---|---|
| B58 | 2.73E−11 | 7.35E+05 | 2.00E−05 | 0.932 | 0.996 |
| 2C6 | 3.70E−10 | 1.09E+06 | 4.03E−04 | 1.227 | 0.989 |
| 2F8 | 1.04E−07 | 1.47E+06 | 1.52E−02 | 0.097 | 0.951 |
| 4H9 | 1.29E−09 | 1.38E+06 | 1.79E−03 | 1.256 | 0.895 |
| 1H | 1.45E−09 | 4.09E+05 | 5.92E−04 | 0.317 | 0.988 |
| 2G | 1.08E−09 | 7.20E+05 | 7.80E−04 | 0.933 | 0.982 |
| 5G | 3.61E−07 | 3.97E+04 | 1.43E−02 | 0.177 | 0.948 |
| 5A6 | 2.12E−11 | 5.09E+05 | 1.08E−05 | 0.147 | 0.995 |
| 5B5 | 2.02E−10 | 1.24E+06 | 2.50E−04 | 0.929 | 0.991 |
| 5D5 | 1.14E−10 | 9.19E+05 | 1.05E−04 | 0.587 | 0.993 |
| 5C3 | 1.64E−08 | 5.91E+05 | 9.66E−03 | 0.269 | 0.936 |

As shown in Table 7, the affinities of antibodies B58 and 5A6 had a KD value of about $10^{-11}$, and those of antibodies 2C6, 5B5, and 5D5 had a KD value of about $10^{-10}$. Thus it was confirmed that the selected antibodies have high binding ability to human BCMA protein. Affinities to monkey BCMA were additionally confirmed with three antibodies (5A6, 5B5, and 5D5) among the above antibodies, other than antibody 2C6 having insignificant binding ability to human BCMA on cell surface, and antibody B58 having no affinity to monkey BCMA, and the results are shown in Table 8.

TABLE 8

| Antibody | KD(M) | kon(1/Ms) | kdis(1/s) | Chi | $R^2$ |
|---|---|---|---|---|---|
| 5A6 | 4.51E−09 | 3.61E+05 | 1.63E−03 | 0.526 | 0.9943 |
| 5B5 | 4.61E−10 | 4.79E+06 | 2.21E−03 | 0.0652 | 0.9685 |
| 5D5 | 3.46E−10 | 1.69E+06 | 5.85E−04 | 0.0477 | 0.9945 |

As shown in Table 8, it was confirmed that antibodies 5A6, 5B5, and 5D5 have high affinity for monkey BCMA as well as to human BCMA.

3. Analysis of Species Cross-Reactivity of Anti-BCMA Antibodies

Whether or not antibodies B58, 5A6, 5D5, and 5B5 among the selected antibodies have cross-species binding ability was analyzed by ELISA.

100 ng of human, monkey, mouse, and rat BCMA antigens prepared in Example 1.1 were coated on the bottom of the plate, and then coated with 3% BSA to block nonspecific binding. Using the selected anti-BCMA IgG antibodies as primary antibodies, and the anti-human Fab HRP (1:20000 dilution) as a secondary antibody, ELISA assay was performed as described in Example 1.3.

Figure 3:
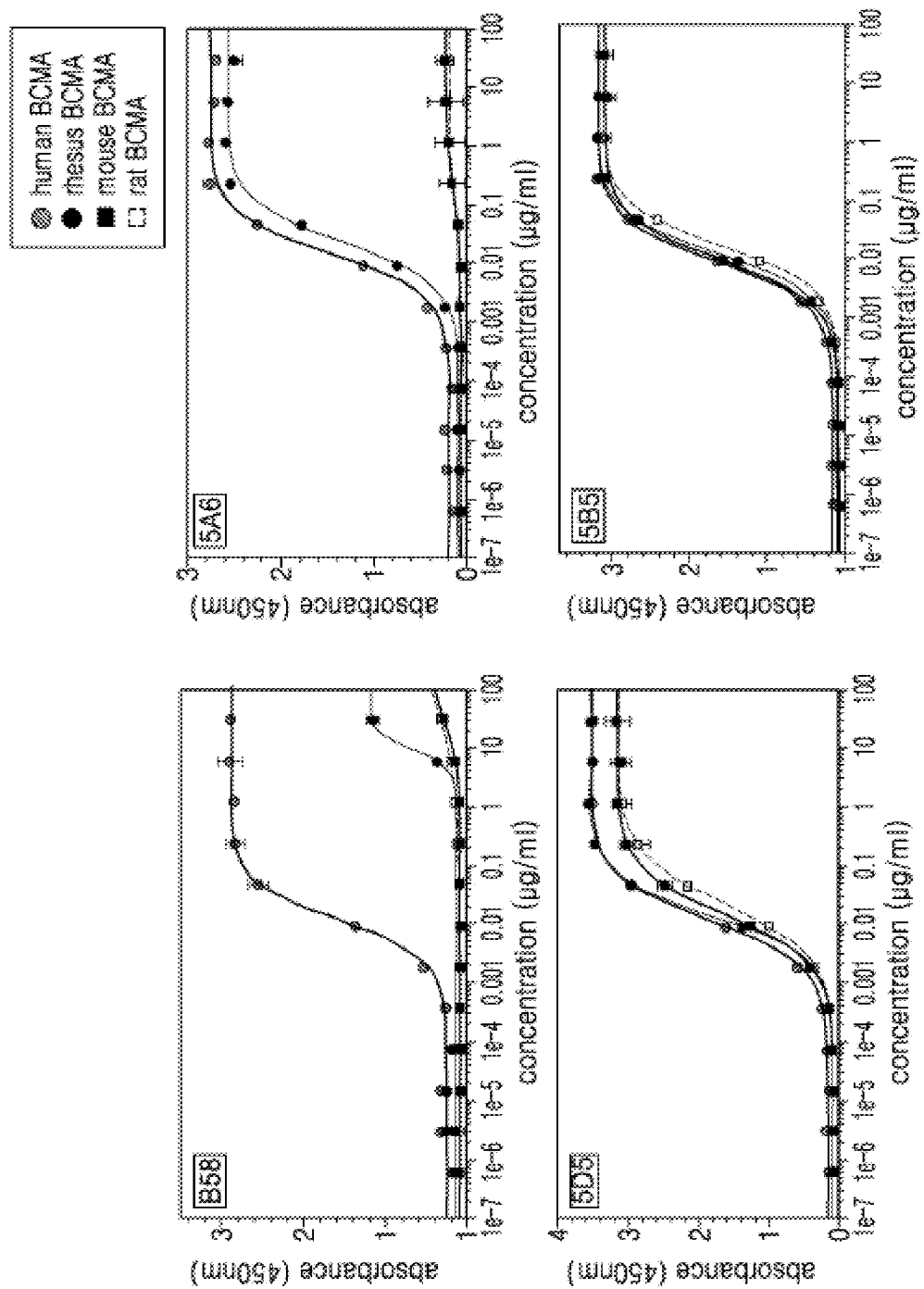
FIG. 3 is a graph showing results of measuring, by ELISA, the binding ability of antibodies B58, 5A6, 5D5, and 5B5 to human, monkey, mouse, and rat BCMA.

Absorbancies at 450 nm measured with a microplate reader are shown in FIG. 3, and half maximal effective concentrations ($EC_{50}$) (nM) are shown in Table 9.

TABLE 9

| Antigen | 5A6 antibody | B58 antibody | 5D5 antibody | 5B5 antibody |
|---|---|---|---|---|
| Human BCMA | 100 | 79 | 140 | 63 |
| Monkey BCMA | 153 | — | 94 | 82 |
| Mouse BCMA | — | — | 150 | 110 |
| Rat BCMA | — | — | 98 | 65 |

As shown in FIG. 3 and Table 9, antibody B58 had binding ability only to human BCMA, and antibody 5A6 had binding ability to human and monkey BCMA. It was confirmed that antibodies 5D5 and 5B5 have binding ability to all BCMAs of the assayed species (human, monkey, mouse, and rat).

4. Determination of Specificity of Anti-BCMA IgG to BCMA

BCMA is known to be involved in the maturation process of B cells, and TACI and BAFF-receptors are known to be involved in this maturation process. Whether or not the selected antibodies bind to BCMA-related protein was analyzed by ELISA assay.

Specifically, human BCMA-Fc (R&D system, 193-BC-050), TACI-Fc (R&D system, 174-TC), and BAFF-receptors (R&D system, 1162-BR) were diluted using a PBS buffer. Then, 100 ng per well was coated on the ELISA plate. Using the selected anti-BCMA IgG antibodies as primary antibodies, and the anti-human Fab HRP (1:20000 dilution) as a secondary antibody, ELISA assay was performed as described in Example 1.4(1). As a comparative group, anti-BCMA monoclonal antibody J6MO (GSK) was used. Absorbancies at 450 nm measured with a microplate reader are shown in FIG. 4.

Figure 4:
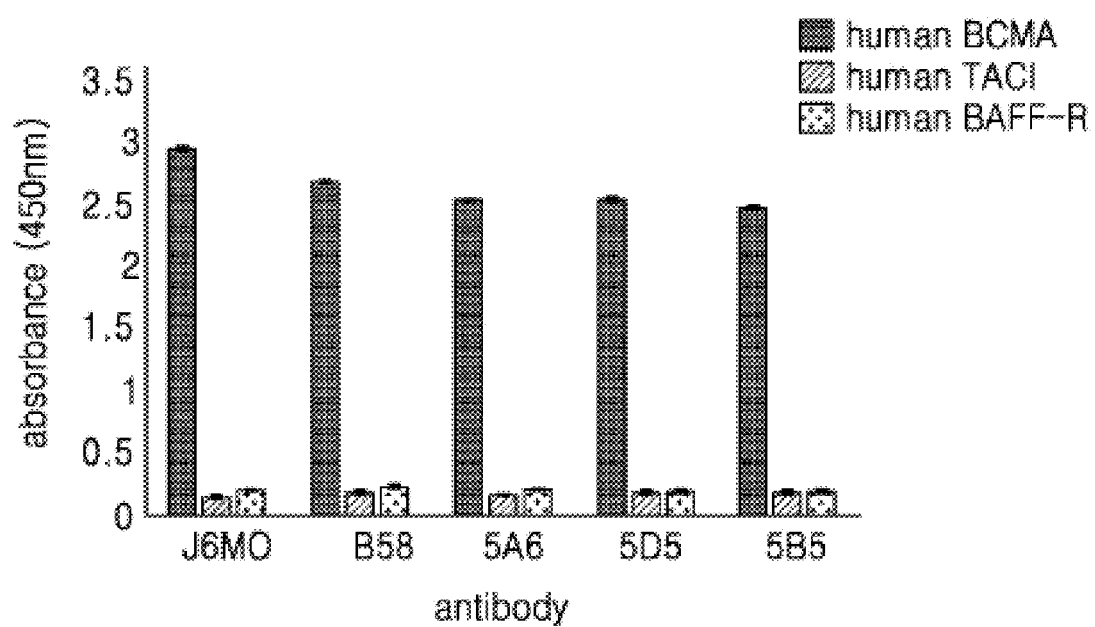
FIG. 4 is a graph showing results of measuring, by ELISA, the binding ability of antibodies B58, 5A6, 5D5, and 5B5 to human BCMA, human TACI, and human BAFF-receptors.
Figure 5A:
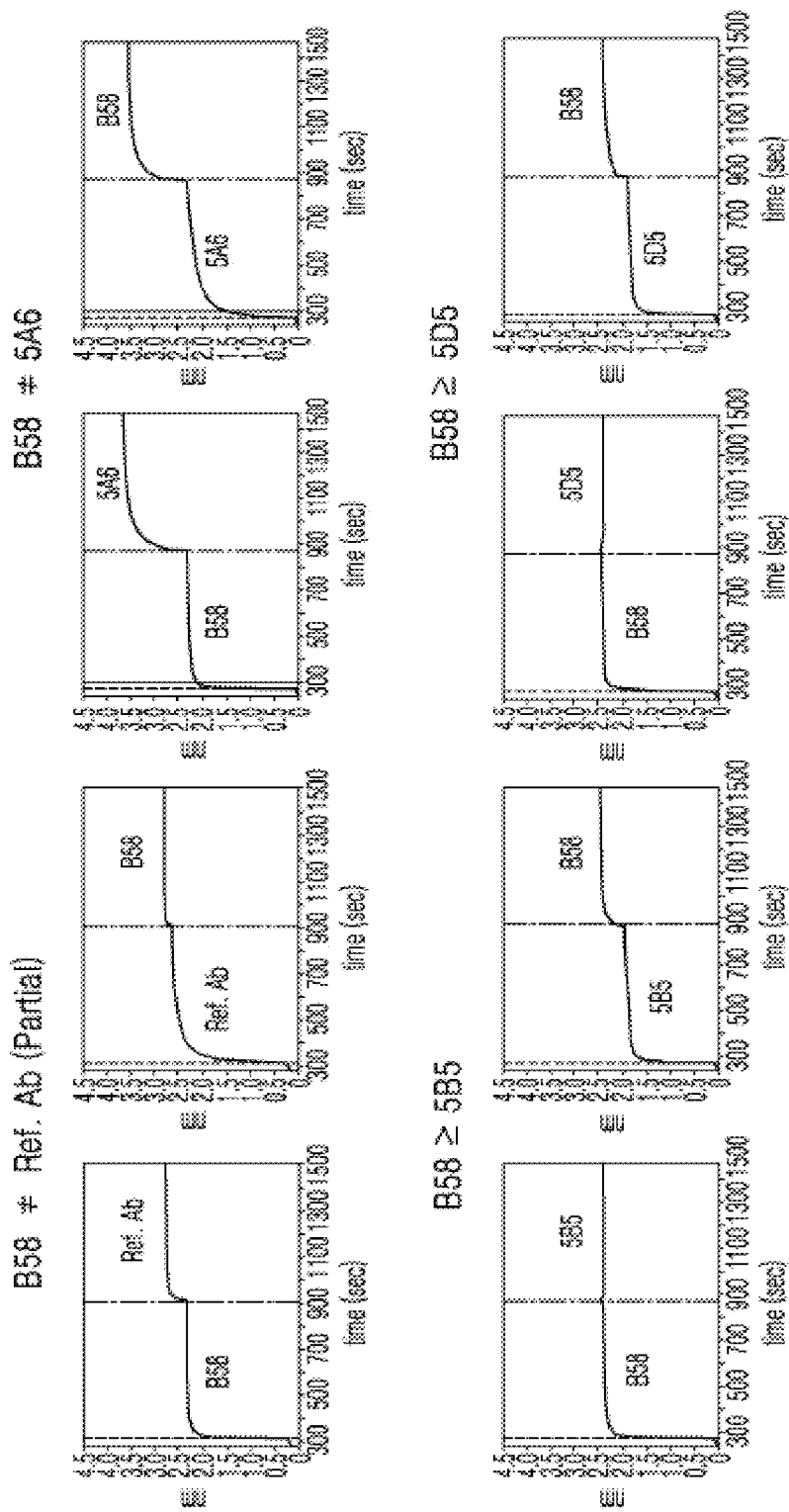
FIGS. 5A, 5B, 5C and 5D are graphs showing results of competitive binding of antibodies B58, 5A6, 5D5, and 5B5 to other antibodies and human BCMA (Ref. Ab: J6MO antibody).
Figure 5B:
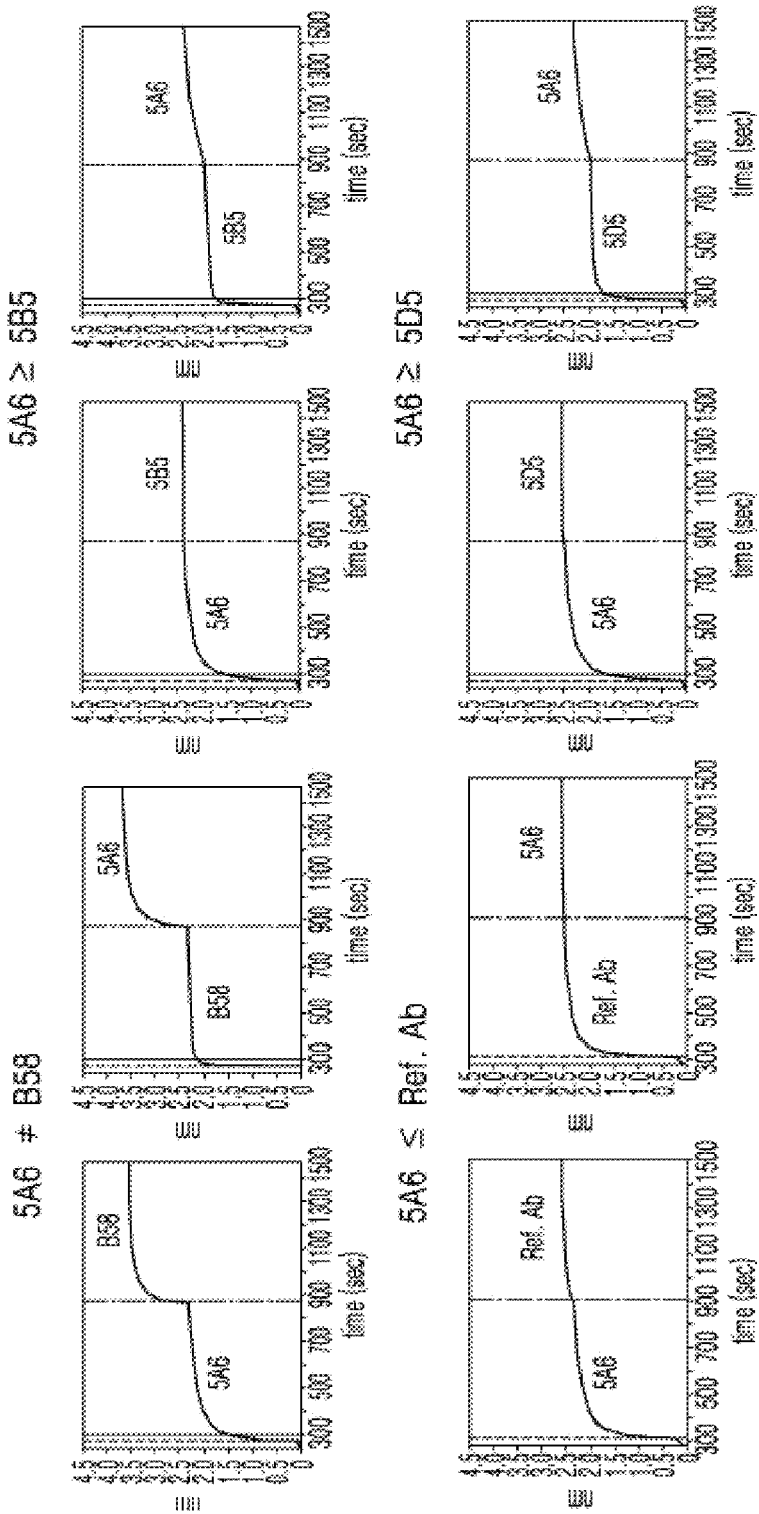
Figure 5C:
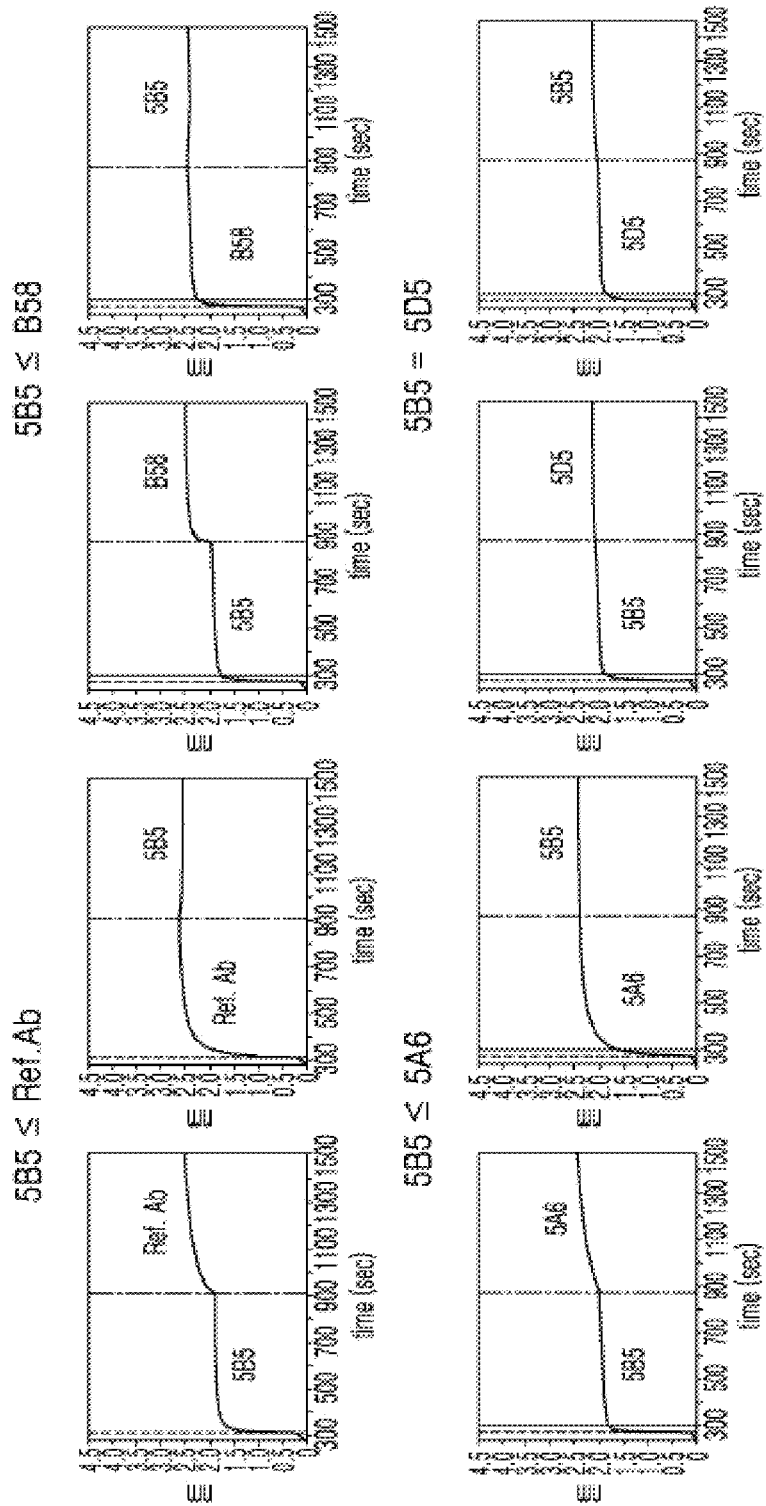
Figure 5D:
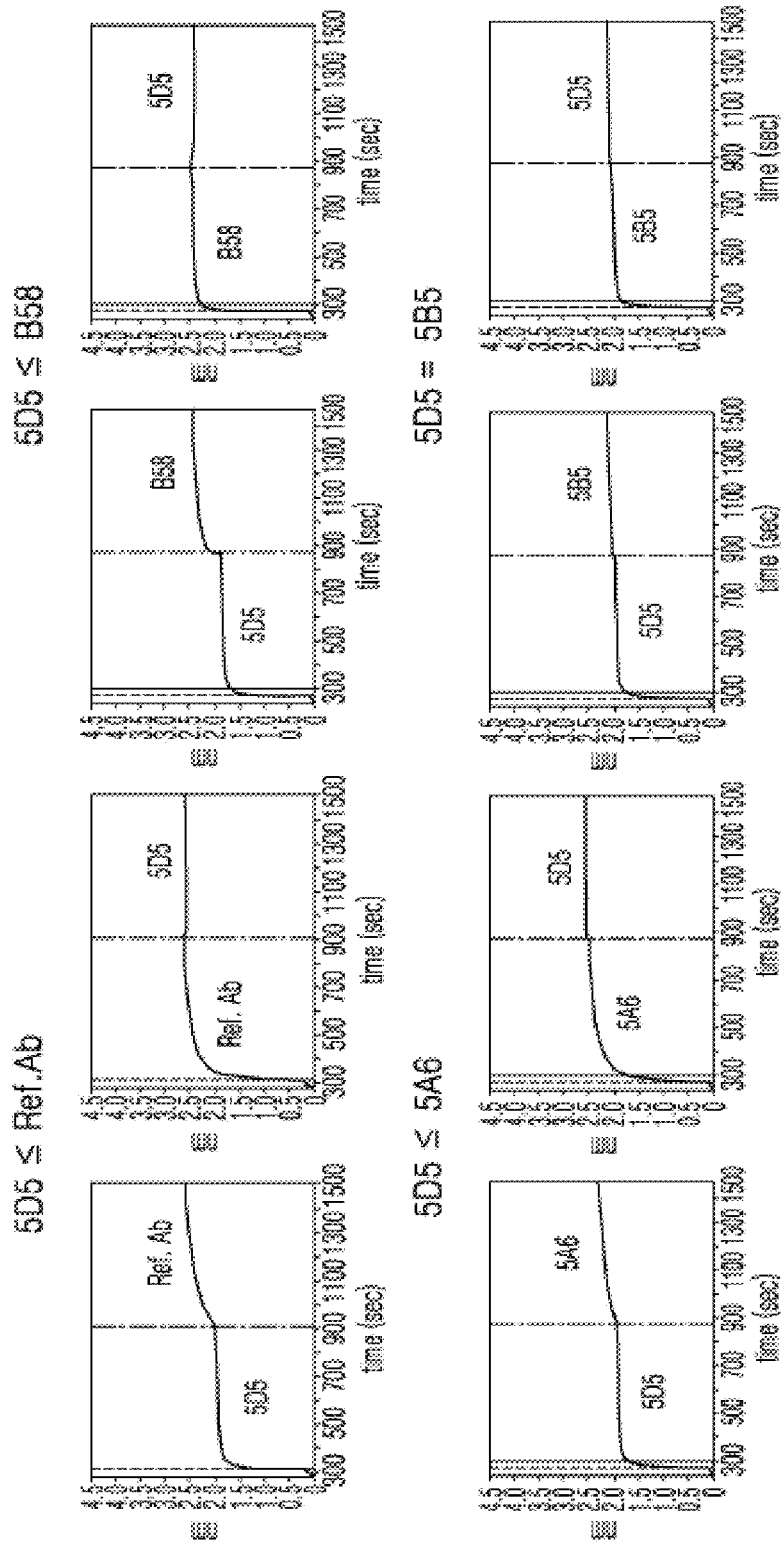

As shown in FIG. 4, antibodies B58, 5A6, 5D5, and 5B5 did not bind to TACI and BAFF-receptors, but bind only to BCMA. Therefore, it was confirmed that the selected four anti-BCMA antibodies B58, 5A6, 5D5, and 5B5 specifically bind to BCMA.

5. Relative Comparison of Epitopes for Each Anti-BCMA Antibody

For relative comparison of binding sites to BCMA using the selected four antibodies (IgG), competitive binding abilities to human BCMA among the selected antibodies were analyzed.

As described in Example 2.2, the binding abilities among the antibodies were analyzed using an Octet analysis system. In the Octet program template, the first step was baseline1, the second step was loading, and the threshold was fixed to 0.3 nm. The third step was set as the Baseline. In the fourth and fifth steps, each antibody was allowed to react, and the time was set to 10 minutes. The prepared buffer was placed in order into a new 96-well black microplate according to the Octet program template. 200 µl of 1XKB used as Baseline 1 was added. Recombinant human BCMA (Fc and His tag fused), which is an antigen to be loaded, was diluted to 5 µg/ml, and 200 µl was added to each well. 200 µl of 1XKB used as Baseline 1 was added. 200 µl of the first antibody which binds first to the antigen was added to each well. 200 µl of the second antibody was added to each well. The temperature of the test plate was fixed at 30° C. After all the samples were added, the instrument was operated. After the experiment was finished, competition between the first antibody and the second antibody was analyzed with Octet analysis 9.0 software, and the results are shown in FIGS. 5A to 5D (Ref. Ab: J6MO antibody).

As shown in FIGS. 5A to 5D, it was confirmed that antibodies B58 and 5A6 had different binding sites on the antigen, that is, epitopes to which the antibodies bind, and antibodies 5B5 and 5D5 had the same epitopes. In addition, it was confirmed that the epitopes of antibodies 5B5 and 5D5 antibody were partially identical to that of antibody B58. Therefore, it was confirmed that the selected four types of antibodies have various binding sites to the antigen BCMA.

Example 3. Effect of Anti-BCMA IgG Antibodies on Cancer Cells

1. Neutralizing Effect of Anti-BCMA IgG Antibody

Whether or not the selected anti-BCMA bodies could interrupt the binding of BCMA and ligands (APRIL and BAFF) was confirmed by ELISA-based solution competition assay.

Specifically, human BCMA-Fc (R&D system, 193-BC-050) was diluted using a PBS buffer, and then 100 ng of the dilution per well was coated on the ELISA plate. After the coating, the plate was emptied, and 100 µl of PBST containing 1% BSA was added to each well and incubated at 37° C. for 2 hours. The antibodies diluted at a concentration of 50 µg/ml to 0.00028 µg/ml were mixed with 10 ng/ml of APRIL protein (R&D, 5860-AP-010/CF) or 200 ng/ml of BAFF (R&D, 2149-BF-010/CF). An IgG1 antibody was used as a negative control, and a J6MO antibody was used as a comparative group.

Using anti-HA-HRP (Roche, 12013819001) or anti-His-HRP (Roche, 11965085001) as secondary antibodies, ELISA assay was performed as described in Example 1.4(1). As a comparative group, anti-BCMA monoclonal antibody J6MO (GSK) was used. Absorbance was measured at 450 nm, and the results are shown in FIGS. 6A and 6B.

Figure 6A:
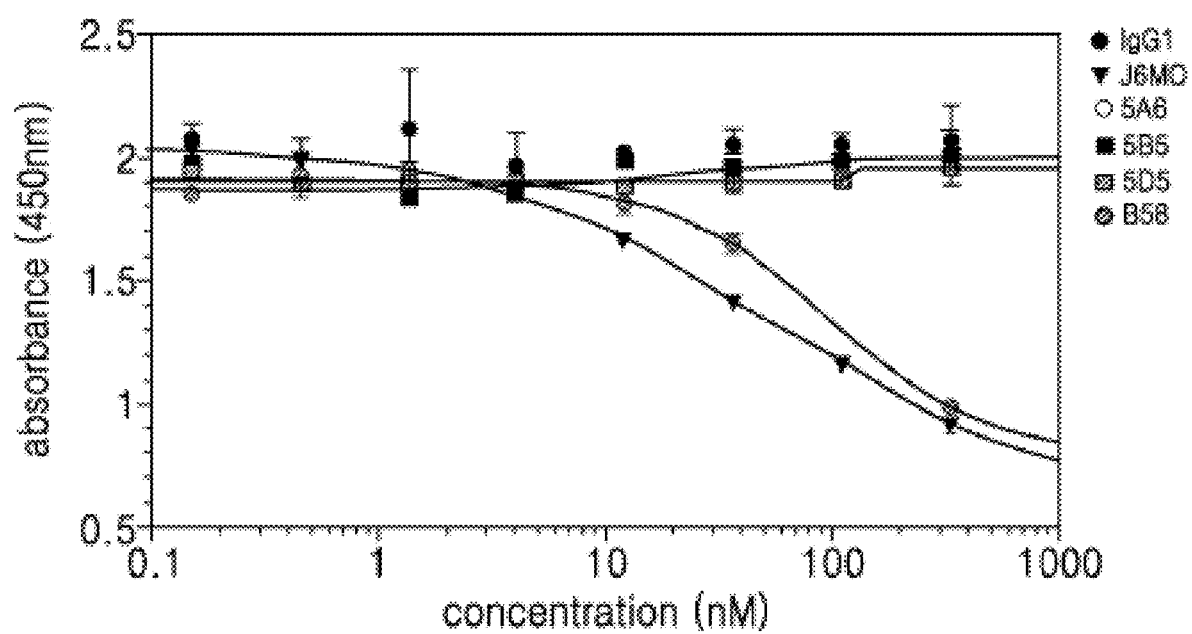
FIG. 6A is a graph showing results of competitive binding of an APRIL ligand and an antibody to human BCMA.
Figure 6B:
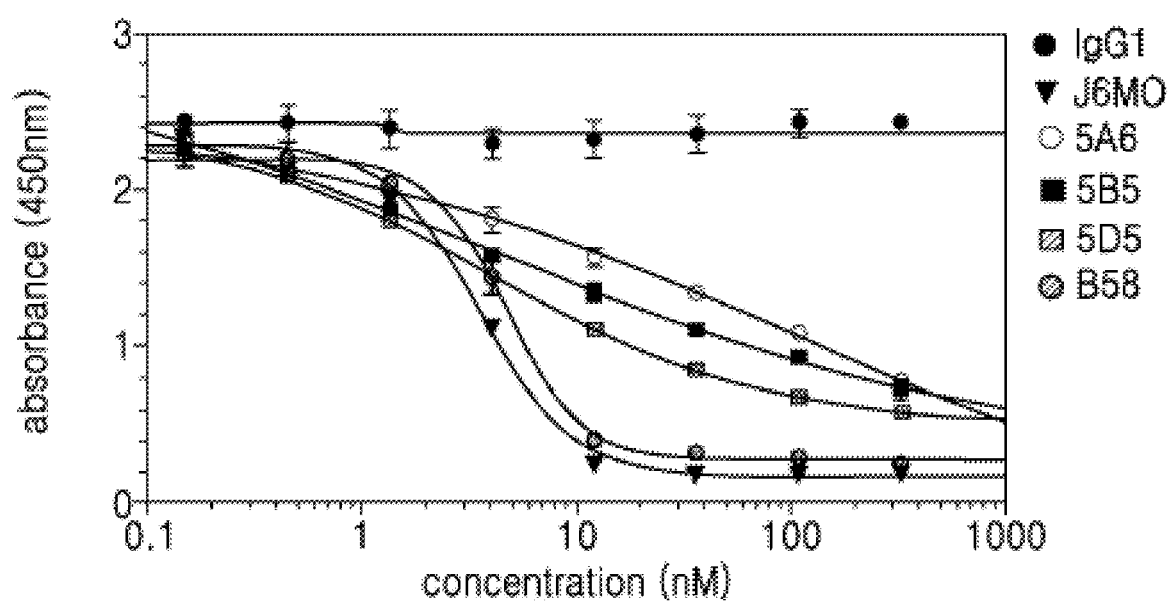
FIG. 6B is a graph showing results of competitive binding of a BAFF ligand and an antibody to human BCMA.

As shown in FIGS. 6A and 6B, it was confirmed that B58 antibody effectively inhibits the binding of BCMA and BAFF, and also inhibits the binding of BCMA and APRIL. It was found that antibodies 5A6, 5B5, and 5D5 are unable to inhibit the binding ability of APRIL, but partially inhibit the binding ability of BAFF. Therefore, it was confirmed that the selected antibodies differ in the degree of inhibition of binding ability of BCMA with ligands, due to different binding sites for the target antigen BCMA, but there is a possibility of effectively inhibiting the growth of cancer cells by controlling and inhibiting the binding of the ligands.

2. Evaluation of Antibody-Dependent Cell-Mediated Cytotoxicity (ADCC)

Antibody-dependent cell-mediated cytotoxicities (ADCC) of the selected antibodies were measured using an ADCC bioassay core kit (Promega, G0718).

Specifically, H929 (ATCC, CRL9068™) which greatly expresses human BCMA and Raji (ATCC, CCL86™) which expresses less human BCMA were used as target cells. Antibodies B58, 5A6, 5D5, and 5B5 were prepared as anti-BCMA antibodies.

In addition, in order to induce functional inhibition in the Fc part involved in antibody-dependent cytotoxicity and use the same as a negative control, 5A6 DANA mutant antibodies in which the aspartic acid amino acid residue at position 265 of the 5A6 Fc part was substituted with alanine ("D265A"), and the asparagine residue at the position 297 was substituted with alanine ("N297A") were prepared (Cancer Cell, vol. 19, issue 1, pp. 101-113).

An ADCC assay buffer was prepared by adding RPMI/1640 (Promega, G708A) and 4% low-IgG serum (Promega, AX20A). H929 and Raji cell lines resuspended in the ADCC assay buffer were added to 96 well plates (white, flat bottom, Corning, CLS3917) at 5000 cells per well (25 µl). Anti-BCMA antibodies were prepared by serially diluting to ⅛ from 133.3 nM (20 µg/ml) with the ADCC assay buffer. 25 µl of the prepared antibodies were added per well. After 3.6 ml of the ADCC assay buffer was placed in a 15-ml tube, the ADCC Bioassay Effector cell (Promega, G701A) was taken out of a liquid nitrogen tank, rapidly dissolved in a 37° C.-water bath, and then poured into the 15-ml tube containing the ADCC assay buffer. After being mixed well, 25 µl of the effector cells were carefully added each time to the tube and cultured at 37° C. under 5% $CO_2$ conditions for about 6 hours. Meanwhile, a Bio-Glo™ luciferase assay buffer (Promega, G720A) was dissolved at room temperature, and then added to a Bio-Glo™ luciferase assay substrate (Promega, G719A) and mixed well to prepare a BIO-GLO™ luciferase assay reagent. After cell culture, the 96-well plate was left at room temperature for about 10 minutes, and then 25 µl of the BIO-GLO™ luciferase assay reagent was carefully added to each well. After the 96-well plate was left to stand at room temperature for 5 minutes, the intensity of luminescence was measured using a PHERAstar FS (from BMG LABTECH). The results were analyzed by non-linear regression (Curve fit) using a GraphPad Prism. The results are shown in FIG. 7.

Figure 7:
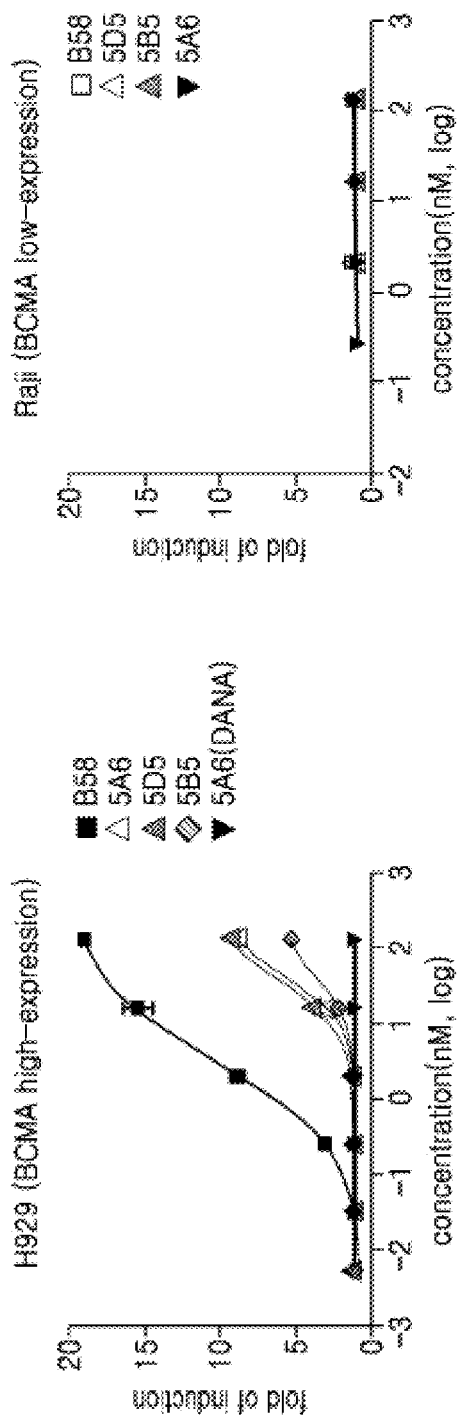
FIG. 7 is a graph showing results of an evaluation of antibody-dependent cell-mediated cytotoxicity (ADCC) of antibodies B58, 5A6, 5D5, 5B5, and 5A6 (DANA) to H929 cells and Raji cells.

As shown in FIG. 7, in H929 cells with high expression of BCMA, the selected anti-BCMA antibodies induced antibody-dependent cell-mediated cytotoxicity (ADCC) in a concentration-dependent manner (B58>5A6=5D5>5B5). In the case of the 5A6 DANA mutant antibody in which the function of the Fc region was inhibited, ADCC was not induced, and it was confirmed that ADCC was caused by the Fc region of the antibody. For Raji where expression of BCMA was not observed, ADCC was not caused. Therefore, it was confirmed that the selected antibodies B58, 5A6, 5D5, and 5B5 can specifically bind to BCMA-expressing cancer cells, and thus may induce antibody cytotoxicity through Fc function.

3. Evaluation of Tumor Growth Inhibition of Anti-BCMA IgG Antibody Mouse Model Transplanted with Cancer Cell Line (1) Evaluation of Tumor Growth Inhibition in Multiple Myeloma Cancer Cell Line H929-Transplant Mouse Model 6-week-old male CB17-SCID mice were used for animal experiments after 7 days of acclimation. Before cell transplantation, hair was removed from the mouse cell transplant site, and an ear tag for individual identification was attached to the ear.

Multiple myeloma cancer cell line H929 cultured according to cell transplantation conditions were collected on the cell transplanting date, and a cell count/viability was measured in PBS with a Beckman coulter device. Finally, the cell suspension was prepared such that the number of cells to be administered per 100 μl of PBS was $1×10^7$ cells/each subject. Matrigel (BD) was added in the same volume as the cell suspension and mixed with a pipette. After inhalation anesthesia of the mice with isoflurane, 200 μl of the cell suspension was subcutaneously administered to the right dorsum. The mice were placed in cages, and it was finally confirmed if there was no problem with activity after the mice were awaken from anesthesia. The tumor size was obtained by measuring the long and short axes of tumors by using a caliper, and calculating a final tumor size using the following equation.

$$\text{Tumor size (mm}^3\text{)}=(0.5)\times(\text{long axis})\times(\text{short axis})^2$$

Drug administration was started when the tumor size reached 269 mm³ on average. Administration drugs were administered to 5 groups (n=7 each) of the control group (PBS) and four anti-BCMA IgG antibodies (B58, 5A6, 5D5, and 5B5). Drugs were prepared at 2 mg/ml (based on 20 g; 100 μl/head). The administration dose was 10 mg/kg, and the drug was administered twice a week, a total of 5 times, by intravenous tail injection. Body weight was measured using an animal scale. The body weight and tumor size were measured twice a week. On the 21st day after drug administration, the body weight and tumor size were measured, and the mice were euthanized to extract tumors from each mouse to measure the tumor weight.

Figure 8A:
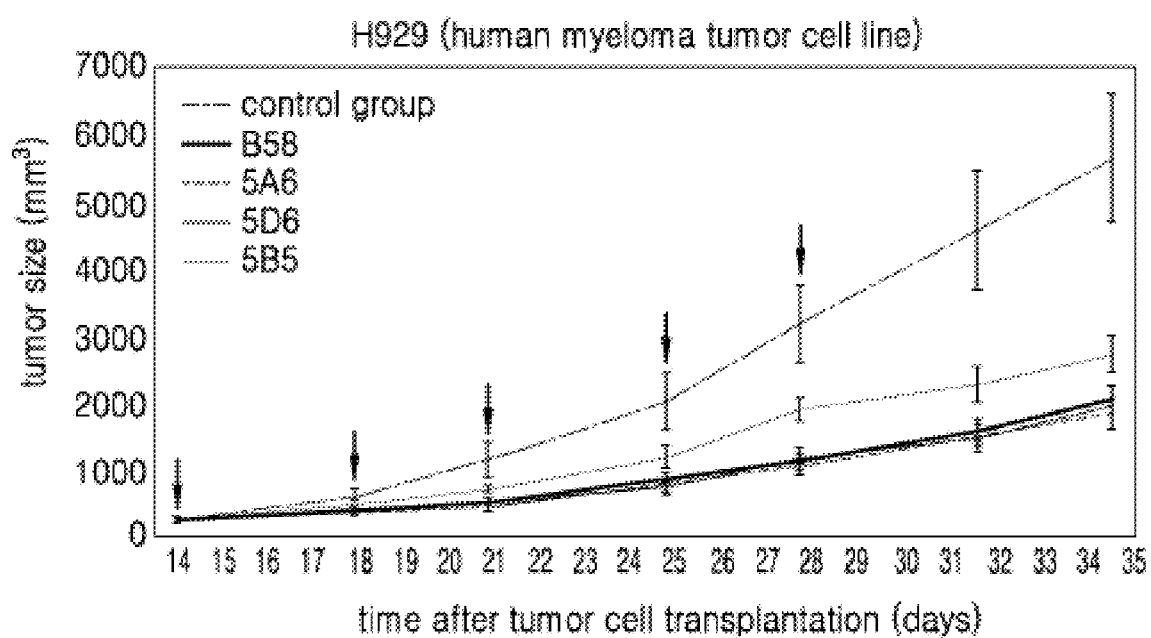
FIGS. 8A, 8B and 8C are graphs showing tumor size ($mm^2$), tumor size ($mm^2$) per antibody, and tumor weight (g) per antibody, respectively, according to time (days) after injection of multiple myeloma cancer cell line H929.
Figure 8B:
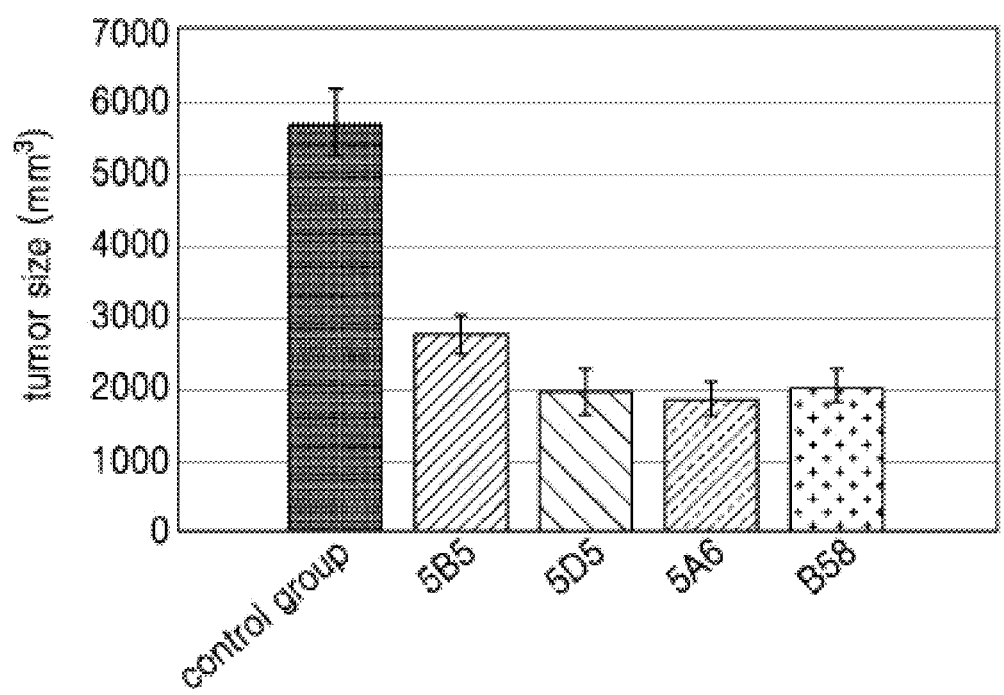
Figure 8C:
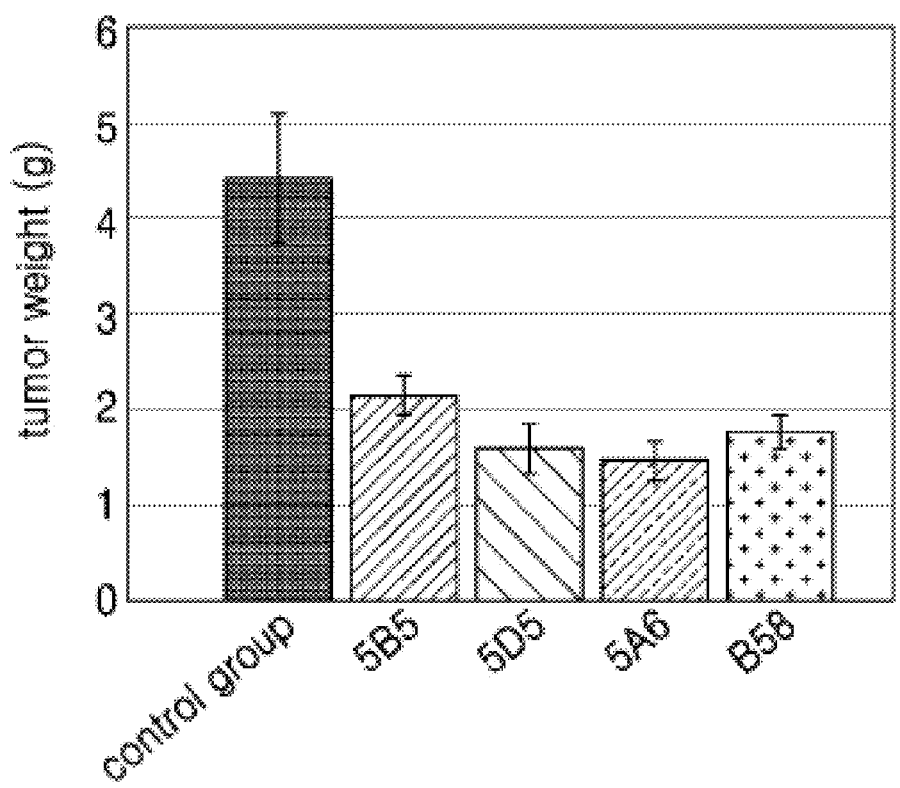

Tumor size (mm³) according to time (days) after tumor injection, tumor size (mm³) for each antibody, and tumor weight (g) for each antibody are shown in FIGS. 8A to 8C, in which arrows indicate drug administration time points. Table 10 shows the volume reduction rate (%) and the weight reduction rate (%) for each antibody compared to the control group (p<0.001).

TABLE 10

| Antibody | Volume reduction rate (%) | Weight reduction rate (%) |
| --- | --- | --- |
| 5B5 | 51.7 | 51.2 |
| 5D5 | 65.7 | 63.9 |
| 5A6 | 67.4 | 66.8 |
| B58 | 63.8 | 60.2 |

As shown in FIGS. 8A to 8C and Table 10, a tumor growth inhibitory effect was observed in the groups administered with four anti-BCMA IgG antibodies (B58, 5A6, 5D5, and 5B5), compared to the control group (PBS), in the H929-transplant mouse model. As a result of the final analysis of the tumor size of each group, the tumors of the antibody treatment groups of the present application were reduced by about 51.7% to about 67.4%, compared to the tumor size of the control group. As a result of one-way analysis of variance, statistical significance was found in the four anti-BCMA IgG antibodies compared to the control group (PBS) (p<0.001). Therefore, it was verified that when multiple myeloma was treated with the selected antibodies, the growth of tumors was significantly inhibited. In addition, according to evaluation results of the antibody-dependent cytotoxicity or BCMA to ligand binding interference, antibodies 5D5 and 5A6 showed lower activities than antibody B58. However, antibodies 5D5 and 5A6 showed an equivalent or greater effect than antibody B58 in in vivo efficacy evaluation. This means that the two antibodies may recognize epitopes that are advantageous for tumor growth inhibition, or the antibodies themselves may have excellent physical properties.

(2) Evaluation of Tumor Growth Inhibition in Mouse Model Transplanted with Multiple Myeloma Cancer Cell Line OPM-2

As described in Example 3.3(1), multiple myeloma cancer cell line OPM2 was transplanted into mice, and tumor growth inhibition by administration of antibodies was evaluated.

Drug administration was started when the tumor size reached 172 mm³ on average. Drugs were administered to 4 groups (n=9 for each), including a control group (PBS) and three anti-BCMA IgG antibody groups (B58, 5A6, and 5D5). The administered drugs were prepared at 2 mg/ml (based on 20 g; 100 μl/head) to reach an administration dose of 10 mg/kg. The administration dose was 10 mg/kg, and the drug was administered twice a week, a total of 5 times, by intravenous tail injection. On the 27th day after drug administration, the body weight and tumor size were measured, and the mice were euthanized to extract tumors from each mouse to measure the tumor weight.

Figure 9A:
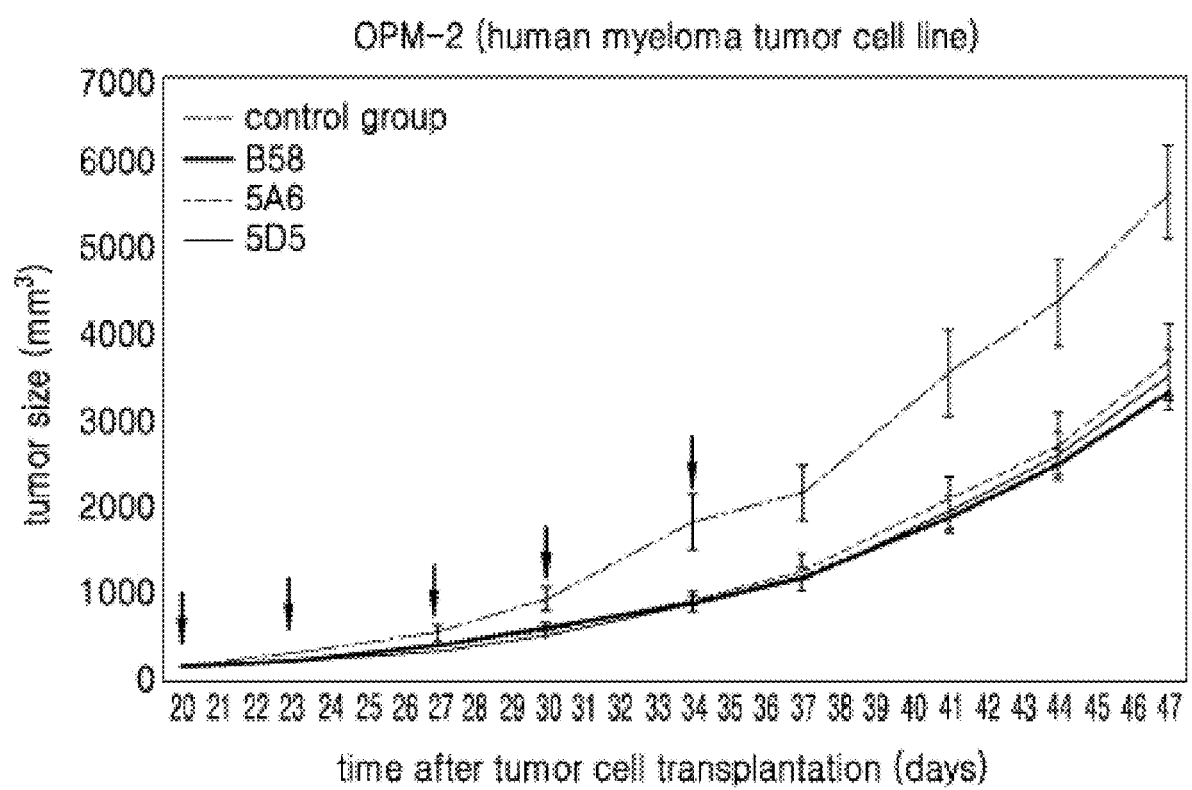
FIGS. 9A, 9B and 9C are graphs showing tumor size ($mm^2$), tumor size ($mm^2$) per antibody, and tumor weight (g) per antibody, respectively, according to time (days) after injection of multiple myeloma cancer cell line OPM-2.
Figure 9B:
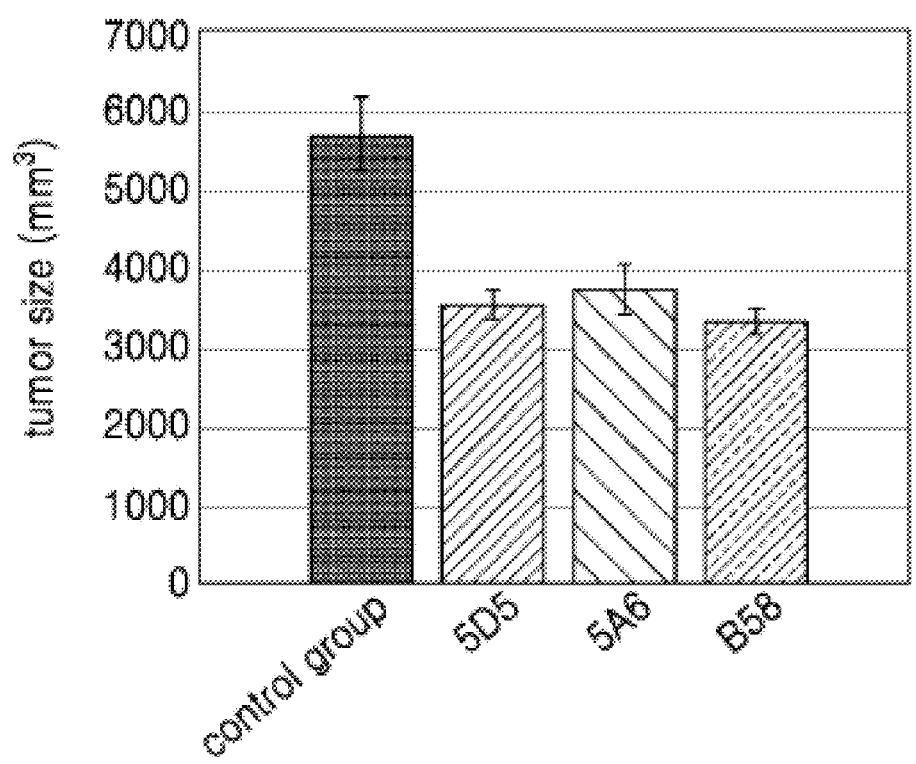
Figure 9C:
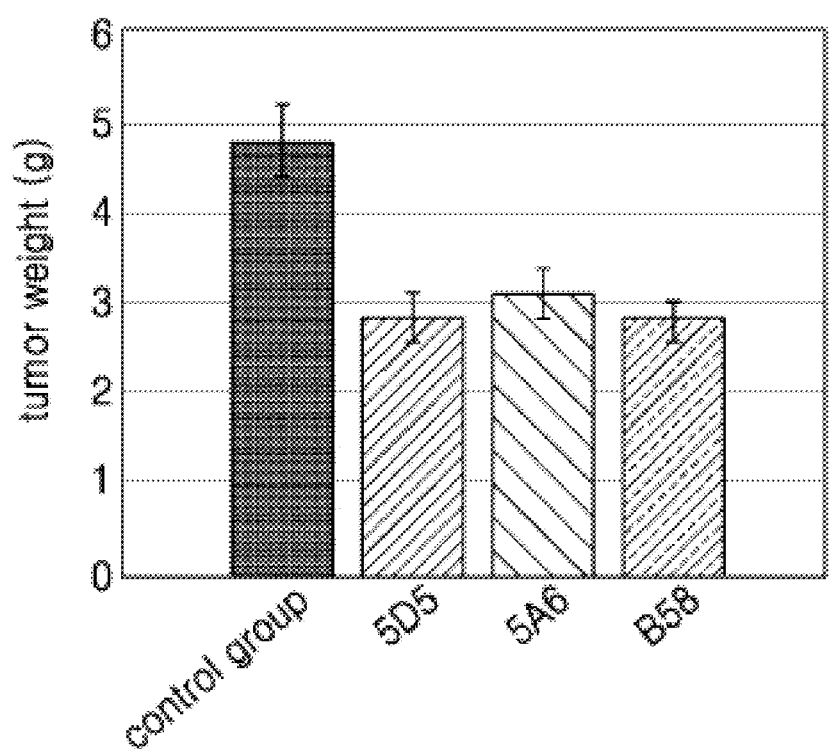

Tumor size (mm³), tumor size (mm³) for each antibody, and tumor weight (g) for each antibody according to time (days) after injection to tumors are shown in FIGS. 9A to 9C, in which arrows indicate drug administration time points. Table 11 shows the volume reduction rate (%) and the weight reduction rate (%) for each antibody compared to the control group (p<0.001).

TABLE 11

| Antibody | Volume reduction rate (%) | Weight reduction rate (%) |
| --- | --- | --- |
| 5D5 | 38.5 | 40.5 |
| 5A6 | 35.4 | 35.1 |
| B58 | 42.5 | 41.4 |

As shown in FIGS. 9A to 9C and Table 11, a tumor growth inhibitory effect was observed in the groups administered with three anti-BCMA IgG antibodies (B58, 5A6, and 5D5), compared to the control group (PBS), in the OPM-2-transplant mouse model. As a result of the final analysis of the tumor size of each group, the degree of tumor inhibition in each group, compared to the control group, was found to be 42.5% for antibody B58, 35.4% for antibody 5A6, and 38.5% for antibody 5D5. As a result of weight measurement, the weight reduction rate was 41.4% for antibody B58, 35.1% for antibody 5A6, and 40.5% for antibody 5D5, compared to the control group. As a result of one-way analysis of variance, anti-tumor effects of the three anti-BCMA IgG antibodies, as compared to the control group, were statistically significant (p<0.001), and the differences in tumor size and tumor weight between the three antibodies were not statistically significant. As shown in FIGS. 6 and 7, according to evaluation results of the antibody-dependent cytotoxicity or BCMA to ligand binding interference, antibodies 5D5 and 5A6 showed lower activities than antibody B58. However, antibodies 5D5 and 5A6 showed equivalent effects than antibody B58 in in vivo efficacy evaluation. This means that the two antibodies may recognize epitopes that are advantageous for tumor growth inhibition, or the antibodies themselves may be have excellent physical properties.

4. Confirmation of Binding Ability of Mutant Antibodies 5A6 and 5D5 to Target Antigen (1) Confirmation of Binding Ability of Wild-Type Antibodies 5A6 and 5D5 and Mutant Antibodies 5A6 and 5D5 to Recombinant BCMA As described in Example 1.5, anti-BCMA antibodies 5A6 and 5D5 were mutated to thereby prepare and purify eight mutant antibodies of 5A6 and five mutant antibodies of 5D5. Binding avidities of the mutated antibodies and wide-type antibodies to recombinant protein were analyzed, and the results are shown in FIGS. 10A and 10B.

Figure 10A:
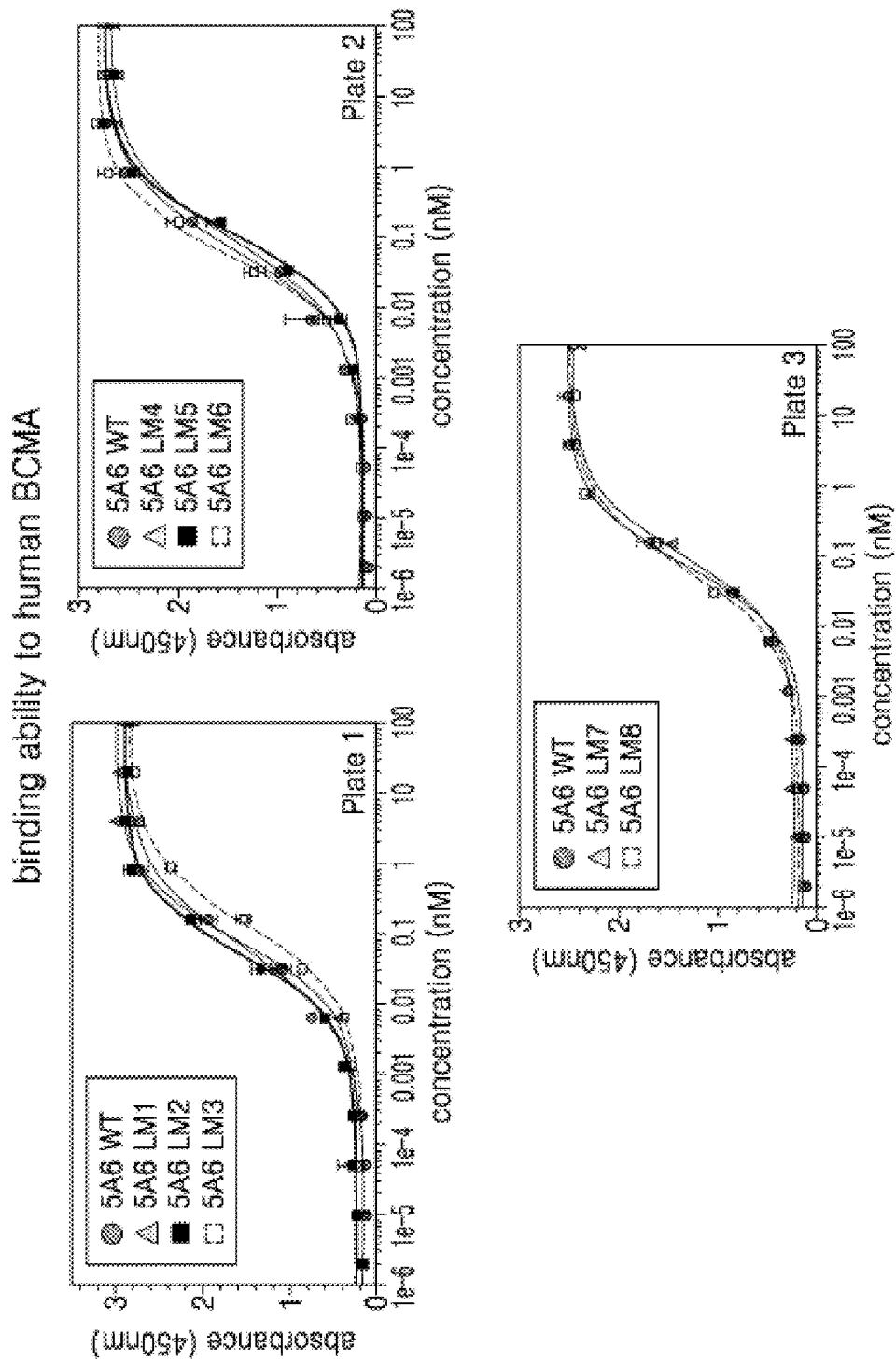
FIGS. 10A and 10B are graphs showing the binding ability of mutant antibodies 5A6 and 5D5 and wild-type antibodies thereof to target antigens.
Figure 10B:
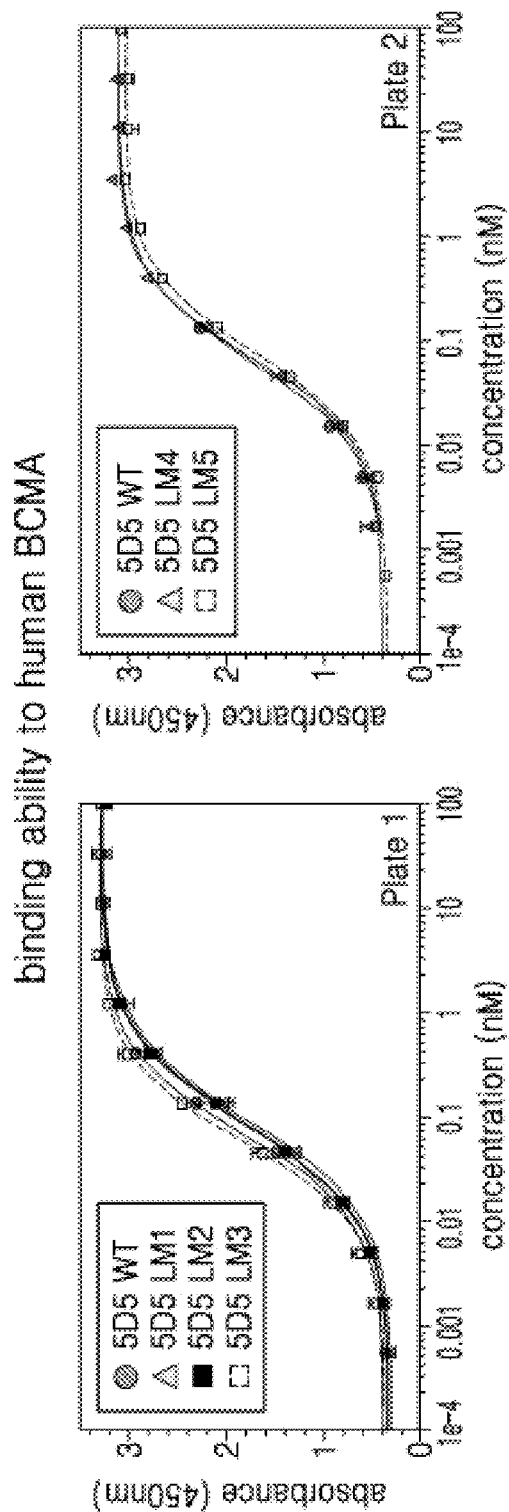

As shown in FIGS. 10A and 10B, 6 of the 8 mutant antibodies of 5A6 (5A6 LM1, 5A6 LM3, 5A6 LM4, 5A6 LM5, 5A6 LM7, and 5A6 LM8) had the same or lower binding activity, as compared to the wild-type antibody, whereas two antibodies (5A6 LM2 and 5A6 LM6) showed increased binding ability to antigen, as compared to the wild-type antibody. In the case of 5D5, two of the five mutant antibodies (5D5 LM1 and 5D5 LM2) had reduced antigen-binding activities as compared to wild type 5D5, whereas the other three mutant antibodies (5D5 LM3, 5D5 LM4, and 5D5 LM5) exhibited the antigen-binding activities equivalent to that of the wild type 5D5. The half maximal effective concentration ($EC_{50}$) (nM) for each antibody is represented in Table 12.

TABLE 12

| Clone name | $EC_{50}$ (nM) |
| --- | --- |
| 5A6 WT (Plate 1) | 0.0631 |
| 5A6 WT (Plate 2) | 0.0643 |
| 5A6 WT (Plate 3) | 0.077 |
| 5A6 LM1 | 0.0818 |
| 5A6 LM2 | 0.0509 |
| 5A6 LM3 | 0.133 |
| 5A6 LM4 | 0.0823 |
| 5A6 LM5 | 0.103 |
| 5A6 LM6 | 0.0537 |
| 5A6 LM7 | 0.105 |
| 5A6 LM8 | 0.068 |
| 5D5 WT (Plate 1) | 0.0708 |
| 5D5 WT (Plate 2) | 0.0652 |
| 5D5 LM1 | 0.0939 |
| 5D5 LM2 | 0.0858 |
| 5D5 LM3 | 0.0593 |
| 5D5 LM4 | 0.0708 |
| 5D5 LM5 | 0.0763 |

(2) Confirmation of Binding Ability of Wild-Type 5A6, Wild-Type 5D5, and Mutants Thereof to BCMA on Cell Surface The binding avidities to cell-surface antigens were compared between wild-type antibodies and mutant antibodies thereof.

Figure 10C:
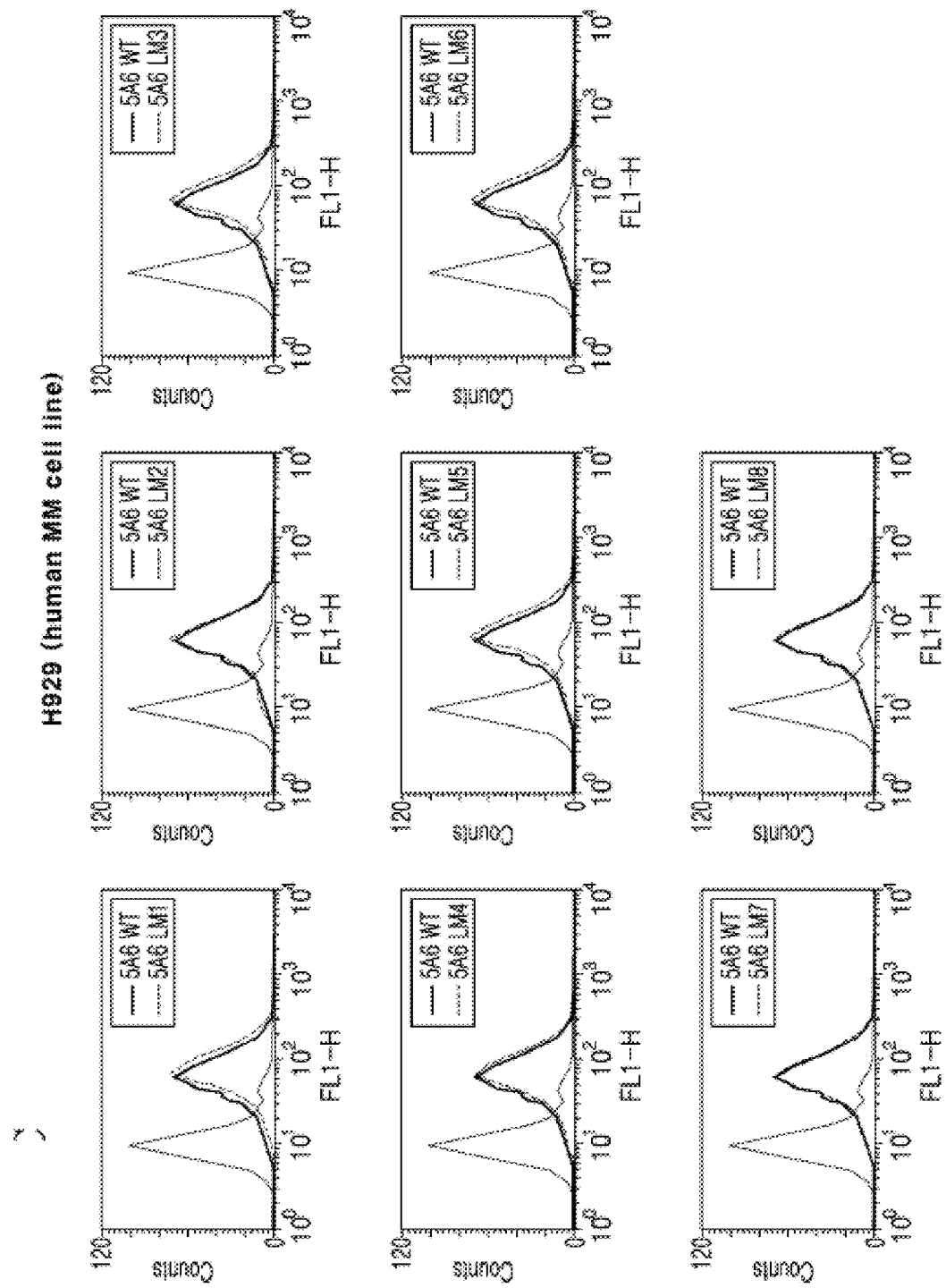
FIGS. 10C and 10D are graphs showing results of measuring, by FACS, the binding ability of selected antibodies to mutant antibodies 5A6 and 5D5 and wild-type antibodies to cell-surface BCMA.
Figure 10D:
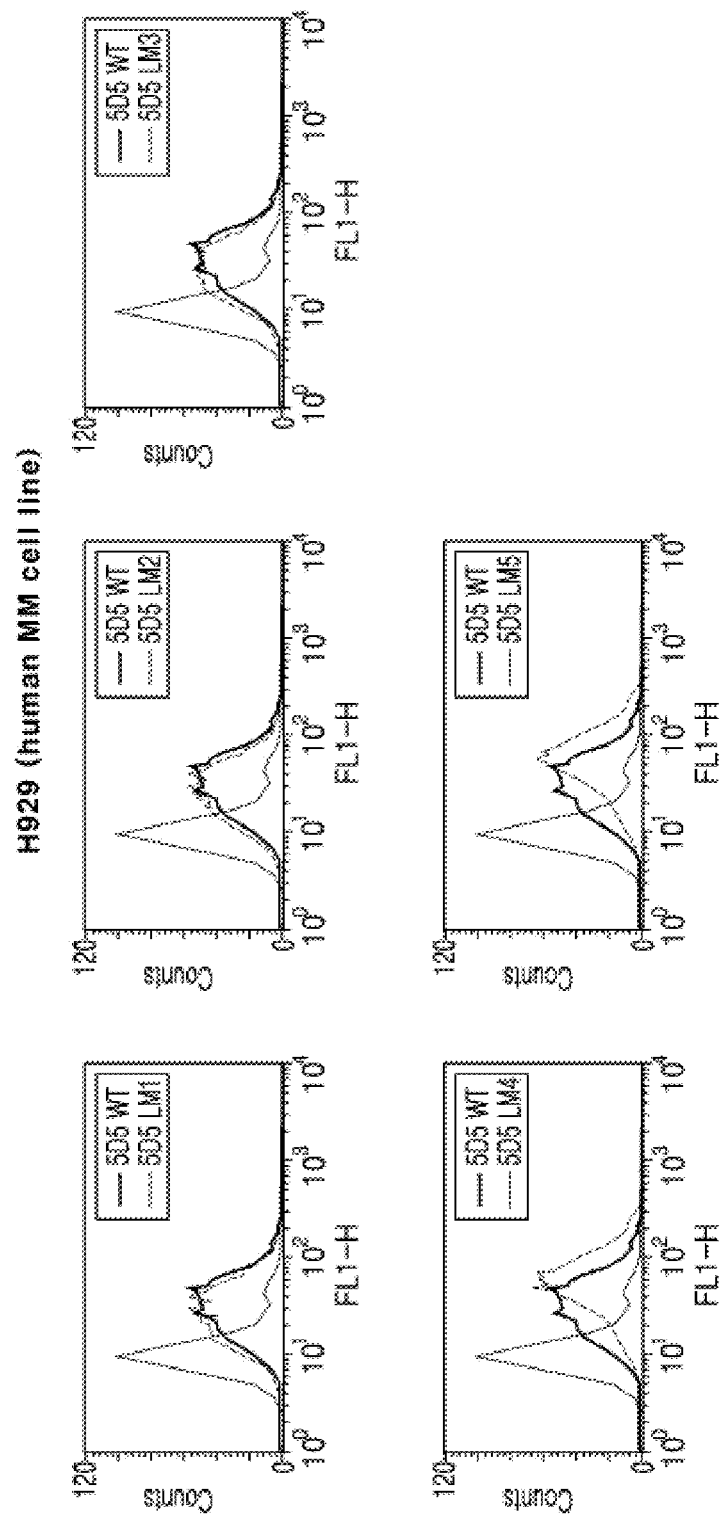

Wild-type 5A6 antibody, wild-type 5D5 antibody, and mutant antibodies thereof were added to multiple myeloma cancer cells H929 (ATCC, CRL-9068™) on which BCMA was highly expressed, and the binding levels of the antibodies to the cell surface were measured by fluorescence-activated cell sorting (FACS). The fluorescence intensities on the cell surface were measured, and the results are represented in FIGS. 10C and 10D. The mean fluorescence intensity (MFI) of each antibody is shown in Table 13.

TABLE 13

| Clone name | MFI |
| --- | --- |
| 5A6 WT | 68.25 |
| 5A6 LM1 | 83.42 |
| 5A6 LM2 | 66.65 |
| 5A6 LM3 | 84.64 |
| 5A6 LM4 | 77.14 |
| 5A6 LM5 | 81.44 |
| 5A6 LM6 | 78.9 |
| 5A6 LM7 | 71.08 |
| 5A6 LM8 | 68.61 |
| 5D5 WT | 36.35 |
| 5D5 LM1 | 32 |
| 5D5 LM2 | 29 |
| 5D5 LM3 | 31.5 |
| 5D5 LM4 | 62.3 |
| 5D5 LM5 | 73.6 |

As shown in FIGS. 10C, 10D, and Table 13, in the case of antibody 5A6, the cell binding abilities of five mutant antibodies (5A6 LM1, 5A6 LM3, 5A6 LM4, 5A6 LM5, and 5A6 LM6) were increased as compared with the cell binding ability of wild-type antibody 5A6. In addition, the cell binding intensities of two mutant antibodies (5D5 LM4 and 5D5 LM5) were surely increased as compared to the cell binding ability of wild-type antibody 5D5. Therefore, it was found that due to partial changes in the CDR amino acids of the wild-type antibodies, the binding ability to recombinant BCMA and cell surface BCMA was partially improved.

(3) Affinity Analysis of Mutant Antibodies 5A6 LM6 and 5D5 LM4 to Human BCMA

Target antigen-binding affinities of mutant antibodies 5A6 LM6 and 5D5 LM4 and wild-type antibodies thereof to the human monomeric BCMA antigen were analyzed.

In particular, the prepared antibodies were diluted with a 1×HPS-EP buffer (GE Healthcare, BR-1006-69). The target antigen-binding affinity analysis was performed using a Biacore T200 (GE Healthcare). The antibodies were flowed onto a protein A chip at a contact time of 60 seconds, a stabilization time of 30 seconds, and a flow rate of 30 μl/min until a capture level reached 128 RU (Response Unit), thereby preparing an antibody-captured protein A chip.

The antigen was sequentially diluted with a 1×HPS-EP buffer, by 2-fold each time, from 100 nM to 6.25 nM, thereby preparing a total of six samples. The 1×HPS-EP buffer was used as a negative control group (blank).

The prepared antigen was flowed across the antibody-captured protein A chip at a flow rate of 30 μl/min for an association time of 60 seconds, followed by a disassociation phase for 180 seconds. Regeneration was performed with a 10-mM Glycine-HCL (pH 1.5) buffer (GE Healthcare, BR-1003-54) at a flow rate of 30 μl/min for a contact time of 30 seconds.

Figure 11:
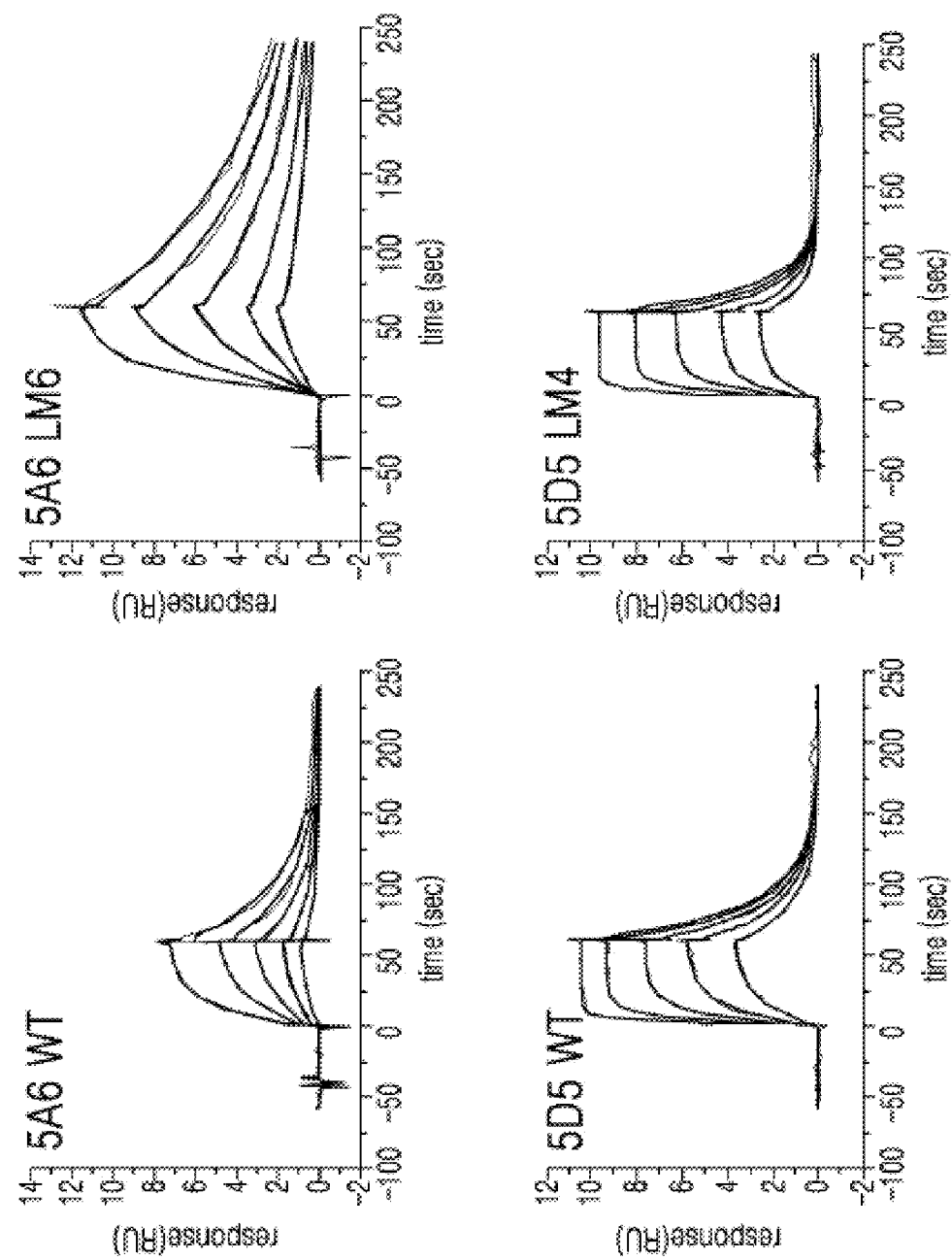
FIG. 11 is a graph showing the binding ability of mutant antibodies 5A6 LM6 and 5D5 LM4 and wild-type antibodies thereof to recombinant human BCMA antigens.

Graphs of response (in reaction unit (RU)) with respect to reaction time (seconds) are represented in FIG. 11, and the target antigen-binding affinities of the antibodies calculated from the graphs are represented in Table 14.

TABLE 14

| Antibody name | Suitable model | Capture level (Target = 128 RU) | ka (1/Ms) | kd (1/s) | $K_D$ (M) | $R_{maximum}$ (RU) (Target = 12.5 RU) | Chi² |
|---|---|---|---|---|---|---|---|
| 5A6 WT | 1:1 binding | 110.9~113.3 | $3.99 \times 10^5$ | $2.49 \times 10^{-2}$ | $26.24 \times 10^{-8}$ | 10.45 | 0.0436 |
| 5A6 LM6 | 1:1 binding | 120.6~122.6 | $5.09 \times 10^5$ | $0.922 \times 10^{-2}$ | $1.81 \times 10^{-8}$ | 13.21 | 0.0304 |
| 5D5 WT | 1:1 binding | 107.6~108.1 | $2.632 \times 10^6$ | $6.013 \times 10^{-2}$ | $2.284 \times 10^{-8}$ | 11.00 | 0.0186 |
| 5D5 LM4 | 1:1 binding | 98.9~99.4 | $4.169 \times 10^6$ | $5.937 \times 10^{-2}$ | $1.424 \times 10^{-8}$ | 11.62 | 0.0131 |

As shown in FIG. 11 and Table 14, the mutant antibody 5A6 LM6 exhibited a lower dissociation rate after bound to BCMA, as compared with wild-type 5A6. The mutant antibody 5D5 LM4 exhibited an increased rate of association to BCMA, as compared with wild-type 5A6. Therefore, it was found that the mutant antibodies 5A6 LM6 and 5D5 LM4 exhibited enhanced affinities to the target antigen, as compared with corresponding wild-type antibodies.

5. Evaluation of Antibody-Dependent Cell-Mediated Cytotoxicity (ADCC) of Mutant Antibodies 5A6 LM6 and 5D5 LM4

In order to assess the antibody-dependent cell-mediated cytotoxicity (ADCC) of mutant antibodies 5A6 LM6 and 5D5 LM4 compared to the corresponding wild-type antibodies, measurement was performed according to the method described in Example 3.2. The measured ADCC results are represented in FIG. 12.

Figure 12:
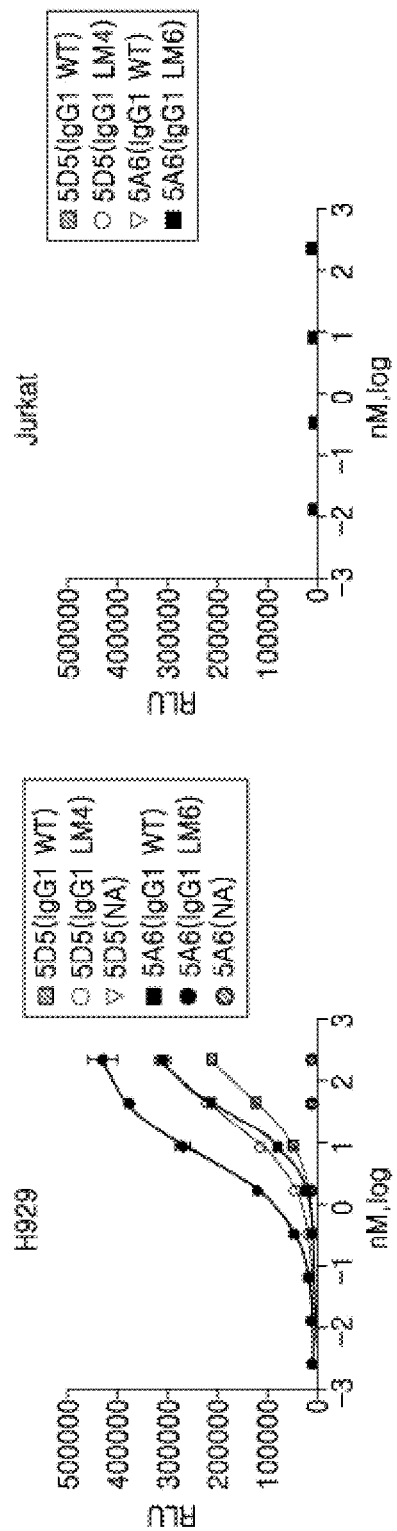
FIG. 12 is a graph showing results of an evaluation of antibody-dependent cell-mediated cytotoxicity (ADCC) of mutant antibodies 5A6 LM6 and 5D5 LM4 and wild-type antibodies thereof.

As shown in FIG. 12, the mutant antibodies 5A6 LM6 and 5D5 LM4 exhibited an increased ADCC in BCMA-high expression cell line H929, as compared to the wild-type antibodies (see FIG. 12, left). Meanwhile, wild-type antibodies 5A6 WT and 5D5 WT, and mutant antibodies thereof were unable to induce antibody-dependent cell-mediated cytotoxicity (ADCC) in Jurkat cell lines in which BCMA was not expressed (see FIG. 12, right).

In addition, mutant antibodies 5A6 NA and 5D5 NA in which the Fc region of the wild-type antibodies was functionally inhibited were unable to induce antibody-dependent cell-mediated cytotoxicity (ADCC) in BCMA-high expression H929 cell lines (see FIG. 12, left).

Accordingly, mutant antibodies 5A6 LM6 and 5D5 LM4 exhibited an increased ability to induce BCMA-dependent cytotoxicity, as compared to the corresponding wild-type antibodies, which is consistent with an increase resulting from antigen-binding improvement, as proven in Example 3.4. Therefore, it was shown that mutant antibodies 5A6 LM6 and 5D5 LM4 are able to induce effective cancer cell growth inhibition, as compared with the corresponding wild-type antibodies.

6. Tumor Growth Inhibition Evaluation of Antibody 5A6 LM6 or 5D5 LM4 in Cancer Cell-Transplanted Mouse Model Human cancer-transplanted tumor mice were constructed by transplanting human myeloma NIH-H929 cell lines, in which BCMA is highly expressed, into a severe combined immunodeficiency (SCID) mouse model through the side of mice with $1 \times 10^7$ cells/head for each. After the transplantation, when the tumor size reached 180 mm³ on average, the mice separated into groups (1st day).

Five different antibodies, i.e., mutant antibodies 5A6 LM6 and 5D5 LM4, and the corresponding wild type antibodies 5A6 WT and 5D5 WT, and human IgG1 (InVivo Plus human IgG1 isotype control, BioXCell) as a negative control group were administered into tail veins of the mice, by 10 mg/kg each time with a 1-mL syringe, twice a week, a total of 4 times (1st day, 4th day, 7th day, and 11th day). After the first administration, the tumor sizes and weights in the tumor-transplanted mice were measured using a digital caliper, and an animal scale, twice a week (1st day, 4th day, 7th day, 11th day, 18th day, 22nd day, and 25th day).

After 2 weeks from the last administration of the experimental materials, the mice were sacrificed using $CO_2$ gas, tumors were extracted, and the volumes and weights of the extracted tumors were measured. The tumor volumes according to time are represented in FIG. 13, and the tumor volume reduction rate (%) and the tumor weight reduction rate (%) in the administration groups compared with the negative group are shown in Table 15.

TABLE 15

| Antibody | Volume reduction rate (%) | Weight reduction rate (%) |
|---|---|---|
| 5A6 WT | 90.3 | 84.1 |
| 5A6 LM6 | 81.5 | 71.1 |
| 5D5 WT | 61.9 | 51.9 |
| 5D5 LM4 | 65.8 | 55.8 |

Figure 13:
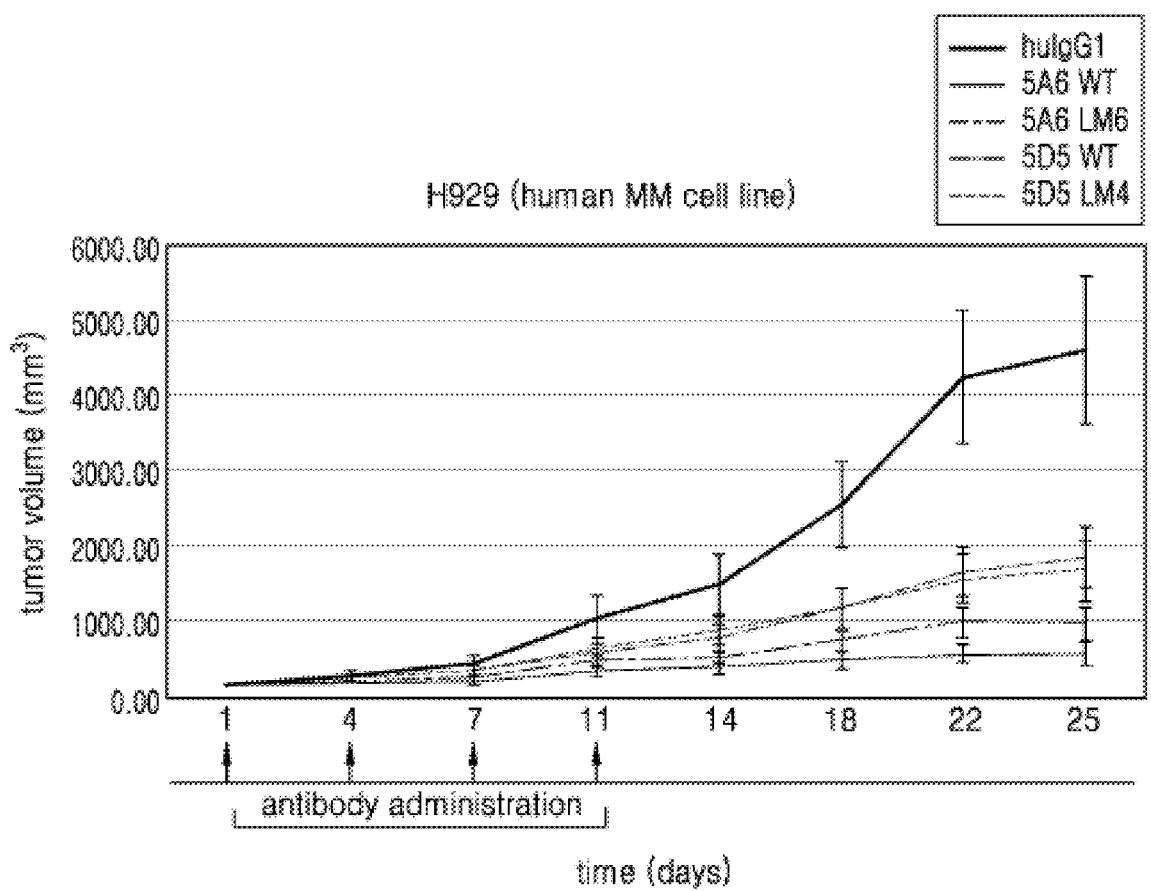
FIG. 13 is a graph of tumor size ($mm^2$) according to time (days) when mutant antibodies 5A6 LM6 and 5D5 LM4 and wild-type antibodies thereof were administered to mice into which the multiple myeloma cancer cell line H929 was injected.

As shown in FIG. 13, four different anti-BCMA antibodies (5A6 WT, 5A6 LM6, 5D5 WT, and 5D5 LM4) significantly reduce tumor growth compared to human IgG1 antibody which is a negative control group. In addition, as shown in Table 15, the four administered anti-BCMA antibodies showed statistical significance in the tumor growth inhibition rate (TGI %) compared to the negative control group (one-way analysis of variance, P-value<0.05). However, between the wild-type antibodies and their mutant antibodies (5A6 WT vs 5A6 LM6, and 5D5 WT vs 5D5 LM4), tumor size reduction was analyzed to be equivalent, and there was no statistical significance between the groups.

As a result, it was found that mutant antibodies 5A6 LM6 and 5D5 LM4 showed increased in vitro activity (target antigen-binding ability and antibody-dependent cell-mediated cytotoxicity (ADCC) induction), and an equal level of tumor growth inhibitory ability to that of the respective wild type antibodies in an in vivo activity evaluation.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52 (e).

What is claimed is:

1. An antibody or an antigen-binding fragment thereof that binds to B-cell maturation antigen (BCMA), wherein said antibody or antigen-binding fragment comprises:

(a) a complementarity-determining region-H1 (CDR-H1) comprising the amino acid sequence of SEQ ID NO: 27,
a CDR-H2 comprising the amino acid sequence of SEQ ID NO: 35,
a CDR-H3 comprising the amino acid sequence of SEQ ID NO: 46,
a CDR-L1 comprising the amino acid sequence of SEQ ID NO: 56,
a CDR-L2 comprising the amino acid sequence of SEQ ID NO: 66, and
a CDR-L3 comprising the amino acid sequence of SEQ ID NO: 75;

(b) a CDR-H1 comprising the amino acid sequence of SEQ ID NO: 28,
a CDR-H2 comprising the amino acid sequence of SEQ ID NO: 36,
a CDR-H3 comprising the amino acid sequence of SEQ ID NO: 47,
a CDR-L1 comprising the amino acid sequence of SEQ ID NO: 57,
a CDR-L2 comprising the amino acid sequence of SEQ ID NO: 67, and
a CDR-L3 comprising the amino acid sequence of SEQ ID NO: 76;

(c) a CDR-H1 comprising the amino acid sequence of SEQ ID NO: 29,
a CDR-H2 comprising the amino acid sequence of SEQ ID NO: 37,
a CDR-H3 comprising the amino acid sequence of SEQ ID NO: 48,
a CDR-L1 comprising the amino acid sequence of SEQ ID NO: 58,
a CDR-L2 comprising the amino acid sequence of SEQ ID NO: 68, and
a CDR-L3 comprising the amino acid sequence of SEQ ID NO: 77;

(d) a CDR-H1 comprising the amino acid sequence of SEQ ID NO: 30,
a CDR-H2 comprising the amino acid sequence of SEQ ID NO: 38,
a CDR-H3 comprising the amino acid sequence of SEQ ID NO: 49,
a CDR-L1 comprising the amino acid sequence of SEQ ID NO: 59,
a CDR-L2 comprising the amino acid sequence of SEQ ID NO: 68, and
a CDR-L3 comprising the amino acid sequence of SEQ ID NO: 78;

(e) a CDR-H1 comprising the amino acid sequence of SEQ ID NO: 28,
a CDR-H2 comprising the amino acid sequence of SEQ ID NO: 36,
a CDR-H3 comprising the amino acid sequence of SEQ ID NO: 47,
a CDR-L1 comprising the amino acid sequence of SEQ ID NO: 120,
a CDR-L2 comprising the amino acid sequence of SEQ ID NO: 67, and
a CDR-L3 comprising the amino acid sequence of SEQ ID NO: 76;

(f) a CDR-H1 comprising the amino acid sequence of SEQ ID NO: 28,
a CDR-H2 comprising the amino acid sequence of SEQ ID NO: 36,
a CDR-H3 comprising the amino acid sequence of SEQ ID NO: 47,
a CDR-L1 comprising the amino acid sequence of SEQ ID NO: 121,
a CDR-L2 comprising the amino acid sequence of SEQ ID NO: 67, and
a CDR-L3 comprising the amino acid sequence of SEQ ID NO: 76;

(g) a CDR-H1 comprising the amino acid sequence of SEQ ID NO: 28,
a CDR-H2 comprising the amino acid sequence of SEQ ID NO: 36,
a CDR-H3 comprising the amino acid sequence of SEQ ID NO: 47,
a CDR-L1 comprising the amino acid sequence of SEQ ID NO: 57,
a CDR-L2 comprising the amino acid sequence of SEQ ID NO: 67, and
a CDR-L3 comprising the amino acid sequence of SEQ ID NO: 122;

(h) a CDR-H1 comprising the amino acid sequence of SEQ ID NO: 28,
a CDR-H2 comprising the amino acid sequence of SEQ ID NO: 36,
a CDR-H3 comprising the amino acid sequence of SEQ ID NO: 47,
a CDR-L1 comprising the amino acid sequence of SEQ ID NO: 57,
a CDR-L2 comprising the amino acid sequence of SEQ ID NO: 67, and
a CDR-L3 comprising the amino acid sequence of SEQ ID NO: 123;

(i) a CDR-H1 comprising the amino acid sequence of SEQ ID NO: 28,
a CDR-H2 comprising the amino acid sequence of SEQ ID NO: 36,
a CDR-H3 comprising the amino acid sequence of SEQ ID NO: 47,
a CDR-L1 comprising the amino acid sequence of SEQ ID NO: 120,
a CDR-L2 comprising the amino acid sequence of SEQ ID NO: 67, and
a CDR-L3 comprising the amino acid sequence of SEQ ID NO: 122;

(j) a CDR-H1 comprising the amino acid sequence of SEQ ID NO: 28,
a CDR-H2 comprising the amino acid sequence of SEQ ID NO: 36,
a CDR-H3 comprising the amino acid sequence of SEQ ID NO: 47,
a CDR-L1 comprising the amino acid sequence of SEQ ID NO: 120,
a CDR-L2 comprising the amino acid sequence of SEQ ID NO: 67, and
a CDR-L3 comprising the amino acid sequence of SEQ ID NO: 123;

(k) a CDR-H1 comprising the amino acid sequence of SEQ ID NO: 28,
a CDR-H2 comprising the amino acid sequence of SEQ ID NO: 36,
a CDR-H3 comprising the amino acid sequence of SEQ ID NO: 47,
a CDR-L1 comprising the amino acid sequence of SEQ ID NO: 121, a CDR-L2 comprising the amino acid sequence of SEQ ID NO: 67, and
a CDR-L3 comprising the amino acid sequence of SEQ ID NO: 122;
(l) a CDR-H1 comprising the amino acid sequence of SEQ ID NO: 28,
a CDR-H2 comprising the amino acid sequence of SEQ ID NO: 36,
a CDR-H3 comprising the amino acid sequence of SEQ ID NO: 47,
a CDR-L1 comprising the amino acid sequence of SEQ ID NO: 121,
a CDR-L2 comprising the amino acid sequence of SEQ ID NO: 67, and
a CDR-L3 comprising the amino acid sequence of SEQ ID NO: 123;
(m) a CDR-H1 comprising the amino acid sequence of SEQ ID NO: 29,
a CDR-H2 comprising the amino acid sequence of SEQ ID NO: 37,
a CDR-H3 comprising the amino acid sequence of SEQ ID NO: 48,
a CDR-L1 comprising the amino acid sequence of SEQ ID NO: 124,
a CDR-L2 comprising the amino acid sequence of SEQ ID NO: 68, and
a CDR-L3 comprising the amino acid sequence of SEQ ID NO: 77,
(n) a CDR-H1 comprising the amino acid sequence of SEQ ID NO: 29,
a CDR-H2 comprising the amino acid sequence of SEQ ID NO: 37,
a CDR-H3 comprising the amino acid sequence of SEQ ID NO: 48,
a CDR-L1 comprising the amino acid sequence of SEQ ID NO: 125,
a CDR-L2 comprising the amino acid sequence of SEQ ID NO: 68, and
a CDR-L3 comprising the amino acid sequence of SEQ ID NO: 77;
(o) a CDR-H1 comprising the amino acid sequence of SEQ ID NO: 29,
a CDR-H2 comprising the amino acid sequence of SEQ ID NO: 37,
a CDR-H3 comprising the amino acid sequence of SEQ ID NO: 48,
a CDR-L1 comprising the amino acid sequence of SEQ ID NO: 126,
a CDR-L2 comprising the amino acid sequence of SEQ ID NO: 68, and
a CDR-L3 comprising the amino acid sequence of SEQ ID NO: 77;
(p) a CDR-H1 comprising the amino acid sequence of SEQ ID NO: 29,
a CDR-H2 comprising the amino acid sequence of SEQ ID NO: 37,
a CDR-H3 comprising the amino acid sequence of SEQ ID NO: 48,
a CDR-L1 comprising the amino acid sequence of SEQ ID NO: 127,
a CDR-L2 comprising the amino acid sequence of SEQ ID NO: 68, and
a CDR-L3 comprising the amino acid sequence SEQ ID NO: 77; and
(q) a CDR-H1 comprising the amino acid sequence of SEQ ID NO: 29,
a CDR-H2 comprising the amino acid sequence of SEQ ID NO: 37,
a CDR-H3 comprising the amino acid sequence of SEQ ID NO: 48,
a CDR-L1 comprising the amino acid sequence of SEQ ID NO: 128,
a CDR-L2 comprising the amino acid sequence of SEQ ID NO: 68, and
a CDR-L3 comprising the amino acid sequence of SEQ ID NO: 77.

2. The antibody or antigen-binding fragment thereof of claim 1, wherein the antibody or antigen-binding fragment comprises a heavy chain variable region comprising an amino acid sequence selected from the group consisting of SEQ ID NOs: 5 to 8.

3. The antibody or antigen-binding fragment thereof of claim 1, wherein the antibody or antigen-binding fragment comprises a light chain variable region-includes comprising an amino acid sequence selected from the group consisting of SEQ ID NOs: 16 to 19 and 107 to 119.

4. The antibody or antigen-binding fragment thereof of claim 1, wherein the antibody or antigen-binding fragment inhibits binding between BCMA and a substance specifically binding to BCMA.

5. The antibody or antigen-binding fragment thereof of claim 4, wherein the substance specifically binding to BCMA is BAFF (B-cell activating factor belonging to the tumor necrosis factor family), APRIL (a proliferation inducing ligand), or a combination thereof.

6. The antibody or the antigen-binding fragment thereof of claim 1, wherein the antigen-binding fragment is scFv, (scFv)$_2$, Fv, Fab, Fab', F(ab')$_2$, or a combination thereof.

7. The antibody or the antigen-binding fragment thereof of claim 1, wherein the antibody or the antigen-binding fragment is conjugated with an anti-cancer drug.

8. A pharmaceutical composition, comprising the antibody or the antigen-binding fragment thereof of claim 1.

9. A method for treating multiple myeloma in an individual in need thereof, the method comprising:
administering the antibody or the antigen-binding fragment thereof of claim 1 to the individual.

* * * * *